United States Patent
Ito et al.

(10) Patent No.: US 11,130,988 B2
(45) Date of Patent: Sep. 28, 2021

(54) METHOD FOR DETECTING A PLURALITY OF SHORT-CHAIN NUCLEIC ACID IN SAMPLE, COMBINATORIAL ANALYSIS KIT, ANALYSIS KIT SUPPLY MANAGEMENT METHOD

(71) Applicant: KABUSHIKI KAISHA TOSHIBA, Minato-ku (JP)

(72) Inventors: Keiko Ito, Kawasaki (JP); Koji Hashimoto, Atsugi (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 441 days.

(21) Appl. No.: 15/919,947

(22) Filed: Mar. 13, 2018

(65) Prior Publication Data
US 2018/0282792 A1    Oct. 4, 2018

Related U.S. Application Data

(63) Continuation of application No. PCT/JP2016/058817, filed on Mar. 18, 2016.

(51) Int. Cl.
*C12Q 1/68* (2018.01)
*C12Q 1/6816* (2018.01)
*C12Q 1/6806* (2018.01)

(52) U.S. Cl.
CPC .............. *C12Q 1/6816* (2013.01); *C12Q 1/68* (2013.01); *C12Q 1/6806* (2013.01)

(58) Field of Classification Search
None
See application file for complete search history.

(56) References Cited

U.S. PATENT DOCUMENTS

| | | |
|---|---|---|
| 2005/0260648 A1 | 11/2005 | Huffel et al. |
| 2006/0003337 A1* | 1/2006 | Brandis ............... C12Q 1/6844 435/6.14 |
| 2006/0057595 A1 | 3/2006 | Lao et al. |
| 2006/0078924 A1 | 4/2006 | Finn et al. |
| 2006/0134639 A1 | 6/2006 | Huffel et al. |
| 2007/0048757 A1 | 3/2007 | Lao et al. |
| 2007/0077570 A1 | 4/2007 | Lao et al. |
| 2007/0111226 A1 | 5/2007 | Tan et al. |
| 2008/0038727 A1 | 2/2008 | Spier |
| 2010/0129822 A1 | 5/2010 | Siva et al. |
| 2015/0031573 A1 | 1/2015 | Wang et al. |
| 2015/0213193 A1* | 7/2015 | Apte ..................... C12Q 1/689 435/6.12 |
| 2016/0362732 A1 | 12/2016 | Takahashi et al. |
| 2017/0191122 A1 | 7/2017 | Hashimoto et al. |

FOREIGN PATENT DOCUMENTS

| | | |
|---|---|---|
| JP | 2005-143492 | 6/2005 |
| JP | 2005-296014 | 10/2005 |
| JP | 2006-67914 | 3/2006 |
| JP | 2007-532100 | 11/2007 |
| JP | 2008-513011 | 5/2008 |
| JP | 2008-513028 | 5/2008 |
| JP | 2008-545430 | 12/2008 |
| JP | 2009-124957 | 6/2009 |
| JP | 4879957 | 2/2012 |
| JP | 4879975 | 2/2012 |
| JP | 2012-509675 | 4/2012 |
| JP | 2015-507928 | 3/2015 |
| WO | WO 2005/098029 A2 | 10/2005 |
| WO | WO 2015/076356 A1 | 5/2015 |
| WO | WO 2016/136033 A1 | 9/2016 |

OTHER PUBLICATIONS

Li et al. (Chem Commun 2011, 47:2595-2597) (Year: 2011).*
International Search Report dated May 24, 2016 in PCT/JP2016/058817, filed on Mar. 18, 2016 (with English Translation).
Written Opinion dated May 24, 2016 in PCT/JP2016/058817, filed on Mar. 18, 2016.
Hui-Ling Chen, et al. "Nucleic acid amplification-based method for microRNA detection", Analytical Methods, vol. 7, No. 6, 2015, 8 pages.
Jiangyan Zhang, et al. "Ultrasensitive quantification of mature microRNAs by real-time PCR based on ligation of a ribonucleotide-modified DNA probe", Chemical Communications, vol. 47, No. 33, 2011, 3 pages.

* cited by examiner

*Primary Examiner* — Stephanie K Mummert
(74) *Attorney, Agent, or Firm* — Oblon, McClelland, Maier & Neustadt, L.L.P.

(57) ABSTRACT

According to one embodiment, a detection method is a method for detecting a plurality of target nucleic acids in a sample. The method includes (a) preparing a chain-elongation nucleic acid set group, a primer set, and a probe immobilized substrate, (b) obtaining the target nucleic acid and a long-chain nucleic acid group containing a first sub-chain-elongation nucleic acid and a second sub-chain-elongation nucleic acid, (c) obtaining an amplification product group by maintaining the long-chain nucleic acid group and the primer set under amplification conditions, (d) detecting presence/absence and/or an amount of hybridization, and (e) detecting the plurality of target nucleic acids.

21 Claims, 19 Drawing Sheets

Specification includes a Sequence Listing.

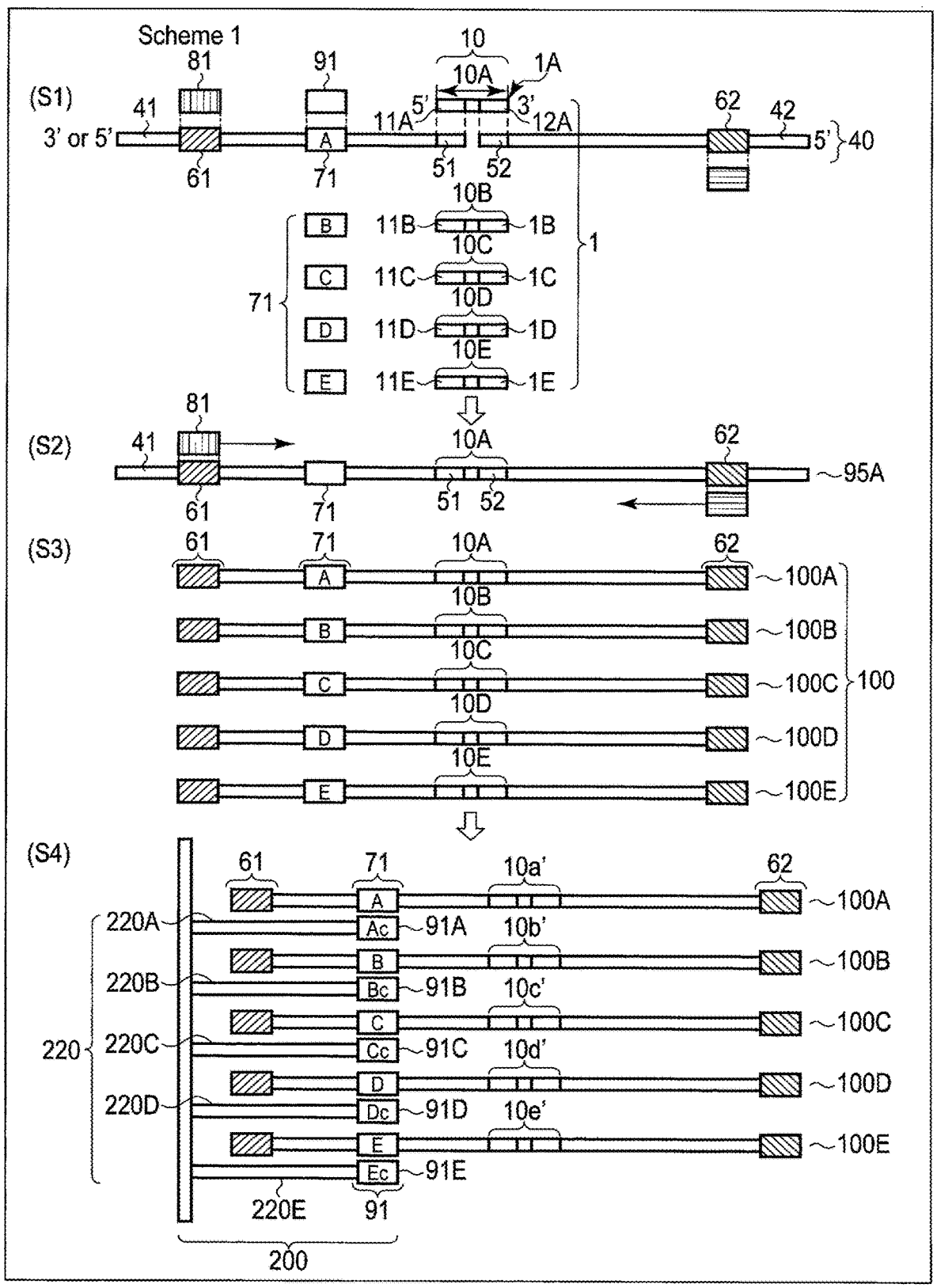
F I G. 1

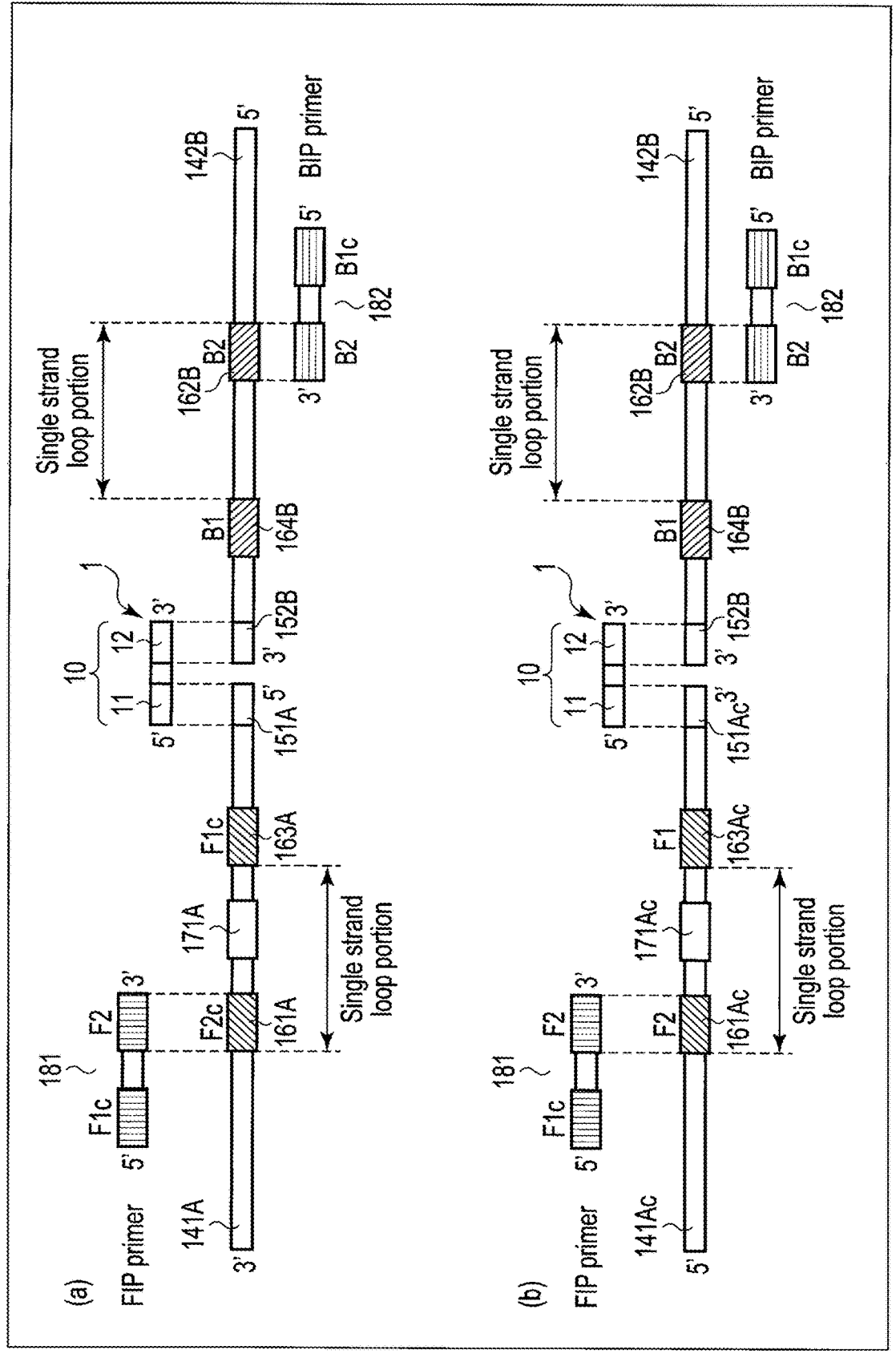
F I G. 4B

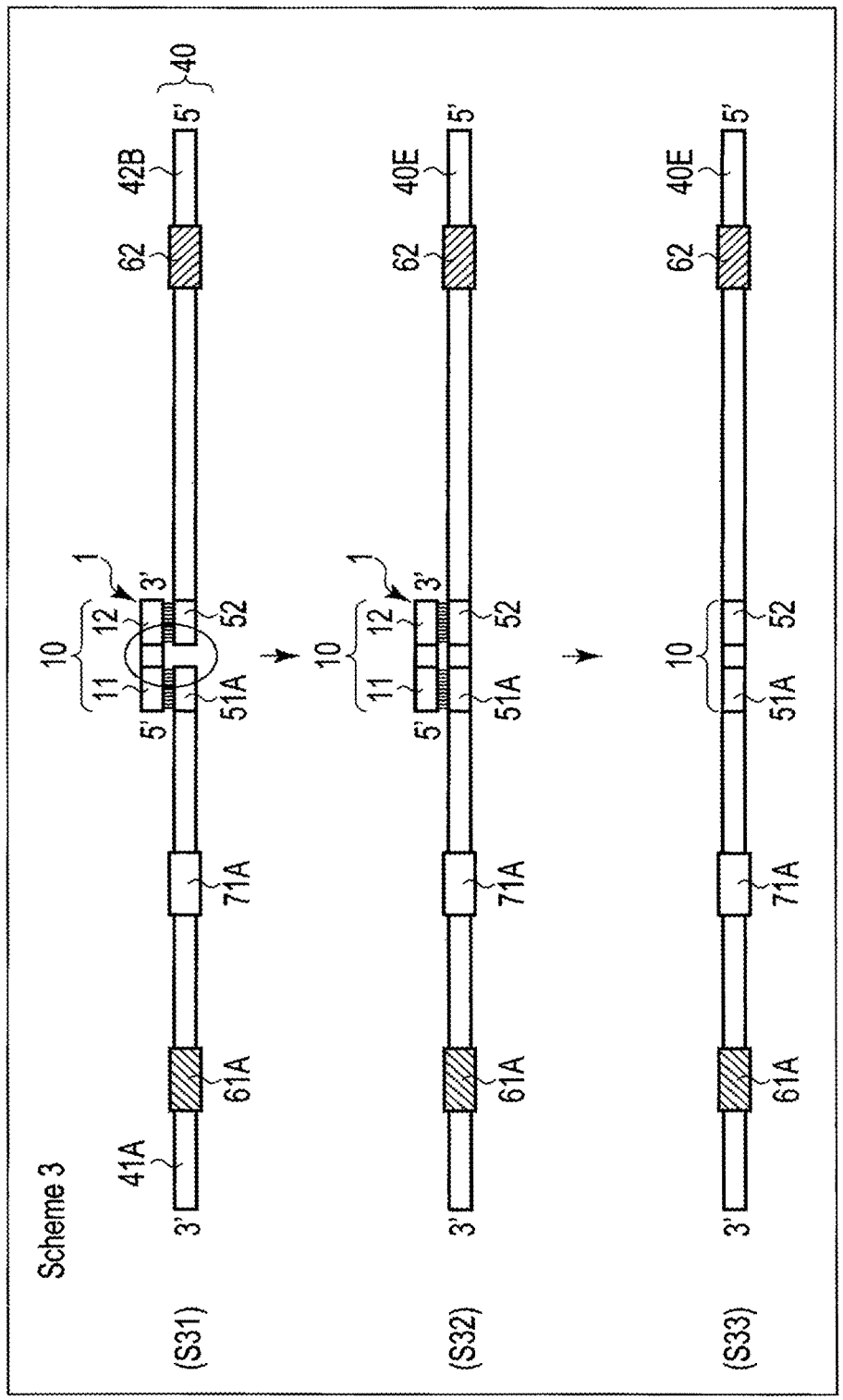
F I G. 6A

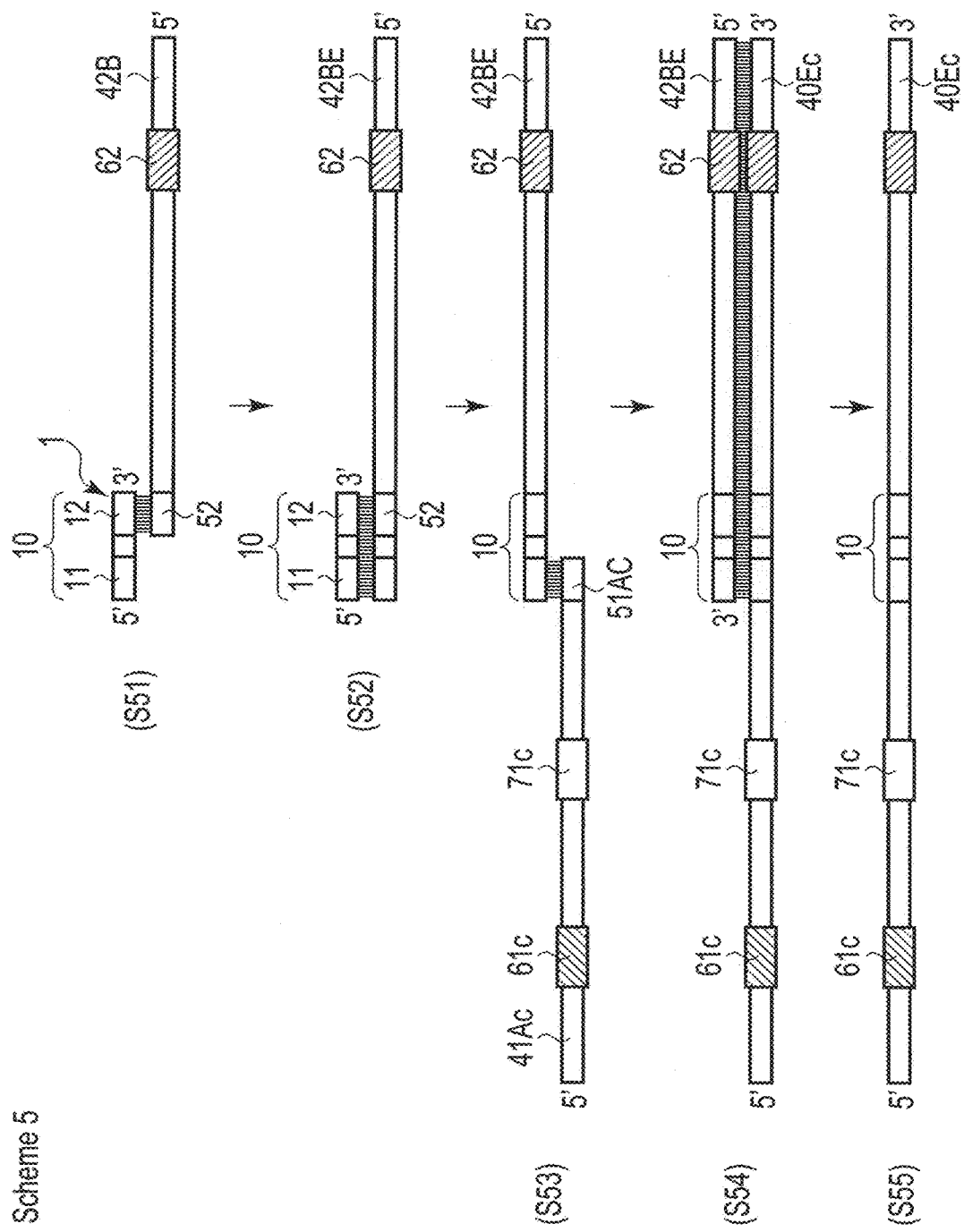
F I G. 7A

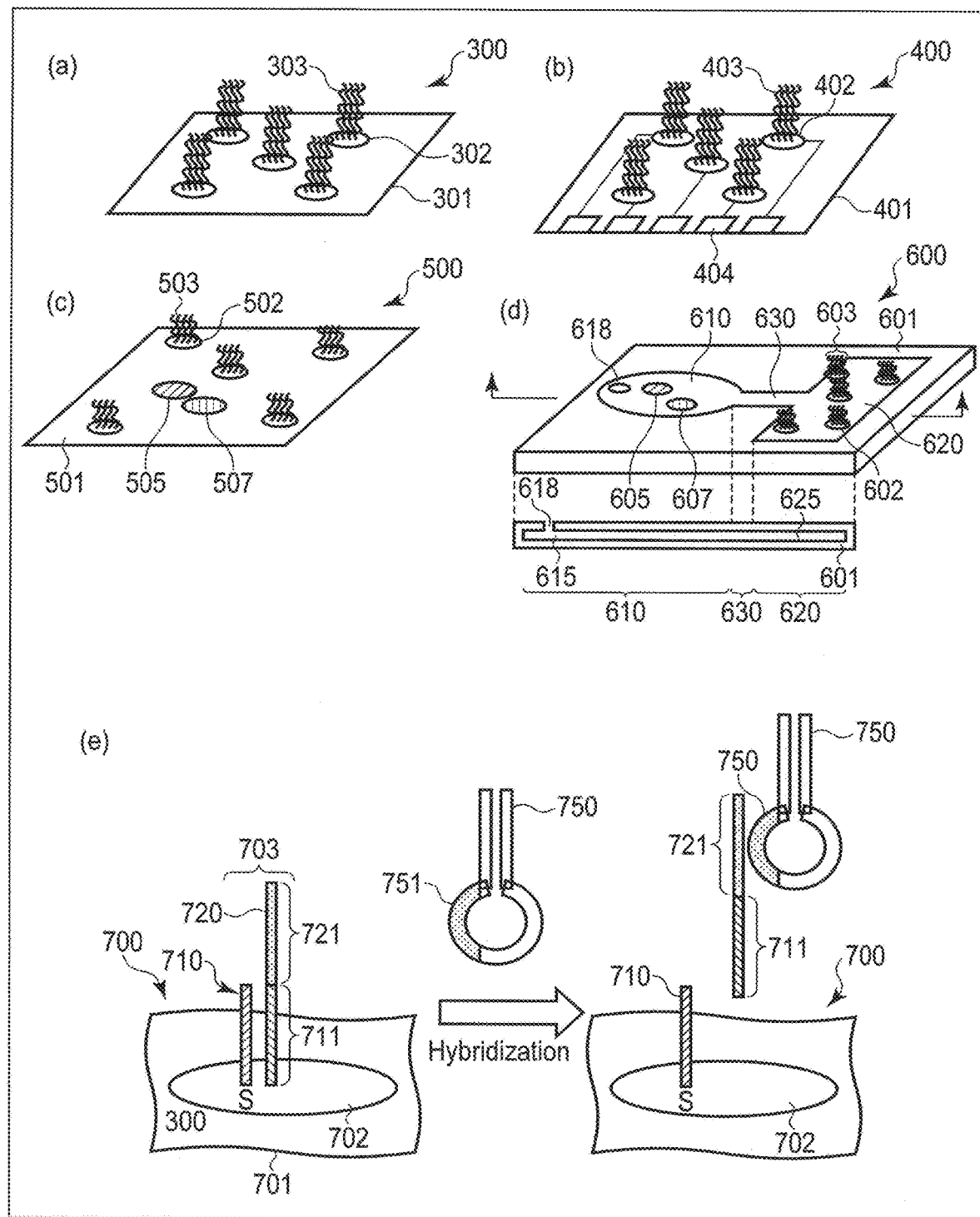
F I G. 8

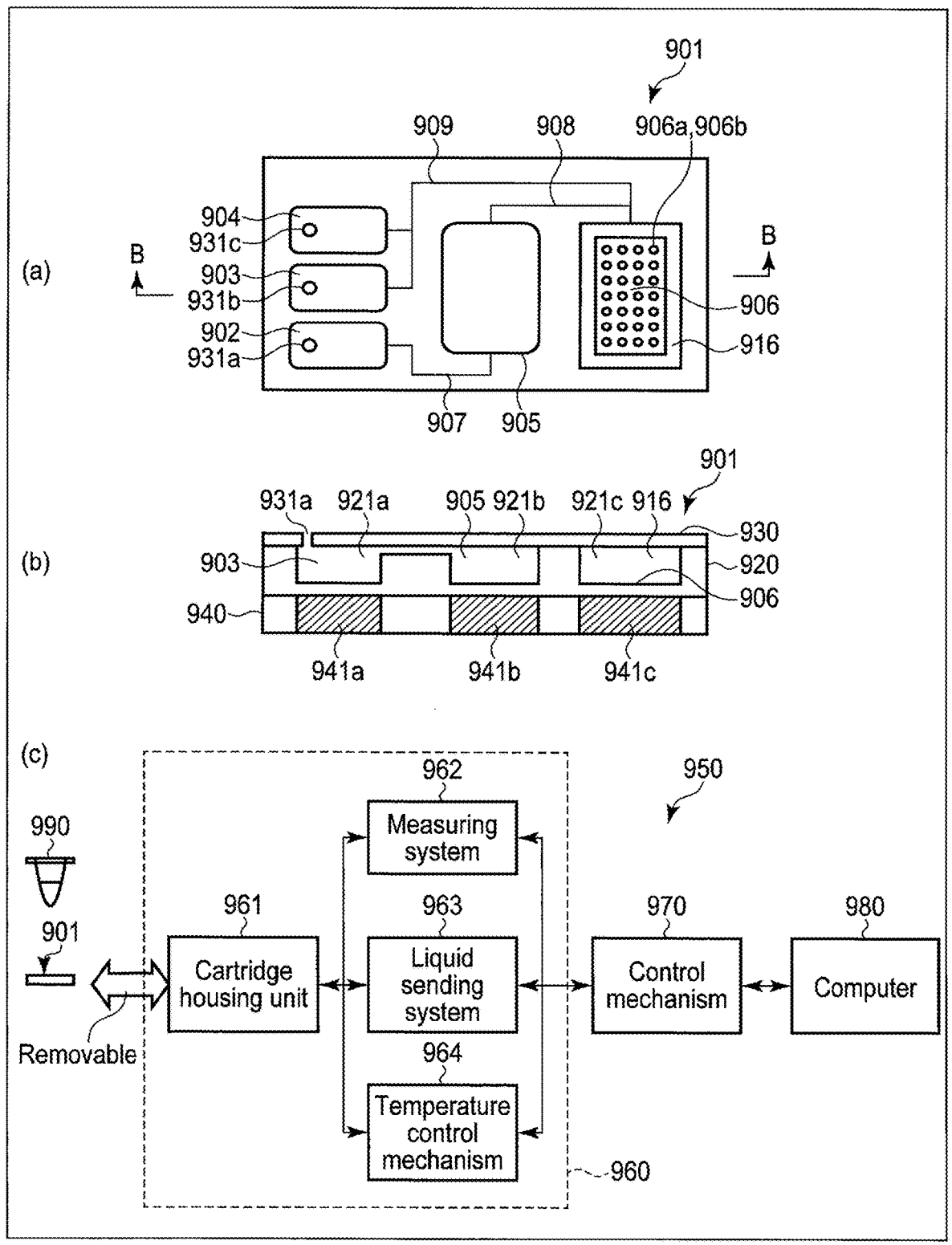
F I G. 9

Hinf I treatment of LAMP products

| Lane | Amplification template |
|---|---|
| 1 | Ligation PC |
| 2 | miRNA(+) ligation products |
| 3 | miRNA(−) ligation products |
| 4 | Template(−) |

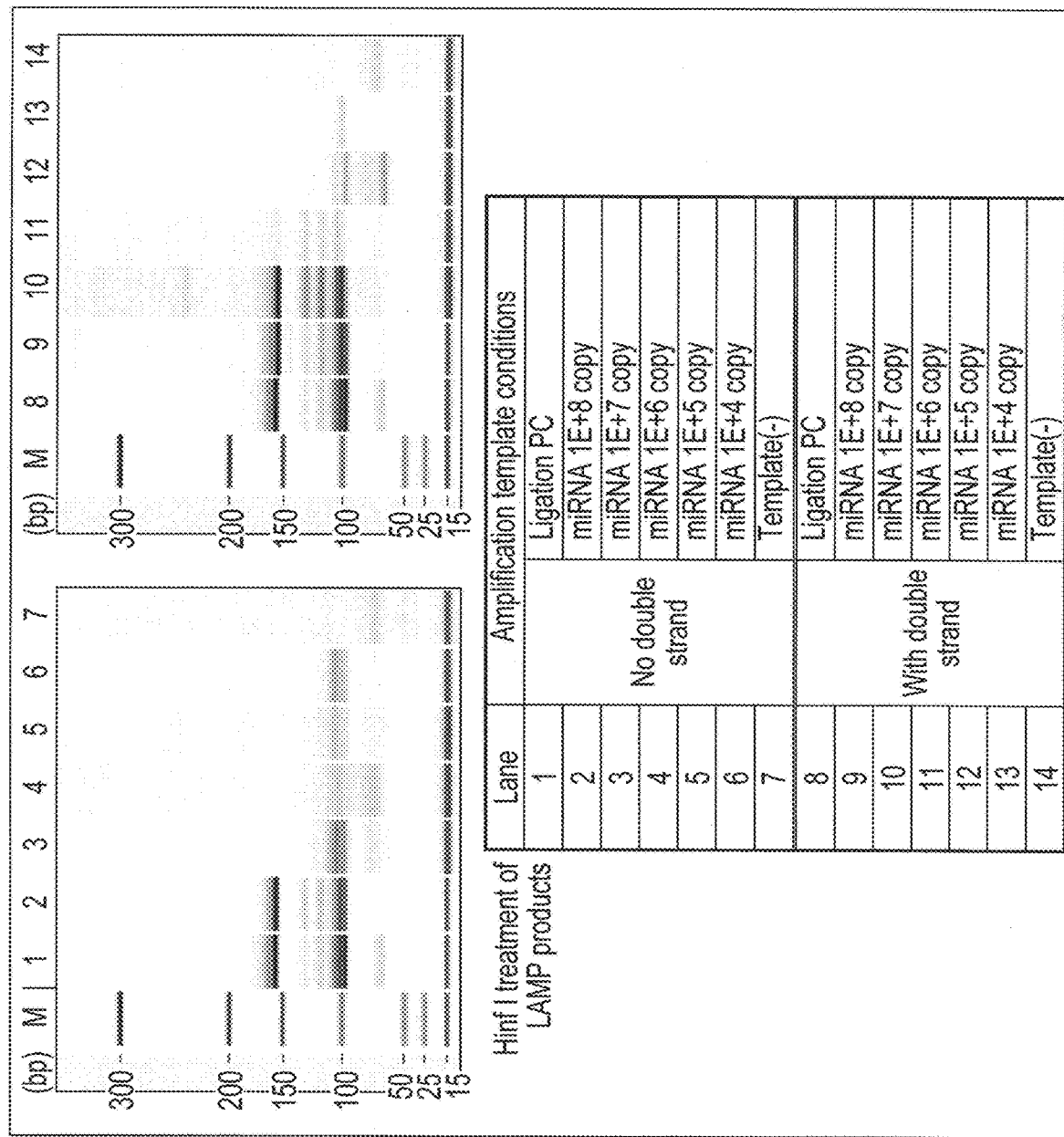
F I G. 15

METHOD FOR DETECTING A PLURALITY OF SHORT-CHAIN NUCLEIC ACID IN SAMPLE, COMBINATORIAL ANALYSIS KIT, ANALYSIS KIT SUPPLY MANAGEMENT METHOD

CROSS-REFERENCE TO RELATED APPLICATIONS

This application is a Continuation Application of PCT Application No. PCT/JP2016/058817, filed Mar. 18, 2016, the entire contents of which are incorporated herein by reference.

FIELD

Embodiments described herein relate generally to a method for detecting a plurality of short-chain nucleic acids in a sample, a combinatorial analysis kit, and an analysis kit supply management method.

BACKGROUND

Based on various studies in recent years, small RNA such as siRNA (small interference RNA) and miRNA (microRNA) have attracted attention. siRNA is double strand RNA with 21 to 23 bases, is artificially synthesized, and is used to inhibit gene expression. On the other hand, miRNA is a single strand RNA of 18 to 30 bases and exists in cells and it has been revealed that miRNA regulates gene expression. Particularly, many reports have been made on the relationship between various diseases including cancer and the types and expression levels of miRNA. Also, miRNA exists in serum in a form included in exosome. Thus, miRNA is much expected as a noninvasive diagnostic tool.

When such a short nucleic acid fragment is detected, the sequence itself to be detected is short and so a region where a primer for amplification is annealed cannot be secured, which makes amplification difficult, and as a result, it is difficult to improve the sensitivity.

BRIEF DESCRIPTION OF THE DRAWINGS

FIG. 1 is a flowchart showing an example of a detection method according an embodiment.

FIG. 4B is a diagram schematically showing an example of the chain-elongation nucleic acid set according to an embodiment.

FIG. 6A is a diagram showing an example of elongation according to an embodiment.

FIG. 7A is a diagram showing an example of elongation according to an embodiment.

FIG. 8 is a diagram showing an example of a probe according to an embodiment.

FIG. 9 is a diagram showing an example of an integral-type device and a measuring apparatus according to an embodiment.

FIG. 15 is a diagram showing an experimental result.

DETAILED DESCRIPTION

Figure 2:
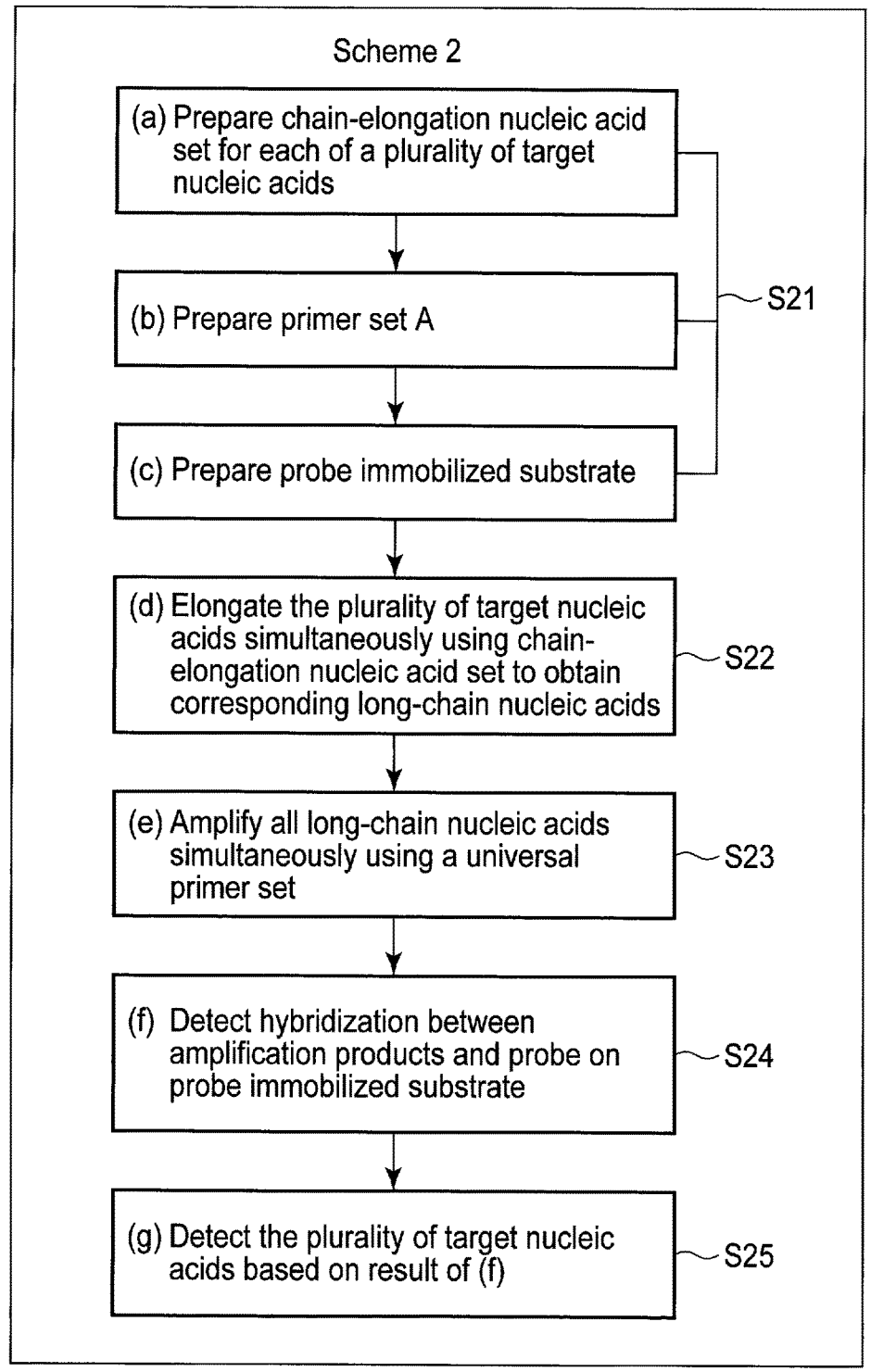
FIG. 2 is a flowchart showing an example of the detection method according an embodiment.

In general, according to one embodiment, a detection method is a method for detecting a plurality of target nucleic acids in a sample. Each of the plurality of target nucleic acids are short-chain nucleic acids respectively contain target sequences different from each other between the target nucleic acids. The target sequences containing a first sub-target sequence on a 5'-terminal side and a second sub-target sequence on a 3'-terminal side. The method includes (a) preparing a chain-elongation nucleic acid set group to obtain a long-chain nucleic acid for each target nucleic acid, a primer set that amplifies a plurality of long-chain nucleic acids in common, and a probe immobilized substrate, (b) obtaining the target nucleic acid or its complementary sequence and a long-chain nucleic acid group containing a first sub-chain-elongation nucleic acid corresponding thereto and a second sub-chain-elongation nucleic acid corresponding thereto, (c) obtaining an amplification product group by maintaining the long-chain nucleic acid group and the primer set under amplification conditions, (d) detecting presence/absence and/or an amount of hybridization between the amplification product group and a first probe, and (e) detecting, based on a result, the plurality of target nucleic acids.

Hereinafter, various embodiments will be described with reference to the drawings. The same reference signs are attached to common components throughout the embodiments, and duplicate descriptions are omitted. Each diagram is a schematic diagram of an embodiment to promote an understanding of the embodiment and the shape, dimensions, and ratios thereof may be different from actual ones and the design of these can appropriately be changed in consideration of the description that follows and publicly known technology.

1. Multiplex Detection Method of Short-Chain Nucleic Acid

A multiplex detection method of a short-chain nucleic acid according to one embodiment detects a plurality of short-chain nucleic acids in a sample as one series made of a plurality of target nucleic acids within the same period. In this method, a plurality of reactions occurs in multiplex form. That is, two or more reaction objects, for example, target nucleic acids, such as genes are brought into one reaction field. While these coexist, these are brought under a common reaction condition and maintained. Accordingly, a reaction common to a plurality of nucleic acids fitting the condition is caused. Thereby a plurality of target nucleic acids are detected as one series. "Within the same period" may be interpreted as, for example, simultaneously, sequentially, or in parallel.

According to the method, a plurality of short-chain nucleic acids defined as target nucleic acids in advance is treated in the same reaction field, for example, in one container. The method includes elongating the chain of a plurality of short-chain nucleic acids in multiplex form, amplifying a plurality of obtained long-chain nucleic acids in multiplex form, and detecting amplification products in multiplex form.

Hereinafter, a detection method according to an embodiment will be described with reference to FIGS. 1 and 2. First, a plurality of short-chain nucleic acids to be detected as one series is selected as target nucleic acids by the method.

The target nucleic acid to be detected in an embodiment is a short-chain nucleic acid whose chain is relatively short and which is a sequence to be a target (that is, a target sequence) and may be generally a nucleic acid shorter than 50 bases. Examples of the target nucleic acid include siRNA, miRNA, and a long nucleic acid, for example, nucleic acid fragments generated after a nucleic acid of the length of 50 bases or longer being fragmented. The target sequence means a nucleotide sequence to be detected. Such a target nucleic acid is an analyte to be detected by the method according to an embodiment.

For example, an example of a plurality of short-chain nucleic acids to be detected as one series may be a plurality of miRNA related by a specific disease, for example, cancer such as breast cancer, colon cancer, or lung cancer as a common theme. Also, for example, a plurality of target nucleic acids that may be included in one series may select to be a gene acting as an index of a specific disease as a common theme. A plurality of target nucleic acids that may be included in one series may be associated by a common theme, that is, information, for example, information about health conditions such as a specific ailment, disease, or disorder, but the present embodiment is not limited to such an example.

Throughout this specification, the term "nucleic acid" collectively indicates materials the structure of a portion thereof can be represented by a base sequence such as DNA, RNA, PNA, LNA, S-oligo, and methylphosphonate-oligo. For example, the nucleic acid may be naturally derived DNA or RNA, an artificial nucleic acid that is partially or completely artificially synthesized and/or designed, or a mixture thereof.

A sample may be an object to be analyzed that can contain an analysis object and may be an object that may contain a short-chain nucleic acid. The sample is preferably in a state in which an amplification reaction and/or a hybridization reaction are not prevented. For example, to use a material obtained from a living body as a sample according to the present embodiment, the material may be pretreated by some known means. For example, the sample may be a liquid. The sample may be, for example, a biological material such as blood, serum, leukocyte, urine, feces, semen, saliva, tissues, biopsy, oral mucosa, cultured cells, phlegm, lymph, sweat, cerebrospinal fluid, lacrimal fluid, mother milk, and amniotic fluid, an environmental material gathered from the environment, or a mixture thereof. Alternatively, one of these materials may be gathered from a living body or the environment as a sample material and a nucleic acid may be extracted by some means to use a liquid containing obtained nucleic acid components as a sample.

For example, a sample containing a target nucleic acid is prepared as described below. For example, a sample material is gathered. Then, the sample material is treated such as centrifuged, deposited, extracted and/or separated to obtain a sample in a state appropriate for amplification and hybridization of nucleic acid. If the sample material is in a state appropriate for amplification and hybridization of nucleic acid directly, the gathered sample material may be used as a sample.

For example, though not limited to the following kits, a nucleic acid can be extracted by using commercially available nucleic acid extraction kit. The kit is, for example, PureLink (registered trademark) miRNA Isolation Kit (manufactured by Thermo Fisher Scientific K.K.), microRNA Extractor (registered trademark) SP Kit (manufactured by Wako Pure Chemical Industries, Ltd.), NucleoSpin (registered trademark) miRNA (manufactured by Takara Bio Inc.), mirpremier (registered trademark) microRNA Isolarion Kit (manufactured by Sigma-Aldrich), High-pure miRNA Isolation Kit (manufactured by Roche Lifescience), or PAXgene Blood miRNA Kit (manufactured by Qiagen). Alternatively, without using such kits, for example, a sample material may be thermally treated at 80° C. to 100° C. after being diluted with a buffer solution and then, centrifuged to obtain a sample by gathering a supernatant thereof.

An example of a plurality of target nucleic acids contained in one series is shown in (S1) of Scheme 1 in FIG. 1. This example is a target nucleic acid 1 (1A, 1B, 1C, 1D, 1E). These target nucleic acids contain target sequences 10 (10A, 10B, 10C, 10D, 10E) respectively. These sequences have sequences of mutually different types and lengths thereof may be identical to each other or different from each other (S1).

The target nucleic acid 1 contains the target sequence 10. The target sequence 10 contains a first sub-target sequence 11 at the 5'-terminal and a second sub-target sequence 12 at the 3'-terminal. For example, the target sequence 10 may be made of the first sub-target sequence 11 at the 5'-terminal and the second sub-target sequence 12 at the 3'-terminal or may contain other additional sequences. If an additional sequence is contained, the additional sequence may exist between the first sub-target sequence 11 and the second sub-target sequence 12 or on the 5'-terminal side from the first sub-target sequence 11 and/or on the 3'-terminal side from the second sub-target sequence 12. In addition, a portion of the first sub-target sequence 11 and a portion of the second sub-target sequence 12 may overlap with each other on the target sequence 10. The length of such an overlapping portion may be, for example, 1 to 4 bases. The length of the first sub-target sequence 11 and that of the second sub-target sequence 12 may be identical to each other or different from each other. For example, the first sub-target sequence 11 and the second sub-target sequence 12 may have the numbers of bases that divide the target sequence 10 into roughly equal halves or have the lengths causing, for example, a small mutual Tm difference, but the present embodiment is not limited to the above examples.

For example, the target sequence 10 may have the length of the total length of the target nucleic acid 1 or the length of a partial sequence thereof, but may generally have the length shorter than 50 bases. For example, the first sub-target sequence 11 and the second sub-target sequence 12 may each have the length of 2 bases or more and 55 bases or less, for example, 5 bases or more and 50 bases or less, 10 bases or more and 35 bases or less, or 12 bases or more and 28 bases or less, but the present embodiment is not limited to the above values.

The chain of the target nucleic acid 10 is elongated by using a chain-elongation nucleic acid set 40. The chain-elongation nucleic acid set 40 contains a first sub-chain-elongation nucleic acid 41 and a second sub-chain-elongation nucleic acid 42. For all target sequences contained in one series, one chain-elongation nucleic acid set 40 specific to each target sequence is prepared.

The first sub-chain-elongation nucleic acid 41 contains a first target binding region 51 at one terminal. This may be the same sequence as the first sub-target sequence 11 or a first complementary sequence that is complementary thereto. The first sub-chain-elongation nucleic acid 41 contains a first amplification region 61 at another terminal and may contain a first detection region 71 between the first target binding region 51 and the first amplification region 61 (S1). Alternatively, a region in which the first detection region 71 is arranged may be, without containing the first target binding region 51, a range from bases adjacent thereto to a region overlapping with the first amplification region 61. The first detection region 71 extends, even when overlapping with the first amplification region 61, to a region that is not contained in the first amplification region 61. A further sequence may be contained outside the first amplification region 61 or not.

The second sub-chain-elongation nucleic acid 42 contains a second target binding region 52 at the 3'-terminal. This may be a second complementary sequence that is complementary to the second sub-target sequence 12. The second sub-chain-elongation nucleic acid 42 contains a second amplification region 62 on the 5'-terminal side (S1). A further sequence from the second amplification region 62 on the 5'-terminal side may exist or not.

One detection region 71 is allocated to each of all the target nucleic acids 1 contained in one series. All the detection regions 71 prepared for one series have different sequences from each other. In (S1) of FIG. 1, the target nucleic acid 1 (1A, 1B, 1C, 1D, 1E) is shown as an example. Each of the target nucleic acid 1 (1A, 1B, 1C, 1D, 1E) is associated with the detection regions 71 (71A, 71B, 71C, 71D, 71E) respectively. When the chain of the target nucleic acid 1 is elongated, the obtained long-chain nucleic acid can be identified by a detection region specific to allocated particular target nucleic acid being incorporated.

Though details of chain elongation will be described below, a long-chain nucleic acid as described below is obtained depending on the presence of each of the target nucleic acids 1. A long-chain nucleic acid 95 contains sequences derived from the first sub-chain-elongation nucleic acid 41 and the second sub-chain-elongation nucleic acid 42 in a direction in which the first target binding region 51 and the second target binding region 52 are opposed along the first sub-target sequence 11 and the second sub-target sequence 12 on a corresponding target sequence 10. That is, a sequence of the first sub-chain-elongation nucleic acid 41 or its complementary sequence and a sequence of the second sub-chain-elongation nucleic acid 42 or its complementary sequence are contained (S2).

The first amplification region 61 and the second amplification region 62 are sequences for one primer set that cooperate to amplify a nucleic acid chain using the long-chain nucleic acid 95 as a template (S2). The sequence of the first amplification region 61 is common in one series, and similarly, the sequence of the second amplification region 62 is common in one series. That is, a plurality of long-chain nucleic acids 95 formed by multiplex chain elongation in one series is amplified in common by one primer set. In other words, a plurality of long-chain nucleic acids obtained corresponding to one series is different for each target nucleic acid, but all long-chain nucleic acids have an amplification region constructed of the same sequence and thus, the plurality of long-chain nucleic acids can be amplified in common, that is, multiplex-amplified (S3).

The primer set used for amplification reaction is a universal primer set constructed to amplify all types of the long-chain nucleic acid 95 contained in one series. This contains at least a first primer corresponding to the first amplification region 61 and a second primer corresponding to the second amplification region 62.

Here, "amplification" means reproducing a template nucleic acid continuously using a primer set. In an embodiment, the amplification method that may be used is any known amplification method that amplifies the target nucleic acid using a primer set. The amplification method may be a poikilothermal amplification method or an isothermal amplification method and may be, for example, PCR, LAMP, RT-LAMP, SMAP, RCA, or ICAN, though not limited to the above examples. If desired, a reverse transcription reaction may be carried out in a pre-stage or in the same period of the amplification reaction.

The type of the primer set may be selected depending on the type of the amplification reaction to be used. For example, a primer set for PCR may contain, for example, a forward primer as the first primer and a reverse primer as the second primer. For example, a primer set for LAMP may contain, for example, an FIP primer and a BIP primer. Further, a primer set for LAMP may contain an F3 primer, a B3 primer, and/or a loop primer, that is, an LF primer and/or an LB primer. In that case, a sub-chain-elongation nucleic acid may further contain amplification regions corresponding to respective primers.

The length of an amplification region may be 10 to 35 bases and preferably 15 to 30 bases. The length of a detection region may be 5 to 50 bases, preferably 10 to 40 bases, and particularly preferably 15 to 35 bases.

The detection region and the amplification region may be selected from sequences that are different from those of nucleic acids that may be contained in a sample. Preferably, these sequences may be artificially designed nucleic acid sequences. If, for example, sequences present in the natural world are used as these sequences, a nucleic acid unintentionally mixed in a sample may also be amplified and detected. Accordingly, the result may be false positive. Such a nucleic acid that may unintentionally be mixed in a sample may be a nucleic acid of, for example, viruses, bacteria, yeast, plants and/or excluded animals. The occurrence of false positive can be inhibited by using artificially designed nucleic acid sequences as a detection region and an amplification region.

An artificial sequence can be produced, for example, as described below. For example, an artificial sequence can easily be produced by generating and allocating random numbers to A, G, C, and T. For example, produced artificial sequences may be checked whether to exist in the natural world by the BLAST search and thereby, an artificial sequence from which similar sequences are not searched may be selected. Artificial sequences are useful because sequences that are more efficient can freely be produced and selected as an amplification primer and a detection probe. Accordingly, sensitivity and precision of a detection system can be enhanced.

An amplification product 100 (100A, 100B, 100C, 100D, 100E) is obtained by the above amplification (FIG. 1(S3)). The amplification product 100 is detected by detecting hybridization of the detection region 71 and a probe. Hybridization is detected by a probe immobilized substrate 200. The probe immobilized substrate 200 includes a substrate 220 and a plurality of probes immobilized onto the substrate 220 (FIG. 1(S4)). A probe may contain a same sequence as that of a respective one detection region or its complementary sequence. The detection of hybridization is performed using probe immobilized substrate 200. The probe thereby hybridizes with the amplification product 100 containing the corresponding sequence. By detecting the hybridization, the presence or amount of presence of amplification products. The detection method thereby detects the presence or amount of presence of target nucleic acids in the sample.

The probe immobilized substrate may be interpreted, for example, in a narrow sense, as synonymous with terms such as "DNA chip", "nucleic acid chip", "micro array", and "DNA array" and these terms may interchangeably be used. In a broad sense, though described in detail below, a small probe immobilized substrate, for example, a DNA chip fixed by a further support, or for example, a device such as a detection cassette and a cartridge constructed by integrating other constituent members needed to construct an amplification reactor or a channel may also be interpreted as a probe immobilized substrate. All these modes may be provided as an embodiment.

In one embodiment, as shown in Scheme 2 in FIG. 2, the detection method includes the following procedure: preparing a chain-elongation nucleic acid group associated with target nucleic acids (or target sequences) in advance, a primer set, and a probe nucleic acid (S21); elongating the chain of a plurality of intended target nucleic acids sequence-specifically using these (S22); amplifying an obtained long-chain nucleic acid group non-specifically for target nucleic acid using the universal primer set (S23); detecting hybridization of a detection region in generated amplification products and the probe (S24); and detecting the plurality of target nucleic acids in the sample in the same period (S25).

In the above description, an example in which the first sub-chain-elongation nucleic acid 41 contains one amplification region 61 and one detection region 71 and the second sub-chain-elongation nucleic acid 42 contains one amplification region 62 is shown. However, the first sub-chain-elongation nucleic acid 41 and the second sub-chain-elongation nucleic acid 42 may further contain an additional amplification region.

In addition, the second sub-chain-elongation nucleic acid 42 may contain an additional detection region. In that case, a detection sequence 71 of the first sub-chain-elongation nucleic acid 41 exists as the first detection region 71 and the second sub-chain-elongation nucleic acid 42 may contain a second detection region. Alternatively, the second sub-chain-elongation nucleic acid 42 may contain a second detection region while the first sub-chain-elongation nucleic acid 41 does not contain the detection region 71.

In the second sub-chain-elongation nucleic acid 42, the detection region may be contained between the second target binding region 52 and the second amplification region 62. Alternatively, a region in which a second detection region 72 is arranged may be, without containing the second target binding region 52, a range from bases adjacent thereto to a region overlapping with the second amplification region 62. In addition, the second detection region 72 extends, even when overlapping with the second amplification region 62, to a region that is not contained in the second amplification region 62.

If, for example, the first and second sub-chain-elongation nucleic acids have the length of 50 bases or more, it is preferable to create double strands using the corresponding complementary chain for a portion or the entire portion on these chains excluding the target binding region. Accordingly, these nucleic acids are stabilized more. Thereby degradation of specificity, degradation of annealing efficiency, and non-specific reactions carried out by mismatches, for example, the occurrence of undesired annealing can be inhibited.

Also, the first target binding region and the second binding region contained in the first and second sub-chain-elongation nucleic acids may contain LNA (Locked Nucleic Acid) and/or PNA (Peptide Nucleic Acid). In this manner, binding to the sub-target sequence can be increased. Accordingly, stable chain elongation can be achieved and, as a result, the target nucleic acid can be detected with high accuracy.

By using such a detection method, a plurality of target nucleic acids in the sample can easily be detected at the same time.

Hereinafter, the method will be described more concretely. When "c" is attached immediately after the name, reference sign, or number of a specific sequence, "c" indicates a complementary sequence or complementary chain of the specific sequence.

2. Example of Chain-Elongation Nucleic Acid Set (1) First and Second Examples

Figure 3:
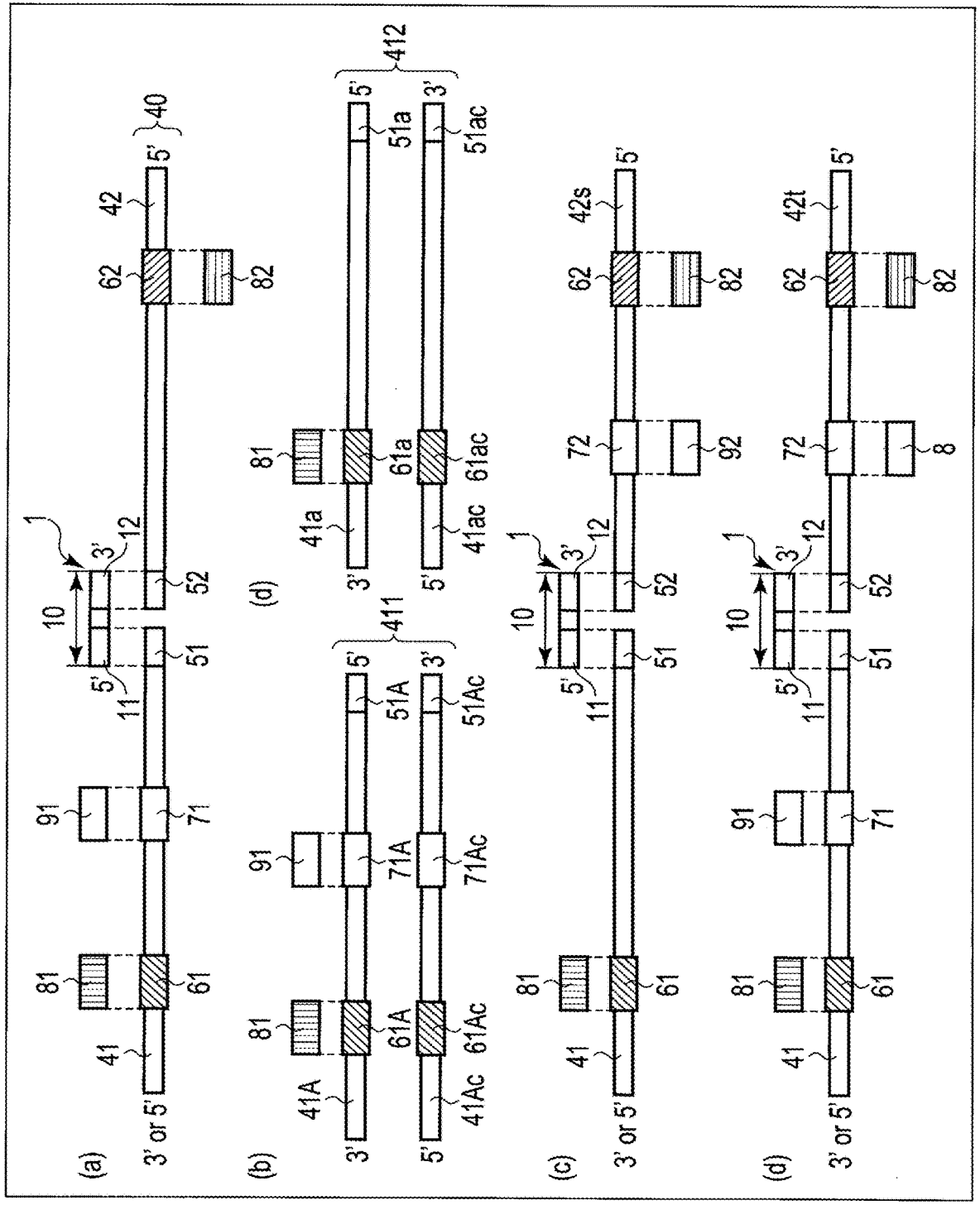
FIG. 3 is a diagram schematically showing an example of a chain-elongation nucleic acid set according to an embodiment.

The first sub-chain-elongation nucleic acid 41 of the chain-elongation nucleic acid set shown in (S1) of FIG. 1 will further be described using FIG. 3. The first sub-chain-elongation nucleic acid 41 shown in (S1) of FIG. 1 and part (a) of FIG. 3 may be a first sub-chain-elongation nucleic acid 41A or 41Ac shown in part (b) of FIG. 3. The first sub-chain-elongation nucleic acid 41A and the first sub-chain-elongation nucleic acid 41Ac are complementary chains to each other. To elongate the target nucleic acid 1 containing the target sequence 10, the chain-elongation nucleic acid set 40 may contain the first sub-chain-elongation nucleic acid 41A or 41Ac and the second sub-chain-elongation nucleic acid 42.

(1-1) First Example

The first sub-chain-elongation nucleic acid 41A contains a first target binding region 51A at the 5'-terminal. This is a complementary sequence of the first sub-target sequence 11. The first sub-chain-elongation nucleic acid 41A contains the first target binding region 51A, the first detection region 71A, and the first amplification region 61A in this order from the 5'-terminal and the 5'-terminal is phosphorylated.

(1-2) Second Example

The first sub-chain-elongation nucleic acid 41Ac contains a first target binding region 51Ac at the 3'-terminal. This is the same sequence as the first sub-target sequence 11. The first sub-chain-elongation nucleic acid 41Ac contains the first target binding region 51Ac, a first detection region 71Ac, and a first amplification region 61Ac in this order from the 3'-terminal.

(2) Third and Fourth Examples

Third and fourth examples are shown in part (c) and (d) of FIG. 3 respectively. The third example is an example in which the second sub-chain-elongation nucleic acid 42s contains the detection region 72 and the first sub-chain-elongation nucleic acid 42 does not contain the detection region 71. In the third example, a second sub-chain-elongation nucleic acid 42s contains the second target binding region 52, the second detection region 72, and the second amplification region 62 in this order from the 3'-terminal (S1). The fourth example is an example in which both of the first and second sub-chain-elongation nucleic acids contain a detection region.

(3) Fifth, Sixth, and Seventh Examples

Figure 4A:
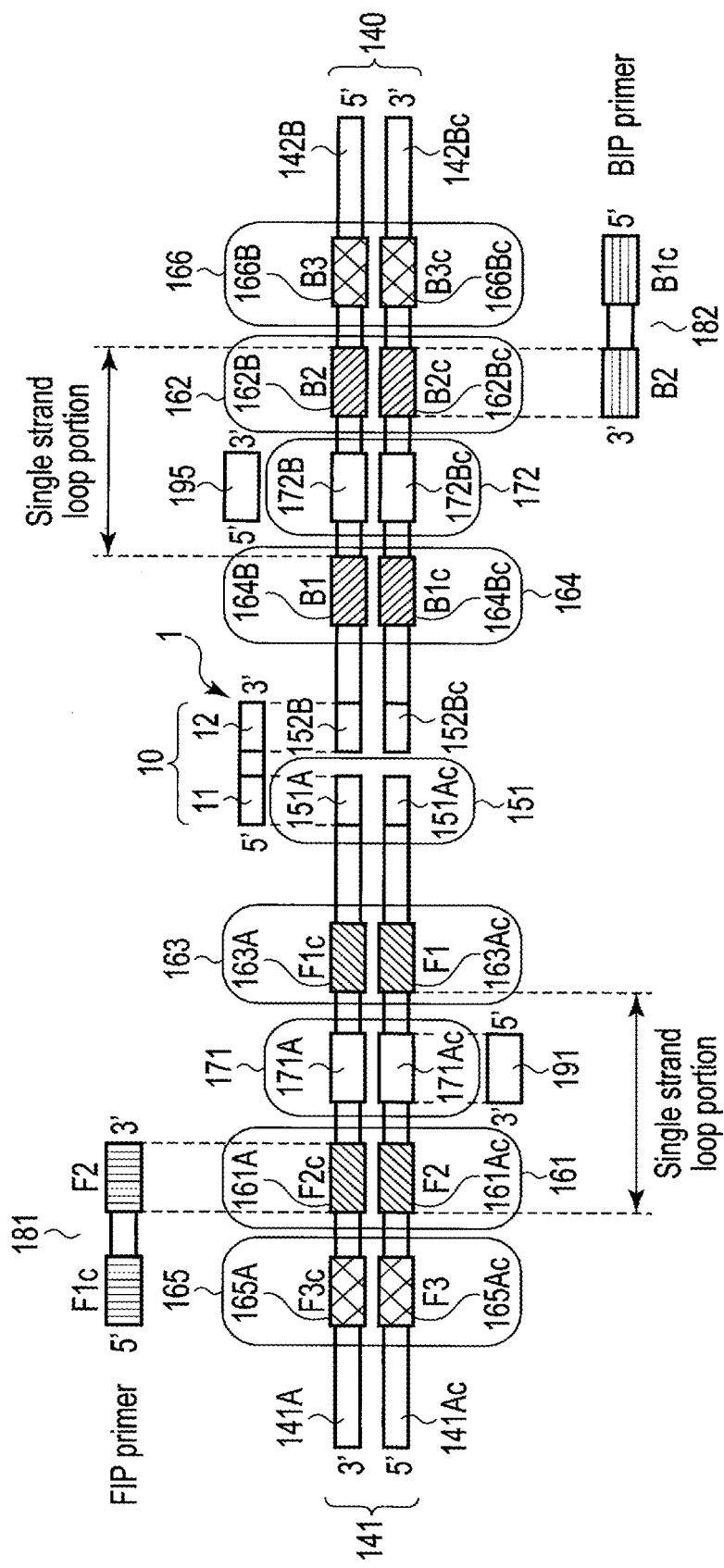
FIG. 4A is a diagram schematically showing an example of the chain-elongation nucleic acid set according to an embodiment.

An example of the chain-elongation nucleic acid set preferable for the isothermal amplification method such as LAMP will be described below as a fifth example with reference to FIGS. 4A and 4C. FIG. 4A shows an example of the mode in which a first sub-chain-elongation nucleic acid 141 and a second sub-chain-elongation nucleic acid 142 contain amplification regions and detection regions. However, the sub-chain-elongation nucleic acids 141, 142 do not necessarily need to contain all these amplification regions and detection regions and selection can be made as desired. Hereinafter, examples of combination will be described.

The fifth example of FIG. 4A is one of basic examples. In the fifth example, chain-elongation nucleic acid 140 contains the first sub-chain-elongation nucleic acid 141 and second sub-chain-elongation nucleic acid 142B. The first sub-chain-elongation nucleic acid 141 contains a first target binding region 151 at one terminal. This may be the same sequence as the first sub-target sequence 11 or a first complementary sequence that is complementary thereto. The first sub-chain-elongation nucleic acid 141 contains a first amplification region 161 at another terminal. Further, the first sub-chain-elongation nucleic acid 141 may contain the first target binding region 151, a primer binding region 163, a first detection region 171, and the first amplification region 161 in this order from one terminal side toward the another terminal of the first target binding region 151. On the other hand, the second sub-chain-elongation nucleic acid 142B contains a second target binding region 152B at the 3'-terminal. This may be a second complementary sequence that is complementary to the second sub-target sequence 12. The second sub-chain-elongation nucleic acid 142B contains a second amplification region 162B on the 5'-terminal side. The second sub-chain-elongation nucleic acid 142B may contain the second target binding region 152B, a primer binding region 164B, and the second amplification region 162B in this order from the 3'-terminal. Here, the primer binding region is a sequence having sequences corresponding to portions of an FIP primer and a BIP primer in the method such as LAMP and may also be called an amplification region or sequence.

Figure 4C:
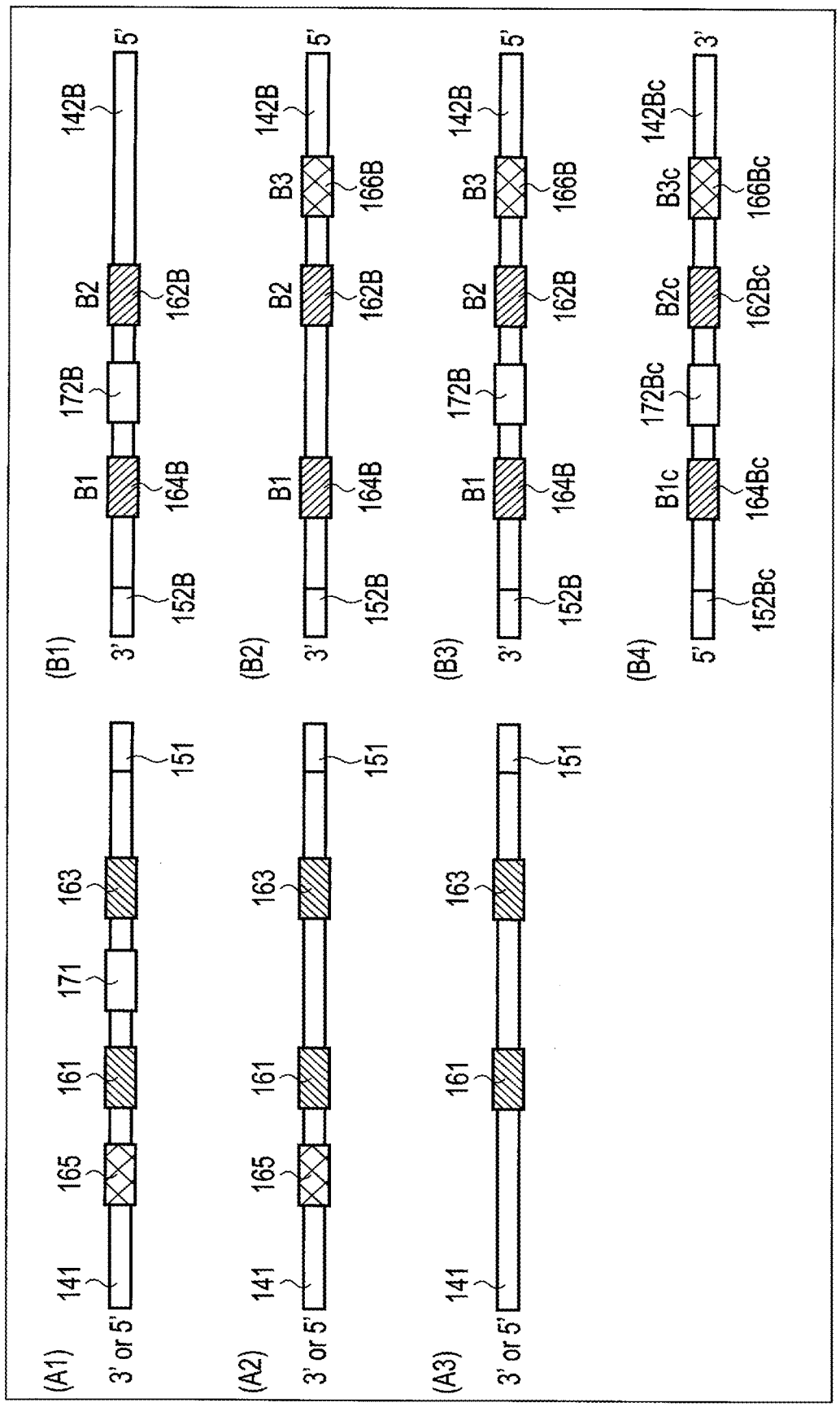
FIG. 4C is a diagram schematically showing an example of the chain-elongation nucleic acid set according to an embodiment.

Here, the first sub-chain-elongation nucleic acid 141 may further contain a third amplification region 165 further at another terminal from the first amplification region 161 ((A1) or (A2) of FIG. 4C). Similarly, the second sub-chain-elongation nucleic acid 142B may further contain a fourth amplification region 166B further on the 5'-terminal side from the second amplification region 162B ((B2) or (B3) of FIG. 4C). Also, the second sub-chain-elongation nucleic acid 142B may contain a detection region 172B between the second amplification region 162B and the second primer binding region 164B ((B1) or (B3) of FIG. 4C). In this case, the first sub-chain-elongation nucleic acid 141 may or may not contain the first detection region 171 ((A2) or (A3) of FIG. 4C). Also, the first sub-chain-elongation nucleic acid 141 may contain a fifth amplification region between the first primer binding region 163 and the first amplification region 161 (for example, instead of 171 in the position of 171 or in addition to 171). Similarly, the second sub-chain-elongation nucleic acid 142B may contain a sixth amplification region (for example, reference sign 172B ((B1) of FIG. 4)) between the second primer binding region 164B and the second amplification region 162B. In this case, the fifth (or the sixth) amplification region may be present in a region between the first (or the second) amplification region 161 (or 162B) and the first (or the second) primer binding region 163 (or 164B), containing a region in which the first (or the second) amplification region 161 (or 162B) is present, and not containing a region of the first (or the second) primer binding region 163 (or 164B). The region becomes a single strand loop region formed by intramolecular bonding in amplification products formed later. The first detection region 171, the second detection region 172B, the fifth amplification region (for example, 171), and the sixth amplification region (for example, 172B) are contained in such a single strand loop region. The fifth and sixth amplification regions may be regions generally corresponding to a loop primer. The first detection region 171 or the second detection region 172B may be arranged by substituting the fifth amplification region 171 or the sixth amplification region 172B so that a detection region is included in at least one of the first sub-chain-elongation nucleic acid 141 and the second sub-chain-elongation nucleic acid 142B and a detection region and an amplification region may both be contained in the region. When both regions are made to coexist, both regions do not overlap completely because the detection region is specific to the target sequence and the amplification region is non-specific to the target sequence.

In sub-chain-elongation nucleic acid, the target nucleic acid binding region, amplification region, detection region, and primer binding region may directly be connected to each other and a sequence that does not cause undesired non-specific hybridization may be present therebetween. For example, the above artificial sequence may be contained. In addition, the primer binding region may be designed in the same manner as the amplification region and the detection region described above. These sequences preferably have 20 bases or less, but the present embodiment is not limited to such a value.

Figure 5:
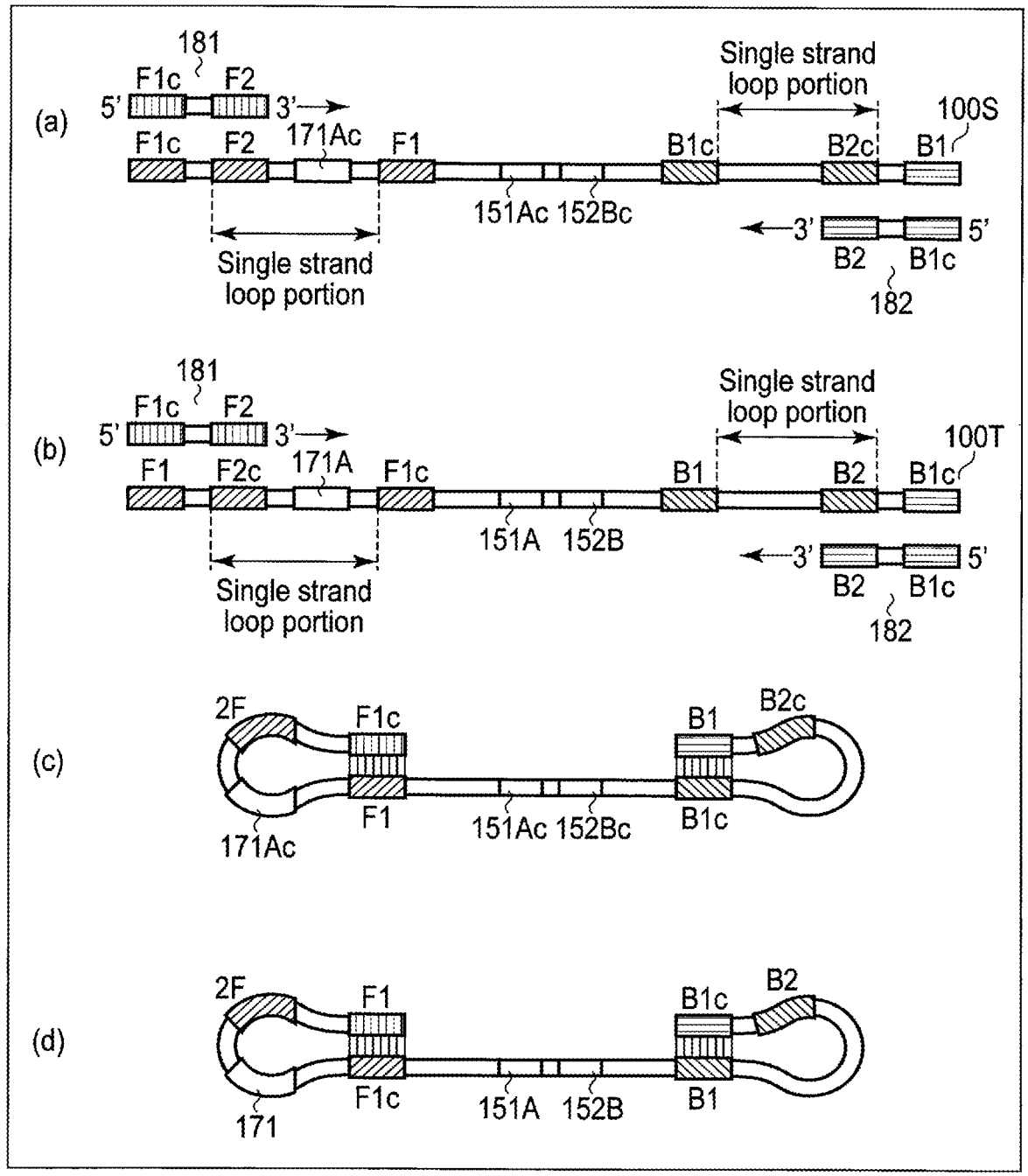
FIG. 5 is a diagram showing an example of long-chain nucleic acid formed in an embodiment.

In part (a) and (b) of FIG. 5, examples of amplification products obtained by amplifying a long-chain nucleic acid obtained by using the chain-elongation nucleic acid set 40 in the fifth example are shown. A first primer 181 corresponds to the amplification region of the first sub-chain-elongation nucleic acid 141 and is an FIP primer having, for example, an F1c sequence on the 5'-terminal side and an F2 sequence on the 3'-terminal side. A second primer corresponds to the amplification region of the second sub-chain-elongation nucleic acid 142 and is a BIP primer having, for example, a B1c sequence on the 5'-terminal side and a B2 sequence on the 3'-terminal side. An amplification product 100S may contain an F1c sequence, an F2 sequence, a detection region 171Ac, an F1 sequence, a B1c sequence, a B2c sequence, and a B1 sequence in this order from one terminal toward the another terminal (a). An amplification product 100T may contain an F1 sequence, an F2c sequence, a detection region 171A, an F1c sequence, a B1 sequence, a B2 sequence, and a B1c sequence in this order from one terminal toward the another terminal. Such amplification products form, for example, space structures shown in part (c) and (d) of FIG. 5 by intramolecular bonding. In this example, intramolecular bonding may be formed between the F1c sequence and the F1 sequence and also between the B1 sequence and the B1c sequence at another terminal.

A sixth example is shown in part (a) of FIG. 4B. Here, the chain-elongation nucleic acid 140 contains a first sub-chain-elongation nucleic acid 141A and a sub-chain-elongation nucleic acid configured in the same manner as the second sub-chain-elongation nucleic acid 142B shown in the fifth example.

The first sub-chain-elongation nucleic acid 141A contains a first target binding region 151A, a first primer binding region 163A, the first detection region 171A, and a first amplification region 161A in this order from the 5'-terminal and the 5'-terminal is phosphorylated. Here, the first target binding region 151A is a complementary sequence of the first sub-target sequence 11.

A seventh example is shown in part (b) of FIG. 4B. Here, the chain-elongation nucleic acid 140 contains a first sub-chain-elongation nucleic acid 141Ac and a sub-chain-elongation nucleic acid configured in the same manner as the second sub-chain-elongation nucleic acid 142B shown in the fifth example.

The first sub-chain-elongation nucleic acid 141Ac contains a first target binding region 151Ac, a first primer binding region 163Ac, the first detection region 171Ac, and a first amplification region 161Ac in this order from the 3'-terminal. Here, the first target binding region 151Ac is a same sequence of the first sub-target sequence 11.

In the fifth to seventh examples described above, a region in which the first detection region 171 (171A, 171Ac) is arranged may be, without containing the first target binding region 151 (151A, 151Ac), a range from bases adjacent thereto to a region overlapping with the first amplification region 161 (161A, 161Ac). The first detection region 171 (171A, 171Ac) extends, even when overlapping with the first amplification region 161 (161A, 161Ac), to a region that is not contained in the first amplification region 161 (161A, 161Ac).

Due to amplification by LAMP, for example, the first amplification region 161 (161A, 161Ac) is an F2 binding region and the primer binding region 163 (163A, 163Ac) is an F1 binding region in the first sub-chain-elongation nucleic acid 141 (141A, 141Ac). Also, the amplification region 165 (165A, 165Ac) may be an F3 binding region and a loop primer binding region may be an LF binding region.

In the first sub-chain-elongation nucleic acid 141A, the first detection region 171A may be present on the 3'-terminal side from the 3'-terminal of the F1 binding region 163A and on the 5'-terminal side from the 3'-terminal of the F2 binding region 161A. A portion of the first detection region 171A may overlap with the sequence of the F2 binding region 161A and, even in that case, contains a sequence independent of the F2 binding region 161A.

In the first sub-chain-elongation nucleic acid 141Ac, the first detection region 171Ac may be present on the 5'-terminal side from the 5'-terminal of the F1 binding region 163Ac and on the 3'-terminal side from the 5'-terminal of the F2 binding region 161Ac. The first detection region 171Ac may be present, on the first sub-chain-elongation nucleic acid, between bases adjacent to the F1 binding region and a region overlapping with the F2 binding region Ac without containing the F1 binding region. A portion of the first detection region 171Ac may overlap with the sequence of the F2 binding region 161Ac and, even in that case, has a sequence independent of the F2 binding region 161Ac.

In the second sub-chain-elongation nucleic acid 142B, the second detection region 172B may be present between the second target binding region 152B and the second primer binding region 162B. The second detection region 172B may be present on the 5'-terminal side from the 5'-terminal of the second target binding region 152B and on the 3'-terminal side from the 5'-terminal of the second primer binding region 162B. The second detection region 172B extends, even when overlapping with the second primer binding region 162B, to a region that is not contained in the second primer binding region 162B.

In the above description, an example in which the second sub-chain-elongation nucleic acid 142B shown in FIG. 4A is used as the second sub-chain-elongation nucleic acid is shown. However, the sub-chain-elongation nucleic acid 142Bc shown in FIG. 4A can also be used as the second sub-chain-elongation nucleic acid. Also in that case, the relationship between corresponding components and the relationship to the first sub-chain-elongation nucleic acid correspond to the above relationships. Accompanying changes of the configuration of the first sub-chain-elongation nucleic acid and the like can easily and clearly be understood by persons skilled in the art based on the above descriptions. An example thereof is shown in (B4) of FIG. 4C. The second sub-chain-elongation nucleic acid 142Bc contains a second target binding region 52Bc at the 5'-terminal, a second primer binding region 162Bc at the 3'-terminal, and a third amplification region 172Bc therebetween and the 5'-terminal is phosphorylated. The third amplification region 172Bc may be replaced by a region in which an LB primer is bound. A further amplification region 166Bc may be contained on the extreme 3'-terminal side.

3. Chain Elongation by Chain-Elongation Nucleic Acid Set

The chain elongation of target nucleic acid using the above chain-elongation nucleic acid set may be carried out using one of two methods described below.

(3-1) Chain Elongation by Ligation

Figure 6B:
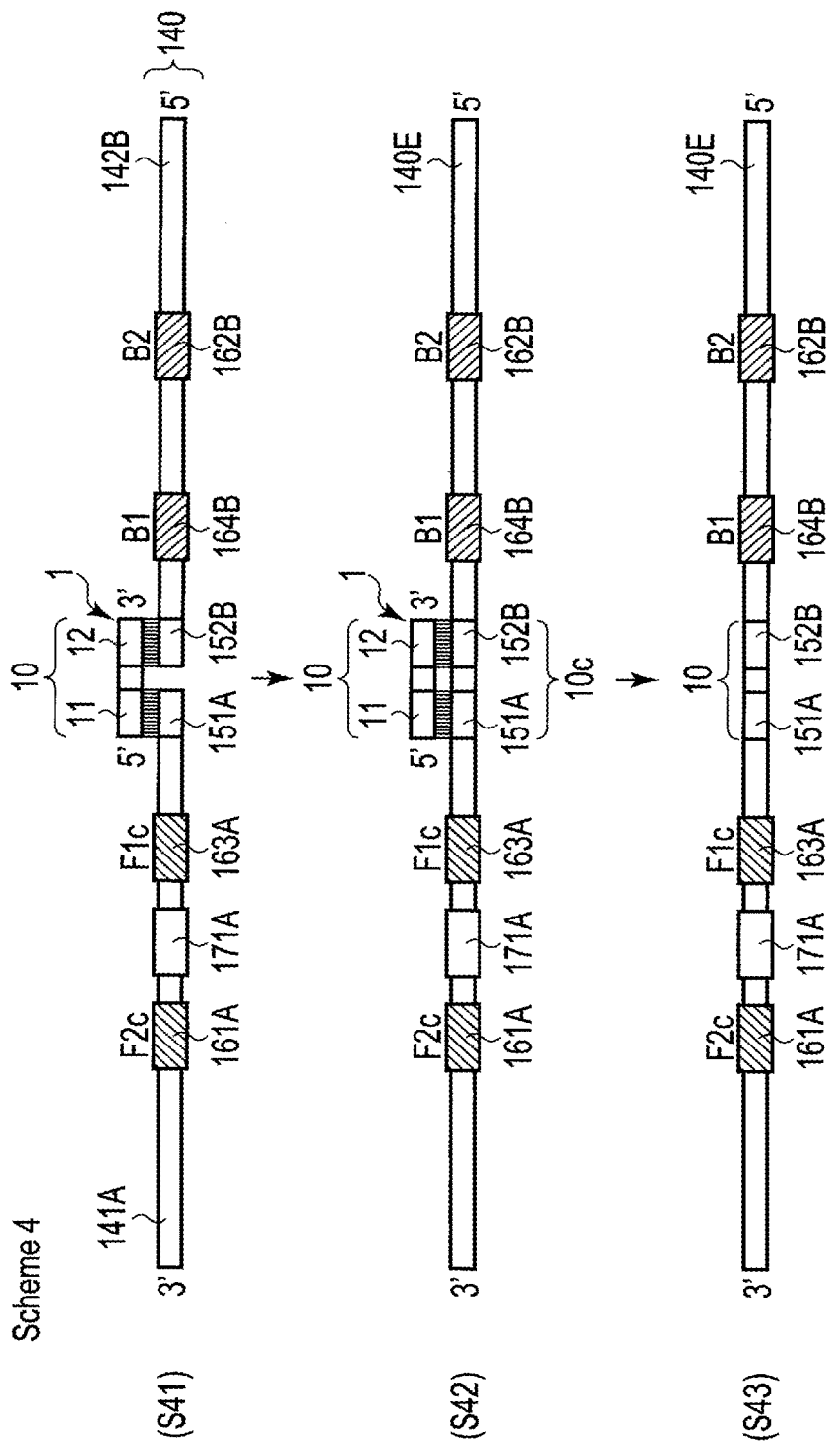
FIG. 6B is a diagram showing an example of elongation according to an embodiment.

A first method is shown in Scheme 3 of FIG. 6A and Scheme 4 of FIG. 6B. The first sub-chain-elongation nucleic acid used here is the first sub-chain-elongation nucleic acids 41A, 141A and these nucleic acids contain the first target binding regions 51A, 151A at the 5'-terminal respectively and the 5'-terminal is phosphorylated. The reaction of chain elongation proceeds, for example, like Scheme 3 including (S31) to (S33) or Scheme 4 including (S41) to (S43).

In this method, the first sub-chain-elongation nucleic acids 41A, 141A and the second sub-chain-elongation nucleic acids 42B, 142B are annealed first with respect to the target nucleic acid 1 (S31, S41). Next, the first sub-chain-elongation nucleic acids 41A, 141A and the second sub-chain-elongation nucleic acids 42B, 142B are linked by ligation to form long-chain nucleic acids 40E, 140E respectively (S32, S42). Next, the target nucleic acid 1 is liberated to obtain the long-chain nucleic acids 40E, 140E (S33, S43). The long-chain nucleic acids 40E, 140E contain a sequence of the first sub-chain-elongation nucleic acids 41A, 141A and a sequence of the second sub-chain-elongation nucleic acids 42B, 142B respectively and contain a complementary sequence 10c of the target sequence 10 overlapping portions of these sequences. In this manner, the chain elongation of target nucleic acid is achieved by obtaining the long-chain nucleic acids 40E, 140E including information about the target nucleic acid 1.

(3-2) Example of Chain Elongation Reaction by Ligation

The chain elongation reaction by ligation as described above is carried out, for example, as described below. A chain elongation reaction liquid is prepared by mixing a sample that can contain a target nucleic acid and a chain-elongation nucleic acid set. The reaction liquid is maintained at a temperature of Tm of the first sub-target sequence and the second sub-target sequence or lower. The chain-elongation nucleic acid set is thereby annealed with respect to the target nucleic acid. Next, ligase is added and the reaction liquid is maintained at a temperature near the active temperature thereof. Accordingly, nick portions present between the first sub-chain-elongation nucleic acid and the second sub-chain-elongation nucleic acid bound to the target nucleic acid via two sub-target sequences are linked. Accordingly, a long-chain nucleic acid is obtained.

Alternatively, the annealing and ligation may proceed in parallel. In that case, ligase may be brought into a reaction liquid for annealing.

Examples of ligase include, though not limited to these examples, for example, T4 RNA Ligase2, T4 DNA Ligase, SplintR ligase and the like. For example, T4 RNA Ligase2 can increase the efficiency of ligation by using chimera synthesis oligo DNA in which 2 bases or more at the 3'-terminal to be linked are RNA. See, for example, Molecular Cell, 2004, 16, 211. The reaction temperature may be generally 10 to 60° C., but may optionally be adjusted in accordance with the type of enzyme and whether a chain-elongation nucleic acid contains LNA or PNA. When, for example, a sub-chain-elongation nucleic acid into which LNA or PNA is introduced is used, the binding force to these sub-target sequences is strong and thus, a reaction can be carried out at a temperature higher than normal. Accordingly, specificity of annealing of the sub-chain-elongation nucleic acid to the target sequence is increased and, as a result, non-specific reactions can be inhibited. In that case, heat-resistant ligase is preferably used. A chain-elongation reagent used for chain elongation by ligation may contain ligase.

Thus, by treating a plurality of short-chain nucleic acids defined as the target nucleic acids in advance in the same reaction field as one series, a plurality of target sequences can be elongated in one reaction field, for example, in the same reaction container in the same period.

(3-3) Chain Elongation by Polymerase

Figure 7B:
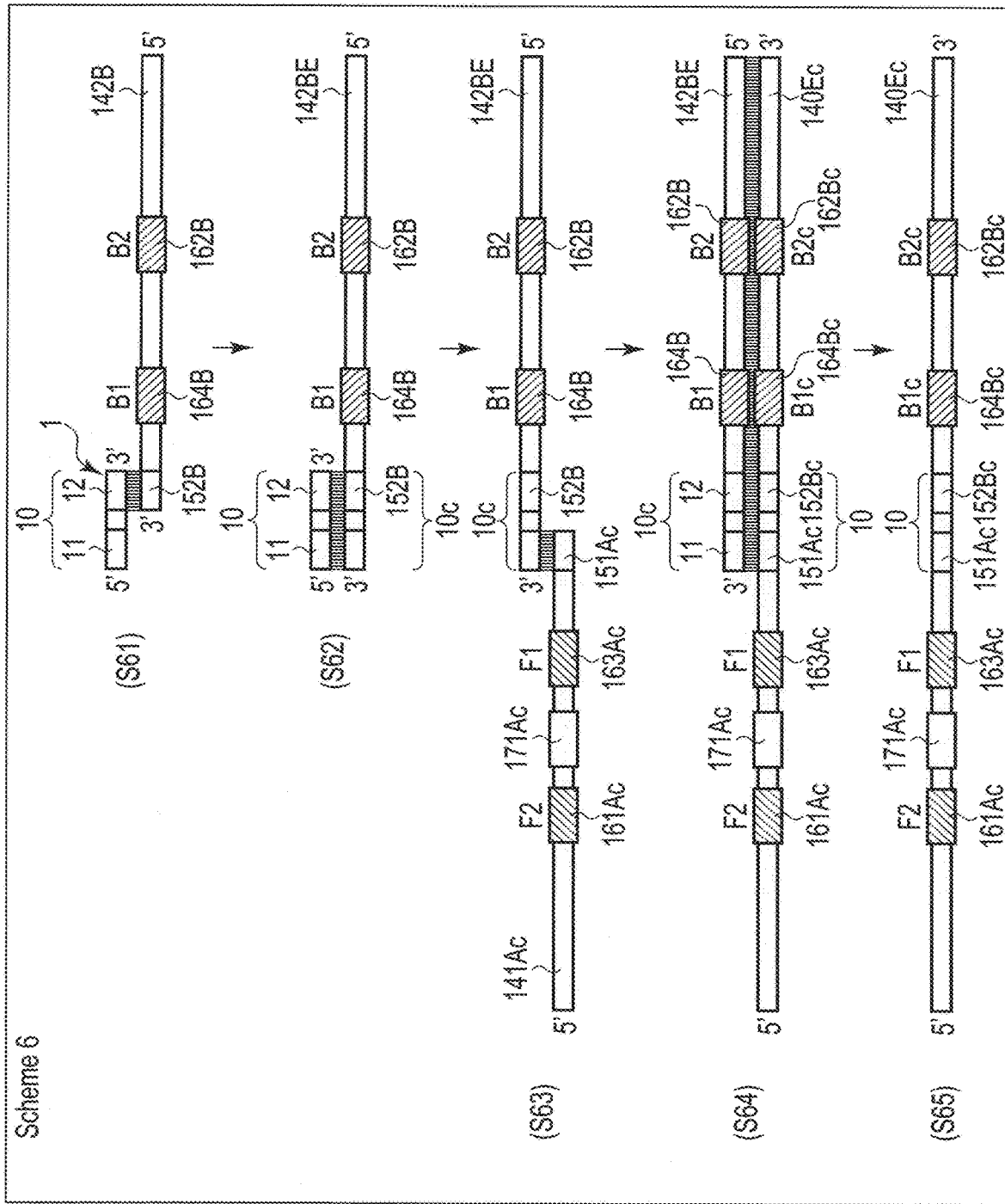
FIG. 7B is a diagram showing an example of elongation according to an embodiment.

A second method is shown in FIGS. 7A and 7B. The first sub-chain-elongation nucleic acid used here is the first sub-chain-elongation nucleic acids 41Ac, 141Ac, which contain the first target binding regions 51Ac, 151Ac at the 3'-terminal respectively. The reaction of this chain elongation proceeds, for example, like Scheme 5 including (S51) to (S55) or Scheme 6 including (S61) to (S65).

In this method, the second sub-chain-elongation nucleic acids 42B, 142B are annealed first with respect to the target nucleic acid 1 (S51, S61). Using the target nucleic acid 1 as a template, the second sub-chain-elongation nucleic acids 42B, 142B are extended in the direction of the 3'-terminal by DNA polymerase or reverse transcriptase (S52, S62). First extended chains 42BE, 142BE are thereby formed. The first chain-elongation nucleic acids 41Ac, 141Ac are annealed with respect to the first extended chains 42BE, 142BE formed (S53, S63). Using the first extended chains 42BE, 142BE as a template, the first sub-chain-elongation nucleic acids 41Ac, 141Ac are extended in the direction of the 3'-terminal (S54, S64). Second extended chains 40Ec, 140Ec are thereby formed. The second extended chains 40E, 140E are liberated from the first extended chains 42BE, 142BE. Accordingly, long-chain nucleic acids 40Ec, 140Ec are obtained.

The long-chain nucleic acids 40Ec, 140Ec contain a sequence of the first sub-chain-elongation nucleic acids 41Ac, 141Ac and the complementary sequence 42Bc, 142Bc of the second sub-chain-elongation nucleic acids 42B, 142B respectively and contain the same sequence as the target sequence 10 by overlapping portions of these sequences. In this manner, the chain elongation of target nucleic acid is achieved by obtaining the long-chain nucleic acids 40Ec, 140Ec including information about the target nucleic acid 1.

(3-4) Example of Chain Elongation by Polymerase

The chain elongation reaction by polymerase as described above is carried out by, for example, as described below. A first chain elongation reaction liquid is prepared by mixing a sample that can contain a target nucleic acid, a second sub-chain-elongation nucleic acid, and DNA polymerase. If the target nucleic acid is RNA, instead of DNA polymerase, reverse transcriptase is brought into the chain elongation reaction liquid. The first chain elongation reaction liquid is maintained at a temperature of Tm of the second sub-target sequence or lower. Accordingly, the second sub-target sequence and the second sub-chain-elongation nucleic acid are annealed. Next, a first extended chain is formed by DNA polymerase (or reverse transcriptase). By adding thereto a first sub-chain-elongation nucleic acid and DNA polymerase (or reverse transcriptase), a second chain elongation reaction liquid is prepared. The second chain elongation reaction liquid is maintained at a temperature of Tm of the first sub-target sequence or lower. Accordingly, the first sub-chain-elongation nucleic acid is annealed with respect to the first extended chain and the first extended chain is used as a template to extend the first sub-chain-elongation nucleic acid. Second extended chains are thereby formed.

Alternatively, a first sub-chain-elongation nucleic acid may be caused to coexist with the second sub-chain-elongation nucleic acid in the first chain elongation reaction liquid. In this case, extension of the first sub-chain-elongation nucleic acid and extension of the second sub-chain-elongation nucleic acid proceed simultaneously. That is, extensions in two directions occur simultaneously.

DNA polymerase or reverse transcriptase included in the first chain elongation reaction liquid and the second chain elongation reaction liquid may be enzymes identical to each other or different from each other. If enzymes included in the first chain elongation reaction liquid and the second chain elongation reaction liquid are different from each other, the difference may be, for example, temperature characteristics. The above example is an example in which a reaction is carried out by including an enzyme in the first chain elongation reaction liquid and then, an enzyme is added to the second chain elongation reaction liquid is shown. However, the present embodiment is not limited to the above example. For example, the first sub-chain-elongation nucleic acid and the second sub-chain-elongation nucleic acid may be elongated simultaneously and in that case, necessary enzymes and chain-elongation nucleic acids may coexist in one reaction field. When a first chain elongation reaction and a second chain elongation reaction are carried out by a two-stage reaction as described above, a first enzyme for the first chain elongation reaction and a second enzyme for the second chain elongation reaction may be brought during the first chain elongation reaction. A chain elongation reagent used for chain elongation by polymerase may contain polymerase or reverse transcriptase.

Examples of DNA polymerase include, though not limited to these examples, for example, Klenow Fragment (Large Fragment E. coli DNA polymerase I), T4 DNA polymerase, phi29 DNA polymerase, Bst DNA polymerase, Csa DNA polymerase, 96-7 DNA polymerase, Vent (registered trademark) (exo-)DNA polymerase, and GspSSD DNA polymerase. Alternatively, the enzyme may be reverse transcriptase such as M-MuLV Reverse Transcriptase or Transcriptor Reverse Transcriptase capable of using DNA as a template.

Examples of reverse transcriptase include, though not limited to these examples, for example, M-MuLV Reverse Transcriptase, AMV Reverse Transcriptase, Transcriptor Reverse Transcriptase, SuperScript (registered trademark) Transcriptor Reverse Transcriptase, and MultiScribe Reverse Transcriptase.

The reaction temperature may generally be, for example, 10° C. to 60° C. The reaction temperature may also be changed or adjusted in accordance with the type of enzyme to be used and the sequence of the sub-chain-elongation nucleic acid, for example, whether LNA or PNA is contained. When, for example, the sub-chain-elongation nucleic acid contains LNA or PNA, the binding force between the sub-chain-elongation nucleic acid and the target nucleic acid becomes strong and thus, a reaction can be carried out at a temperature higher than normal. Accordingly, specificity of annealing of the sub-chain-elongation nucleic acid to the target nucleic acid can be increased and, as a result, the occurrence of non-specific reactions can be inhibited. In such a case, it is preferable to use heat-resistant enzymes, for example, heat-resistant DNA polymerase and heat-resistant reverse transcriptase as the enzyme to be used.

Thus, by treating a plurality of short-chain nucleic acids defined as the target nucleic acids in advance in the same reaction field as one series, a plurality of target sequences can be elongated in one reaction field, for example, in the same reaction container in the same period.

4. Multiplex Amplification of Long-Chain Nucleic Acid

In the present method, as described above, all long-chain nucleic acids included in one series are amplified in one reaction field in the same period using a universal primer set. Amplification reaction conditions are determined in accordance with the amplification reaction to be selected and may be selected from generally used and publicly known enzymes and reaction conditions.

When LAMP is used, for example, amplification may be performed using Bst DNA polymerase, Csa DNA polymerase, 96-7 DNA polymerase, or GspSSD DNA polymerase used generally at constant temperature of 50° C. to 70° C. for 15 to 90 min. Reagents (amplification reagents) needed for amplification may include, for example, enzymes such as polymerase, substrates such as deoxynucleoside triphosphate (dNTPs) needed when a new polynucleotide chain starting from a primer, and when reverse transcription is performed simultaneously, enzymes such as reverse transcriptase, substrates needed therefor, and further buffers of salt to maintain an appropriate amplification environment. Also, thickeners may further be contained as an amplification reagent. Such amplification reagents may be provided by being included in an assay kit described below.

5. Detection of Amplification Products

An amplification product is detected by detecting hybridization of a detection region contained in the amplification product and a probe. By detecting an amplification product, a target nucleic acid in a sample is detected.

Here, "detection" may be the presence/absence of target nucleic acid and/or the quantification of target nucleic acid. Here, "probe" is a nucleic acid chain to detect an amplification product formed by a primer set and has a sequence that specifically binds to a detection region. For example, a probe may contains a sequence complementary to a respective one of the detection region or may contain the same sequence as the detection region.

The length of bases of a probe may be, though not limited to these examples, for example, in the range of 5 to 50 bases, preferably in the range of 10 to 40 bases, and particularly preferably in the range of 15 to 35 bases.

Hybridization is detected by using the principle to detect the presence/absence or the degree of hybridization of some known kind. For example, after causing amplification products and a probe to coexist under appropriate conditions a generated hybridization signal may be detected or determined. The hybridization signal may be an optical signal, a chemical signal, an electrochemical signal, a radioactive signal, or a combination thereof.

An amplification reaction and a hybridization reaction may proceed in the same period in the same reaction solution of the same reaction field and, in that case, these reactions may occur simultaneously, an amplification reaction and a hybridization reaction may occur continuously in parallel, or a hybridization reaction may occur after an amplification reaction. Alternatively, an amplification reaction and a hybridization reaction may continuously be caused in different reaction solutions of the same reaction field.

(5-1) Probe Immobilized Substrate

A probe may be provided in a state of being immobilized to the surface of a substrate. For example, a probe may be provided as a probe immobilized substrate including a substrate and a plurality of probes immobilized to a surface in contact with a first reaction field provided by the substrate. An example of the probe immobilized substrate is shown in FIG. 8.

Part (a) to (c) of FIG. 8 are plan views of the example of the probe immobilized substrate. A probe immobilized substrate 300 shown in part (a) of FIG. 8 includes a substrate 301, a plurality of probe immobilized regions 302 arranged on a top surface of the substrate 301 in an array, and a plurality of probes 303 immobilized to the probe immobilized region for each type. The probe immobilized substrate 300 as described above may be used when amplification products are detected based on the principle of measurement using an optical signal such as fluorescence and chemiluminescence. To detect hybridization of an amplification product and a probe, means such as a marker substance that recognizes a double strand before being bound thereto, binding of a marker substance to an amplification product using an antibody or secondary probe nucleic acid, and incorporation of a marker substance attached to dNTPs of an amplification product during amplification reaction may be used.

A probe immobilized substrate 400 shown in part (b) of FIG. 8 includes a substrate 401, a plurality of electrodes 402 as probe immobilized regions arranged on the top surface of the substrate 401 in an array, a plurality of probes 403 immobilized to the electrode 402 for each type, and a pad 404 electrically connected to the electrode 402. The probe immobilized substrate 400 as described above may be used to electrochemically detect hybridization. Such detection of hybridization may be achieved by using, for example, a double strand identification material such as an intercalator that identifies and binds a double strand formed by the probe 403 and an amplification product. A hybridization signal is detected as an electric signal and information transmitted as an electric signal may be fetched from the pad 404. The probe immobilized substrate 400 may further include a reference electrode and a counter electrode.

Examples of the double strand identification material include, for example, bis-intercalator such as Hoechst 33258, acridine orange, quinacrine, daunomycin, metallo-intercalator, and bisacridine, tris-intercalator, and poly-intercalator, which are known themselves as double strand identification materials and further, these double strand identification materials may further be modified by an electrochemically active metal complex such as ferrocene and viologen. Double strand identification materials are generally used in the concentration ranging from 1 ng/mL to 1 mg/mL, though the concentration is different depending on the type thereof. At this point, a buffer solution whose ionic strength is in the range of 0.001 to 5 and whose pH is in the range of 5 to 10 can be used. For example, such a double strand identification material may be an intercalating agent involved in generation of a hybridization signal. Such an intercalating agent may be included in an assay kit as a hybridization reagent.

For the measurement, for example, a potential at which a double strand identification material reacts electrochemically or higher is applied and a reaction current value derived from the double strand identification material is measured. At this point, the potential may be applied at a constant rate, as a pulse, or as a constant potential. The current and voltage may be controlled by using devices such as a potentiometer, digital multimeter, and function generator.

In a method according to an embodiment using the probe immobilized substrate 300, 400, an amplification reaction and detection occur on these probe immobilized substrates in the same period. Alternatively, amplification products formed by an amplification reaction caused in a different reaction field may be brought onto these probe immobilized substrates for detection.

Part (c) of FIG. 8 is a sketch schematically showing an example of the mode in which an amplification reaction and a hybridization reaction are carried out on the probe immobilized substrate 300, 400 as one reaction field. A probe immobilized substrate 500 includes a substrate 501, probe immobilized regions 502 arranged on the substrate in an array, a plurality of probes 503 immobilized to the probe immobilized region 502 for each type, a primer set 505 releasably immobilized onto the substrate, and an amplification reagent 507 releasably immobilized onto the substrate. The primer set 505 and the amplification reagent 507 are releasable from the probe immobilized substrate 500 when a reaction field is formed by a liquid or due to contact with a liquid. For example, a method according to an embodiment by the probe immobilized substrate 500 may include bringing a sample or a liquid containing the sample onto the probe immobilized substrate 500, forming a reaction field using the liquid, bringing the reaction field under amplification reaction conditions and detection reaction conditions, and detecting hybridization. For example, the reaction field may be formed in a housing space such as a channel and a container. The fixing position of the primer set 505 and the amplification reagent 507 is not limited to a position on the substrate and may be an inner surface of a housing space in contact with a reaction field. The amplification reagent 507 is a reagent other than the primer set and may be a material or a combination of a plurality of materials needed for the amplification reaction. Alternatively, the amplification reagent 507 may be a material or a combination of a plurality of materials that can coexist during amplification reaction. The amplification reagent may be, for example, salt, a substrate such as dNTPs, or amplification enzymes.

Part (d) of FIG. 8 shows an example of the mode in which, for example, the above probe immobilized substrate includes a channel. This is an example of the probe immobilized substrate to cause each of an amplification reaction and a hybridization reaction in two reaction fields connected by the channel and may be combined with any of the above detection modes. A probe immobilized substrate 600 includes, for example, two chambers to maintain reaction fields inside a substrate 601. These are, for example, a first chamber 610 in which an amplification reaction is carried out and a second chamber 620 in which a hybridization reaction is carried out and these chambers are connected by a channel 630. A primer set 605 and a reaction reagent 607 are releasably immobilized to a bottom 615 of the first chamber 610. A plurality of probe immobilized regions 602 is arranged at a bottom 625 of the second chamber 620 in an array and a plurality of probes 603 is immobilized thereto for each type. A through hole 618 to allow a liquid to flow in is formed in an upper portion of the first chamber 610. A reaction in the probe immobilized substrate 600 may include bringing a sample or a liquid containing the sample into the first chamber 610 through the through hole 618, maintaining the first chamber 610 under amplification reaction conditions, sending the liquid in the first chamber that may contain amplification products into the second chamber 620 through the channel 630, maintaining the second chamber 620 under hybridization reaction conditions, and detecting hybridization generated in the second chamber 620.

In the example of the above probe immobilized substrate, an example in which the primer set and the amplification reagent are releasably immobilized is shown, but both of these do not necessarily need to be immobilized together and, for example, the primer set or the amplification reagent may be brought to a reaction field by being contained in a sample or a liquid containing the sample or may be brought to a reaction field separately. In all examples, a reagent that assists in generating a detectable hybridization signal or needed for the generation may be immobilized to any wall surface that defines a reaction field in which a hybridization reaction is carried out. In the above example, an example in which five probe immobilized regions are arranged is shown, but the number of regions can arbitrarily be changed. Arranging in an array means, for example, arranging desired numbers of regions vertically and horizontally.

The substrate may be in a solid phase and may be any substrate used generally as a solid phase for DNA chips. The substrate may be constructed of, for example, glass, silicon, nitrocellulose film, nylon film, microtiter plate, electrode, magnet beads, plastics, latex, synthetic resin, natural resin, or optical fiber, but the present embodiment is not limited to such substrates.

In addition to the detection probe for hybridization with the detection region associated with the target nucleic acid, the probe immobilized substrate may further include a negative control probe or a positive control probe. In that case, a fixing region to fix these probes may be arranged on the substrate.

Immobilizing of probes to the substrate is not limited to the above examples and, for example, a probe may be immobilized to the substrate via a terminal modification group, for example, the mercapto group, the amino group, the aldehyde group, the carboxyl group, or biotin. The selection of these functional groups and immobilizing of probes can be achieved by publicly known means.

The primer set and the amplification reagent are immobilized by, for example, dissolving or suspending these in water or an organic solvent, and dropping obtained liquid and drying.

For example, to carry out a hybridization reaction after an amplification reaction, the procedure described below may be executed. Amplification products obtained from an amplification reaction are brought into a reaction field of the probe immobilized substrate as described above. Hybridization of a probe and the amplification products is caused by maintaining the probe immobilized substrate with the probe under hybridization conditions. The hybridization temperature may appropriately be set. Salt may be added to enhance the efficiency of the reaction. For this purpose, salt may be immobilized to a neighborhood of the probe immobilized region of the probe immobilized substrate in advance. Alternatively, salt may be brought into the reaction field by adding and mixing salt in a liquid containing amplification products after an amplification reaction. For example, salt needed to satisfy hybridization conditions may be contained in an assay kit described below as a hybridization reagent. The liquid may be stirred or shaken during hybridization reaction or before/after the reaction. The efficiency of the reaction may thereby be enhanced.

A buffer solution whose ionic strength is in the range of 0.01 to 5 and whose pH is in the range of 5 to 9 may suitably be used as a washing fluid to clean the probe after the hybridization. The washing fluid may contain salt, a surface active agent etc. For example, an SSC solution, a Tris-HCl solution, a Tween20 solution, or an SDS solution may be used. The washing temperature may generally be, for example, 10° C. to 70° C. For example, the washing fluid may be passed through or held on the surface of the probe immobilized substrate or the probe immobilized region.

Hybridization generated in the hybridization process may be detected at a single desired time, chronologically, or at a plurality of times and a fluorescence detection method or an electrochemical detection method may be used.

Part (e) of FIG. 8 is an enlarged view extracting a portion showing a probe immobilized region and a probe immobilized thereto. A double strand nucleic acid probe (hereinafter, a double strand probe) shown in Part (e) of FIG. 8 may be used for a probe immobilized substrate. A probe immobilized substrate 700 includes a double strand probe 703 immobilized to a probe immobilized region 702. The double strand probe 703 contains an anchor nucleic acid chain (hereinafter, an anchor chain) 710 and a coating nucleic acid chain (hereinafter, a coating chain) 720 hybridized therewith. The coating chain 720 is trapped by the anchor chain 710 through hybridized binding, thereby immobilized to a substrate 701. In addition to an anchor complementary sequence 711 to bind to the anchor chain 710, the coating chain 720 contains a detection complementary sequence 721 to be hybridized with a detection region 751 to be detected. With the above configuration of the coating chain 720, an amplification product 750 and the anchor chain 710 compete to hybridize with the coating chain 720. As a result, when the amplification product 750 containing a corresponding detection region 751 approaches the double chain probe, the coating chain 720 may be released from the anchor chain 710 to hybridize with the amplification product 750 to form a double strand. The inventors have proved by experiment that this phenomenon occurs depending on the concentration of amplification products present in the reaction field. By using the double strand probe 703, for example, a hybridization reaction may be carried out in one reaction field in parallel with an amplification reaction and the generated hybridization can be detected chronologically and quantitatively. By using the double strand probe 703 as described above, amplification products can be determined with greater accuracy than in the past. Change from the double strand probe 703 to a single strand chain can be detected electrochemically or optically. For example, the double strand probe 703 may be immobilized onto the electrode for electrochemical detection.

With the coating chain being bound to the anchor chain in the double strand probe 703, the detection of a signal of a marker substance in the probe is inhibited. Inhibition of the detection of a signal of a marker substance in an embodiment means the detection being inhibited or detectability being inhibited like a state in which a signal originally generated by the marker substance cannot be detected or being modified to a state in which a signal that should be detected when the coating chain is not bound to the anchor chain cannot be detected. For example, inhibition means that a signal that is detected when an anchor chain having a marker substance becomes independent and is present as a single strand chain is attenuated, lost, or changed or modulated to an undetectable signal by hybridization of coating chain to anchor chain. Such inhibition of the detection of a signal of a marker substance is reversible. When binding of the coating chain to the nucleic acid probe is released, that is, the coating chain is detached from the nucleic acid probe, a signal originally generated by a marker substance becomes detectable.

The detection of change from the double strand probe 703 to a single strand chain is observed by using a marker substance that generates a detectable signal and such a marker substance is characterized in that the detection of a signal from the marker substance is inhibited by the presence or an increase in the amount of presence of nucleic acid bound to the anchor chain. In other words, when, for example, a nucleic acid is bound to the anchor chain, such a marker substance is characterized in that no signal is generated by the marker substance, the magnitude of the generated signal becomes smaller, a signal from the marker substance becomes less likely to be transmitted, and/or the detection thereof is inhibited.

Examples of such a marker substance may be electrode active materials and may include, though not limited to these materials, for example, electrochemically active metal complexes, iron complexes, ruthenium complexes, rubidium complexes, cobalt complex ions, ferricyanide ions, ferrocyanide ions, anthraquinone, and methylene blue. For example, ferricyanide ions, ferrocyanide ions, iron complex ions, ruthenium complex ions, and cobalt complex ions are also interpreted as oxidizing agents whose oxidation-reduction potential can become a detectable electrochemical signal and other oxidizing agents having such characteristics may similarly be used. For example, compounds containing ferrocene are preferably used. These markers are obtained by dissolving potassium ferricyanide, potassium ferrocyanide, iron complexes, ruthenium complexes, and cobalt complexes in a reaction liquid.

The concentration of these in the reaction liquid may be, for example, 10 μM to 100 mM or, for example, about 1 mM. When an electrochemically active material is used as a marker substance, arranging the marker substance closer to a sensor is preferable to farther from a sensor. If the distance of the marker substance from a sensor is, for example, about 50 bases, an electrochemical signal is preferably detectable. The distance of the marker substance from a sensor may be, though not limited to these examples, for example, 60 bases or less, 55 bases or less, 50 bases or less, 40 bases or less, 30 bases or less, 20 bases or less, or 10 bases or less. Alternatively, the marker substance may be arranged in a nucleic acid chain contained in the anchor chain, attached to a closer terminal or a farther terminal from the substrate of a nucleic acid chain, or arranged between a terminal modification group to bind a nucleic acid chain of the anchor chain and the substrate and the nucleic acid chain. Further, a plurality of marker substances may be contained in one anchor chain or a single marker substance may be contained. When a plurality of marker substances is contained, these markers may be of the same type or different types. Alternatively, the marker substance may be made to be present in a reaction liquid.

For example, when an amplification reaction and a hybridization reaction are allowed to proceed simultaneously in one reaction field, these reactions may be carried out as described below.

For example, when the probe immobilized substrate 700 including the double strand probe 703 on the electrode as the probe immobilized region 702 is used, the progress of hybridization can be monitored in real time while performing isothermal amplification on the substrate. That is, when isothermal amplification is performed on such a probe immobilized substrate, the detection complementary sequence 721 in the coating chain 720 and the amplification product 750 hybridize depending on the amount of presence of the amplification product 750 in the reaction liquid and the coating chain 720 is dissociated from the electrode 702. At this point, the probe immobilized to the electrode changes from a double strand chain to a single strand chain. This change can be grasped in real time as a signal change by examining electric responses continuously using the electrode. To obtain a signal using the electrode, for example, a marker substance in which an electrode active material such as ferrocene is bound to a double strand identification material can be used. In this case, when the probe changes to a single strand chain, ferrocene-marked double strand markers are dissociated. As a result, the ferrocene response decreases. Ferrocene repeats oxidation and reduction when potential sweeping is performed in cycles. Accordingly, the response can continuously be measured and thus, the progress of amplification can be monitored.

In addition, the response of an electrode active material reflects the state in the neighborhood of the electrode well. Therefore, the change of response can directly be measured without using any double strand identification material. In this case, potassium ferricyanide, potassium ferrocyanide, iron complexes, ruthenium complexes, cobalt complexes, or ferrocene may be used as the electrode active material. All these materials repeat oxidation and reduction when potential sweeping is performed in cycles. Thus, oxidation and reduction can repeatedly be measured with the progress of amplification. As the response of these electrode active materials when a double strand chain on the electrode changes to a single strand chain, the current value increases and/or the peak potential shifts to the lower potential side. The rate of amplification reaction depends on the amount of template before amplification and thus, if the time needed to exceed a predetermined threshold is measured, the amount of template before amplification can be calculated so that amplification products become determinable.

A signal from an electrochemically active material may be any one of electric indexes of, for example, the current value, potential value, electric capacity value, and impedance value. By measuring the quantitative change and/or the change of predetermined electric characteristics accompanying detachment of the coating nucleic acid chain 5 from the nucleic acid probe, the presence/absence or the amount of presence of target nucleic acid can be determined. The quantitative change of a signal or the change of electric characteristics may be, for example, the change in magnitude of a signal, for example, the attenuation or loss of a signal, the length of time needed until the change of such magnitude occurs, a shift of the starting point of the change of magnitude, or the change of integrated value in a specific time.

An electric signal from a nucleic acid probe may be acquired from the substrate to which the nucleic acid probe is immobilized. In that case, for example, an electrode may be arranged in at least a portion of the substrate surface. In that case, the nucleic acid probe may be immobilized onto the electrode.

Alternatively, instead of electrically active materials, an optically active material may be used. A signal from such a material may be some kind of optical index and, for example, light having a specific wavelength, for example, fluorescence, luminescence or the like. By measuring the quantitative change and/or the change of predetermined electric characteristics accompanying detachment of the coating chain from the nucleic acid probe, the presence/absence or the amount of presence of target nucleic acid can be determined. The quantitative change of a signal or the change of optical characteristics may be, for example, the change in light intensity, an increase in light intensity, the attenuation or loss, the change in wavelength, the length of time needed until the magnitude of light intensity or the wavelength changes, a shift of the starting point of such changes, or the change of integrated value in a specific time.

Examples of fluorescent materials include, though not limited to these materials, for example, Alexa flour, BODIPY, Cy3, Cy5, FAM, Fluorescein, HEX, JOE, Marina Blue (trademark), Oregon Green, Pacific Blue (trademark), Rhodamine, Rhodol Green, ROX, TEMRA, TET, and Texas Red(registered trademark).

Such optically active materials can inhibit detectability of the coating chain by, for example, including a quencher therein. Examples of the quencher include, for example, BHQ-1, BHQ-2, and Dabcyl. If, for example, Cy3 or Cy5 is selected as the marker substance, Eu chelate or Ulight may be used as the quencher.

By using such a double strand probe, a plurality of short-chain nucleic acids can easily be detected.

(5-2) Integral-Type Device and Measuring Apparatus

FIG. 9 shows a further example of the probe immobilized substrate. Part (a) of FIG. 9 is a plan view of the probe immobilized substrate and part (b) of FIG. 9 is a sectional view along line B-B. The probe immobilized substrate is an example of a device integrated (hereinafter, denoted as an integral-type device) by combining a plurality of components to continuously cause an amplification reaction in a reaction cell and a hybridization reaction on a DNA chip. Incidentally, an integral-type device 901 is also called a detection cassette or a detection cartridge.

The integral-type device 901 includes a specimen syringe 902, a washing fluid syringe 903, an intercalating agent syringe 904, a reaction cell 905, and a DNA chip 906. The DNA chip 906 is fixed to an inner bottom of a detection cell 916. The specimen syringe 902 is connected to the reaction cell 905 by a channel 907. The washing fluid syringe 903 and the intercalating agent syringe 904 are connected to the detection cell 916 by a channel 909. The reaction cell 905 is connected to the detection cell 916 by a channel 908. The integral-type device 901 includes a main body 920 and a lid body 930 mounted on one side thereof. Recesses 921a, 921b, 921c are formed on the lid body 930 side of the main body 920 and the specimen syringe 902, the washing fluid syringe 903, the intercalating agent syringe 904, the reaction cell 905, and the detection cell 916 are defined by the recesses 921a, 921b, 921c and the lid body 930. Through holes 931a, 931b, 931c are formed in positions of the lid body 930 corresponding to the specimen syringe 902, the washing fluid syringe 903, and the intercalating agent syringe 904 respectively. When used, the specimen syringe 902 has a sample to be inspected housed therein, the washing fluid syringe 903 has a washing fluid housed therein, and the intercalating agent syringe 904 has an intercalating agent involved in generating a hybridization signal housed therein. A sample, a washing fluid, and an intercalating agent are poured in through the through holes 931a, 931b, 931c in advance. Electrodes 906a as a plurality of probe immobilized regions are arranged on the DNA chip 906 in an array and a plurality of probes 906b is immobilized thereto for each type.

A measuring apparatus is used when a detection method of a plurality of target nucleic acids in a sample by the integral-type device 901 is executed. An example of the measuring apparatus is shown in part (c) of FIG. 9. A measuring apparatus 950 includes a measuring unit 960, a control mechanism 970 that controls the measuring unit 960, and a computer 980 that controls the control mechanism 970. The measuring unit 960 includes a cartridge housing unit 961 to which the integral-type device 901 is removably set as a cartridge, a measuring system 962 that obtains a signal from the integral-type device 901 housed therein, a liquid sending system 963 that sends and/or feeds a liquid to the integral-type device 901, and a temperature control mechanism 964 that controls the temperature of the integral-type device 901. The temperature control of the integral-type device 901 by the temperature control mechanism 964 is exercised by temperature control blocks 941a, 941b, 941c arranged inside the cartridge housing unit 961 and in contact with the bottom of the integral-type device 901 (part (b) of FIG. 9). The temperature control blocks 941a, 941b, 941c cover a region extending from the specimen syringe 902 through the washing fluid syringe 903 to the intercalating agent syringe 904, a region of the reaction cell 905, and a region of the detection cell 916 respectively. The temperature control blocks 941a, 941b, 941c may be, for example, a heater, a Peltier device, a cooling mechanism or the like. The temperature control blocks 941a, 941b, 941c may further be constructed of a plurality of small units and these units may be controlled independently.

Figure 10:
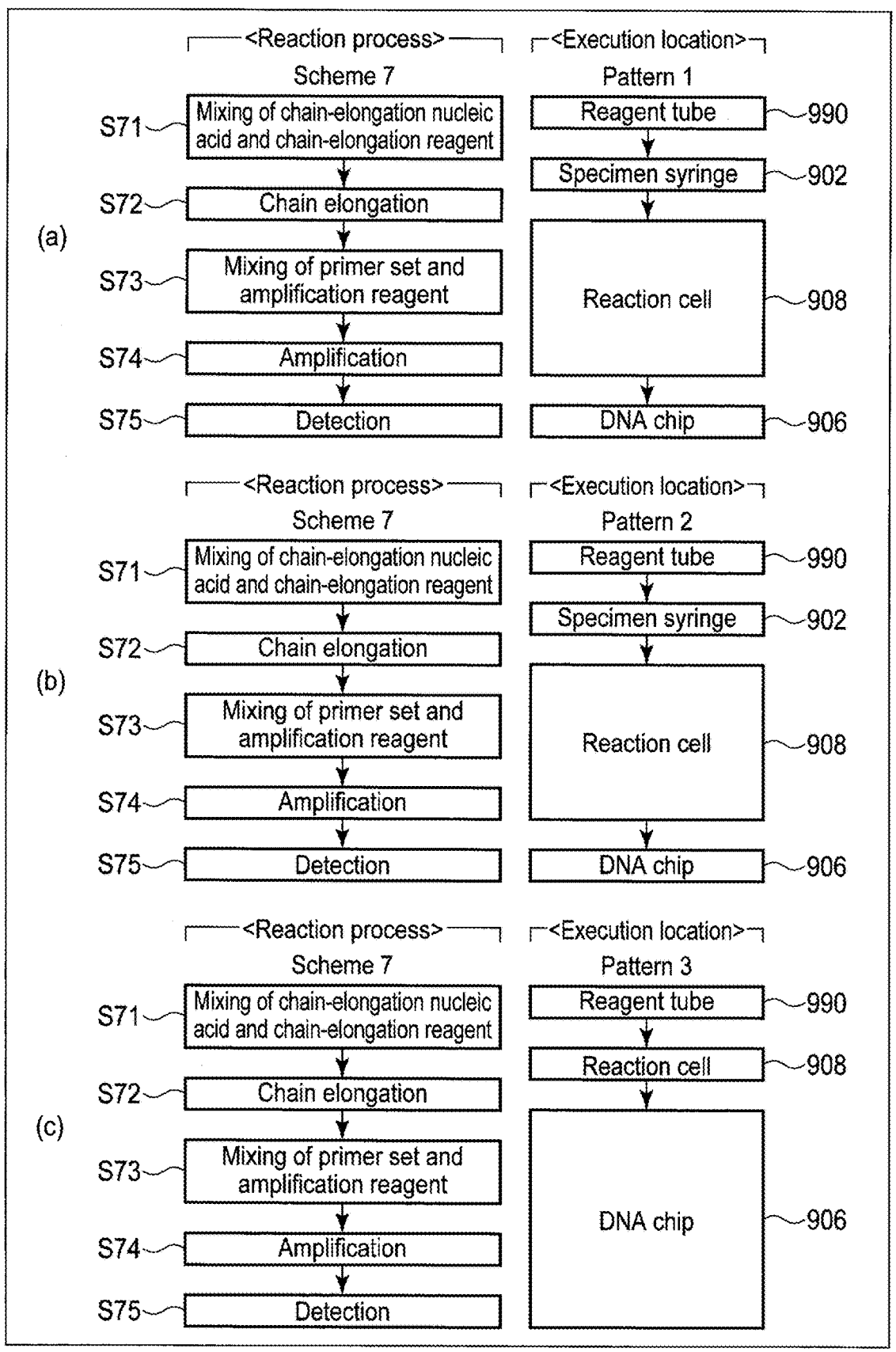
FIG. 10 is a flowchart showing an example of a detection method using the integral-type device and the measuring apparatus according to an embodiment.

An example of the detection method using the integral-type device 901 and the measuring apparatus 950 is shown in Scheme 7 of FIG. 10. The detection method includes mixing a sample that may contain a target nucleic acid, a chain-elongation nucleic acid set, and a chain-elongation reagent in a reagent tube 990 (S71), elongating the target nucleic acid inside the specimen syringe 902 (S72), mixing a long-chain nucleic acid, a primer set, and an amplification reagent in the reaction cell 905 (S73), amplifying the long-chain nucleic acid in the reaction cell 905 (S74), and detecting amplification products inside the DNA chip 906 (S75). A place where such a procedure is executed is shown in Pattern 1 in part (a) of FIG. 10.

Mixing in the reagent tube 990 is performed outside the integral-type device 901. Incidentally, the integral-type device 901 and the reagent tube 990 may be provided by being included in an assay kit described below together with the integral-type device 901. The reagent tube 990 contains a chain-elongation nucleic acid and a chain-elongation reagent in advance. To execute the detection method, a nucleic acid extracted from the sample material is added to the reagent tube 990 as a sample if necessary. After mixing the nucleic acid, a liquid mixture is housed in the specimen syringe 902 through the through hole 931a. The reaction liquid housed in the specimen syringe 902 is maintained under temperature conditions needed for chain elongation by the temperature control block 941a for a fixed time to promote chain elongation. After the chain elongation, the reaction liquid is sent from the specimen syringe 902 to the reaction cell 905 through the channel 907 by a liquid sending mechanism provided by the liquid sending system 963. The liquid sending mechanism 963 itself may use some known means. A primer set and an amplification reagent are releasably immobilized to the reaction cell 905 in advance. The primer set and the amplification reagent are released by contact with the reaction liquid and an amplification reaction is started under amplification reaction conditions. The amplification reaction conditions may be satisfied by the temperature control block 941b. After the amplification, the reaction liquid is sent from the reaction cell 905 to the detection cell 916 through the channel 908 by the liquid sending system 963. A plurality of probes is immobilized to the inner wall of the detection cell 916 in an array in advance. Further, a channel meandering a plurality of times is formed like covering the probe immobilized regions of the DNA chip 906 and a reaction field of the detection cell 916 may be present inside the channel. In this case, a plurality of probe immobilized regions may be arranged inside the channel at intervals along the flow direction. A hybridization reagent may be immobilized together with the probe. Temperature conditions for hybridization are satisfied by the temperature control block 941c. After the reaction liquid being maintained under hybridization conditions for a fixed time, a washing fluid housed in the washing fluid syringe 903 is sent to the detection cell 916 through the channel 909 by the liquid sending system 963. The washing fluid is maintained inside the detection cell 916 for a fixed time while the temperature there being maintained at the washing temperature by the temperature control block 941c. The hybridization reaction is thereby stopped. Then, an intercalating agent housed in the intercalating agent syringe 904 is sent to the detection cell 916 through the channel 909 by the liquid sending system 963. Each electrode to which a probe is immobilized is electrically connected to the measuring system 962. The measuring system 962 receives an electric signal generated by an electrode as a hybridization signal while applying a voltage to the electrode and sends the hybridization signal to the control mechanism 970 by associating with the detection position. The control mechanism 970 determines whether desired target nucleic acid is present in the sample based on the detection position, hybridization signals, predetermined thresholds for hybridization signals, preset formulas, and a table associating the detection position with the target sequence and if present, determines the amount of presence if necessary.

The control mechanism 970 is electrically connected to a measuring system 962, the liquid sending system 963, the temperature control mechanism 964, and the computer 980. The control mechanism 970 controls these systems based on, for example, programs, tables, and formulas stored in the computer 980. Further, the computer 980 may have a mechanism that stores obtained signals as measurement data. The computer 980 controls the control mechanism 970 by providing control condition parameters to the control mechanism 970 and may also detect and/or determine a target nucleic acid by analysis processing based on measurement data sent from the control mechanism 970.

In the examples of the above embodiment, examples of an apparatus that detects an electric signal are shown, but when a marker substance that generates an optical signal is used, a measuring apparatus may similarly be used. In that case, the configuration may be similar to the above except that, for example, the measuring system 962 is configured to detect an optical signal as a hybridization signal, no electrode may not be present in the probe immobilized region, and a reagent involved in detection of an optical signal is housed in the intercalating agent syringe. For example, the measuring system 962 when a fluorescent material is used as a marker substance may include an optical irradiation unit that irradiates the DNA chip 906 with excitation light, a sensing unit that obtains fluorescence from the marker substance as an optical signal, and a photoelectric conversion unit that converts an optical signal into an electric signal (not shown).

In the above embodiment, examples following Pattern 1 in part (a) of FIG. 10 are shown. In a further mode, two examples in which procedures executed by the integral-type device 901 and the measuring apparatus 950 configured in a manner similar to the above ones are changed will be described with reference to FIGS. 9 and 10. A first further example is Pattern 2 shown in part (b) of FIG. 10 and performs the same procedure as in Pattern 1 except that the chain is elongated (S72), instead of the specimen syringe 902, outside the integral-type device 901. In Pattern 2, a chain-elongation reaction is carried out in, for example, the reagent tube 990. In that case, chain elongation can be achieved by heating the reagent tube 990 using a heat block or the like. In such a detection system, the measuring apparatus 950 does not necessarily need to include the temperature control block 941*a*. The reaction liquid containing a long-chain nucleic acid formed inside the reagent tube 990 is housed in the specimen syringe 902 after passing through the through hole 931*a*. For example, the measuring apparatus 950 may further include a reagent tube folder so that the liquid sending system 963 extracts a reaction liquid from inside a reagent tube housed in the reagent tube folder by a syringe mechanism or the like and sends the reaction liquid into the specimen syringe 902 through the through hole 931*a* of the integral-type device 901 in the cartridge housing unit 961. Also, the measuring apparatus 950 may include a further temperature control block that adjusts the temperature of the reaction liquid in contact with the reagent tube 990 in the reagent tune folder.

A second further example is Pattern 3 shown in part (c) of FIG. 10 and performs the same procedure as in Pattern 1 except that the chain is elongated (S72) in the reaction cell 905 and mixing (S73) of a primer set and an amplification reagent and the amplification (S74) are performed on the DNA chip 906 of the detection cell 916. In Pattern 3, a chain-elongation reaction is carried out in the reaction cell 905. In that case, a liquid mixture from the reagent tube 990 poured through the through hole 931*a* may immediately be sent to the reaction cell 905. Chain elongation is achieved in the same manner as described above except that chain elongation is performed in the reaction cell 905, instead of performing in the reagent tube 990. In such a detection system, the measuring apparatus 950 does not necessarily need to include the temperature control block 941*a*. The reaction liquid after the chain elongation is sent to the detection cell 916 in the same manner as described above and the amplification, hybridization reaction, and detection may be performed like in Pattern 1 and Pattern 2 except that an amplification reaction and a detection reaction are carried out in the detection cell 916.

Alternatively, a hybridization reaction may be allowed to proceed while allowing an amplification reaction to proceed in the detection cell 916 according to the above mode and further, detection may be performed in one reaction field. In this case, there may be no temperature control unit corresponding to the specimen syringe 902. For the amplification reaction inside the detection cell 916, an amplification primer and an amplification reagent may be immobilized onto the DNA chip or to at least one wall surface inside the detection cell 916. Amplification is started by the amplification primer and the amplification reagent being dissolved. Pattern 3 as described above is preferable when a hybridization signal is measured in real time while allowing an amplification reaction and a hybridization reaction to proceed simultaneously. In that case, combining with a double strand chain probe is particularly preferable. In that case, electrode active materials needed for electrochemical detection may be housed in or immobilized to the reagent tube 990, the specimen syringe 902, the intercalating agent syringe 904, the reaction cell 905, or the detection cell 916 in advance in accordance with the selected procedure or if present, electrode active materials may be mixed in a liquid contained there.

A nucleic acid detection apparatus according to an embodiment can detect or determine a target nucleic acid easily with greater precision than in the past. Also, according to the nucleic acid detection apparatus, an inspection of the target nucleic acid can be performed in a shorter time than in the past.

6. Multiplex Detection Method of Short-Chain Nucleic Acid Concerning Multiple Series According to one embodiment, a multiplex detection method of short-chain nucleic acids concerning multiple series is provided. According to this method, a plurality of short-chain nucleic acids in a sample can easily be detected concerning a plurality of types of series by using the multiplex detection method for one series described above.

In an embodiment, one probe immobilized substrate may be used in common for all series. That is, one probe set may be used in common for all series. Also, one primer set may be used in common for all series. Sequence groups of detection regions used for one series may be used in common for all series. Sequence groups of detection regions used for one series are allocated to a plurality of target nucleic acids to be detected in that series. For example, a plurality of sequence groups of detection regions are prepared in advance and each of the target nucleic acid groups contained in the first series is associated with these sequence groups. When the number of series is increased, sequence groups of detection regions are allocated to target nucleic acid groups contained in each series. Such an association may be done for all series before the inspection of the first series is started or sequentially, or the series may periodically be increased in accordance with emergency conditions.

Each series contained in multiple series to be detected by the above method may be, for example, a common theme characterized by a plurality of short-chain nucleic acids, for example, health care related information. Multiple series may be, for example, combinations of indexes of mutually different states of health, combinations of different diseases, for example, cancer, diabetes, Basedow disease, collagen disease and the like, combinations of different gene-related diseases, combinations of different cancer types, for example, combinations of breast cancer, colon cancer, lung cancer and the like, and combinations of a plurality of examination items showing physical conditions of a particular person. These combinations can freely be selected by an implementer of the detection method according to an embodiment. For example, the combination may be overall determined before the inspection of one series or multiple series or selected sequentially as desired, or further inspections may be added in different periods as desired.

For example, an embodiment for multiple series may be a method of analyzing the first to n-th series. In that case, a preset target nucleic acid group may be contained as a small item set for each of the first to n-th series, the small item set may contain a plurality of small items, and the plurality of small items may correspond to detecting each of the target nucleic acid groups. A plurality of small item sets may contain a plurality of target nucleic acids in numbers independent of each other and these numbers may be identical to each other or different from each other.

The probe immobilized substrate is a universal probe immobilized substrate common to the first to n-th series (n is an integer equal to 2 or greater) and detecting a plurality of target nucleic acids corresponding to a small item set independently for each series may include (a) preparing a chain-elongation nucleic acid set group to obtain a long-chain nucleic acid containing a target sequence for each of a plurality of target sequences, (b) preparing a universal primer set containing a first primer that binds to a first amplification region and a second primer set that binds to a second amplification region to amplify a plurality of long-chain nucleic acids obtained from the chain-elongation nucleic acid set group in common, (c) preparing a probe immobilized substrate including a substrate and a plurality of probe groups immobilized to a surface in contact with a first reaction field provided by the substrate, (d) obtaining a long-chain nucleic acid group containing a first sub-chain-elongation nucleic acid and a second sub-chain-elongation nucleic acid or its complementary sequence for each of a plurality of target nucleic acids by annealing and ligation between each of the plurality of target nucleic acids, and a corresponding first sub-chain-elongation nucleic acid and a corresponding second sub-chain-elongation nucleic acid and/or nucleic acid elongation after a sample and the chain-elongation nucleic acid set group prepared in (b) being brought into a second reaction field, (e) obtaining an amplification product group by maintaining the long-chain nucleic acid group and the universal primer set under amplification conditions in a third reaction field, (f) detecting the presence/absence and/or the amount of hybridization between all the amplification product group generated in (e) and a first probe in a first reaction field, (g) detecting the plurality of target nucleic acids present in the sample based on a result of (f), (h) obtaining an analysis result for each of the first to n-th series based on the result of (g), and (i) obtaining an analysis result of an n+(1 to s)-th further series based on a result of the (a) to the (g) performed after the n+(1 to s)-th further series being added as desired, where s is an integer equal to 2 or greater.

Further, according to an embodiment, the numbers of small items contained in each of the first to n-th small item sets may be $m_1$ to $m_n$, the maximum value in the first to n-th small item sets may be $m_{max}$, m and n may be independent of each other and integers equal to 2 or greater, any x-th series among the first to n-th series may be analyzed using the corresponding x-th small item set, the x-th small item set may contain $1_x$-th to $m_x$-th small items, and $1 \leq m_x \leq m_{max}$ may apply.

Here, the first reaction field and the third reaction field are one common reaction field and an amplification reaction and detection and/or measurement are carried out in the same period so that the detection signal may be monitored continuously or detected or measured over time at a plurality of points in time.

According to such an embodiment as described above, a plurality of short-chain nucleic acids contained in one series can easily be detected in the same period and such an effect can be obtained for a plurality of series.

7. Combinatorial Analysis Kit

According to an embodiment, a combinatorial analysis kit is provided. This is an assay kit to execute the detection method according to an embodiment and is also called a kit below. The kit may contain a chain-elongation nucleic acid set group for one series containing two or more of the above chain-elongation nucleic acid sets, a universal primer set, and a probe immobilized substrate including two or more probes. Further, the assay kit may optionally include a chain-elongation reagent, an amplification reagent, for example, an enzyme, substrate, buffer, or buffer solution, a hybridization reagent, for example, salt, a washing agent, for example, a washing fluid, a marker substance, for example, an electrode active material or double strand identification material, a manual and any combination thereof.

The probe immobilized substrate is included by fixing two or more probe groups. The probe immobilized substrate may further be provided as an integral-type device including, for example, at least one selected from a chain-elongation nucleic acid set, chain-elongation reagent, universal primer set, amplification reagent, hybridization reagent, washing agent, marker, and a combination thereof in a releasably immobilized state or providing a chain-elongation reagent and washing agent contained in a liquid as, for example, a chain-elongation reagent and washing fluid. Alternatively, these elements may be contained in a kit separately from the probe immobilized substrate. In that case, at least one selected from a chain-elongation nucleic acid set, chain-elongation reagent, universal primer set, amplification reagent, hybridization reagent, washing agent, marker, and a combination thereof may be provided in a state of being contained in at least one reagent tube.

For example, the kit may contain a reagent tube for reactions carried out outside the probe immobilized substrate. The reagent tube may contain, for example, a chain-elongation reagent in a solid or liquid state. A kit including such a reagent tube as a first tube may further contain a second reagent tube. The second reagent tube may contain at least one selected from a chain-elongation nucleic acid set, chain-elongation reagent, universal primer set, amplification reagent, hybridization reagent, washing agent, marker, and a combination thereof. For example, the second reagent tube may contain an element that is not contained in the first reagent tube and is not included in the integral-type device.

For example, the kit is produced for each series. An example of how to combine kits to execute the multiplex detection method of short-chain nucleic acid for the above multiple series will be described with reference to Table 1.

TABLE 1

Example of kit component

| | Assay kit I | | Assay kit II | | Assay kit III | | Assay kit IV | |
|---|---|---|---|---|---|---|---|---|
| | Target short-chain nucleic acid | Detection sequence | Target short-chain nucleic acid | Detection sequence | Target short-chain nucleic acid | Detection sequence | Target short-chain nucleic acid | Detection sequence |
| Nucleic acid for chain-elongation | Nucleic acid 11 | Probe A | Nucleic acid 21 | Probe A | Nucleic acid 31 | Probe A | Nucleic acid 41 | Probe A |
| | Nucleic acid 12 | Probe B | Nucleic acid 22 | Probe B | Nucleic acid 32 | Probe B | Nucleic acid 42 | Probe B |
| | Nucleic acid 13 | Probe C | Nucleic acid 23 | Probe C | Nucleic acid 33 | Probe C | Nucleic acid 43 | Probe C |
| | Nucleic acid 14 | Probe D | Nucleic acid 24 | Probe D | Nucleic acid 34 | Probe D | Nucleic acid 44 | Probe D |
| | Nucleic acid 15 | Probe E | Nucleic acid 25 | Probe E | | | Nucleic acid 45 | Probe E |
| | Nucleic acid 16 | Probe F | Nucleic acid 26 | Probe F | | | Nucleic acid 46 | Probe F |
| | | | Nucleic acid 27 | Probe G | | | Nucleic acid 47 | Probe G |
| | | | Nucleic acid 28 | Probe H | | | | |
| Primer For amplification | Universal primer set (one set) | | | | | | | |
| DNA chip | Probe A, B, C, D, E, F, G, H fixing DNA chip | | | | | | | |

A kit I, a kit II, a kit III, and a kit IV to inspect a series I, a series II, a series III, and a series IV are kits to detect target nucleic acids 11 to 16, target nucleic acids 21 to 28, target nucleic acids 31 to 34, and target nucleic acids 41 to 47 respectively. Here, target nucleic acids are all short-chain nucleic acids. A specific sequence to each of the target nucleic acids are defined as a target sequence. A sequence of a detection region is allocated to each of these target sequences. At this point, a detection sequence A is allocated to a target nucleic acid group 11, 21, 31, 41 (that is, 10N+1, 1≥N≥4), a detection sequence B is allocated to a target nucleic acid group 12, 22, 32, 42 (that is, 10N+2), a detection sequence C is allocated to a target nucleic acid group 13, 23, 33, 43 (that is, 10N+3), a detection sequence D is allocated to a target nucleic acid group 14, 24, 34, 44 (that is, 10N+4), a detection sequence E is allocated to a target nucleic acid group 15, 25, 45 (that is, 10N+5), a detection sequence F is allocated to a target nucleic acid group 16, 26, 46 (that is, 10N+6), a detection sequence G is allocated to a target nucleic acid group 27, 47 (that is, 10N+7), and a detection sequence H is allocated to a target nucleic acid group 28 (that is, 10N+8). Accordingly, a chain-elongation nucleic acid set is produced for each type of target nucleic acid. The amplification region is made common throughout all groups. A primer set is prepared according to the amplification region. The primer set is a universal primer set common throughout all groups. The probe group may contain sequences complementary to the detection sequence A, the detection sequence B, the detection sequence C, the detection sequence D, the detection sequence E, the detection sequence F, the detection sequence G, and the detection sequence H or a probe A, a probe B, a probe C, a probe D, a probe E, a probe F, a probe G, and a probe H having the same sequence as the above sequence respectively. A sequence of a probe group may select a complementary sequence to the sequence of a detection region or the same sequence in consideration of the sequence of an amplification product. Alternatively, two types of probes containing both sequences may be prepared.

Such a probe group is immobilized for each type to the surface where a reaction field of the probe immobilized substrate. The mode of the probe immobilized substrate is selected as desired. For example, a probe group is provided by producing the probe immobilized substrate as a DNA chip and fixing the DNA chip into the detection cell of the above integral-type device. By using a common integral-type device mounted with a probe group common among series, that is, a universal integral-type device, it becomes possible to use a common measuring apparatus. By using such an integral-type device as a cartridge, versatility of inspection is improved.

Elements contained in a combinatorial analysis kit may be provided, for example, at different times, from a provider, for example, a provider such as a manufacturer or seller to a provision destination, for example, a user, for example, a hospital, inspection institute, research facilities, or an object, for example, a subject or patient. For example, when a provision destination possessing a corresponding measuring apparatus uses a combinatorial analysis kit, a combinatorial analysis kit for a plurality of short-chain nucleic acids to be inspected as the first series may be acquired.

The combinatorial analysis kit contains, for example, a first reagent tube housing a chain-elongation nucleic acid set to detect a plurality of target nucleic acids contained in the first series and an integral-type device. For example, the integral-type device is the above integral-type device 901 and may contain a chain-elongation reagent releasably immobilized to an inner wall of the specimen syringe 902, a washing fluid housed in the washing fluid syringe 903, a marker substance liquid housed in the intercalating agent syringe 904, a universal primer set and an amplification reagent releasably immobilized into the reaction cell 905, a plurality of probe sets immobilized onto electrodes arranged in an array on the DNA chip 906 immobilized inside the detection cell 916, and/or salt releasably immobilized to the inner wall of the detection 916.

In a further mode, the combinatorial analysis kit contains, for example, a first reagent tube housing a chain-elongation nucleic acid set to detect a plurality of target nucleic acids contained in the first series and an integral-type device. The integral-type device is, for example, the integral-type device 901 configured to cause an amplification reaction and a hybridization reaction in one reaction field and may contain a chain-elongation reagent releasably immobilized to the inner wall of the reaction cell 905, a washing fluid housed in the washing fluid syringe 903, a marker substance liquid housed in the intercalating agent syringe 904, a plurality of probe sets immobilized onto electrodes arranged in an array on the DNA chip 906 fixed inside the detection cell 916, and a universal primer set and amplification reagent immobilized releasably. In any mode, the probe set is one of the above probes and may be, for example, a double strand probe.

Here, a plurality of integral-type devices is delivered to the provision destination earlier and when the inspection of a desired inspection item becomes necessary, a reagent tube housing a plurality of chain-elongation nucleic acid sets to detect a plurality of target nucleic acids contained in the series to be inspected may sequentially be provided. Alternatively, a first reagent tube for a plurality of types of series and a plurality of corresponding integral-type devices may be delivered together and the number of types of the first reagent tube and the number of integral-type devices may be different or the same. Alternatively, a set of components needed to detect a plurality of target nucleic acids contained in a particular series may be provided for each series. Alternatively, a combinatorial analysis kit containing a set of components needed for multiplex detection of a single series in a state of forming one grouping may be provided as a combinatorial analysis kit.

Alternatively, for example, an integral-type device may be delivered to a first provision destination possessing a corresponding measuring apparatus and a reagent tube housing a plurality of chain-elongation nucleic acid sets to detect a plurality of target nucleic acids contained in the series to be inspected may be provided to a second provision destination that extracts a sample material from an object like an inspection institute such as a hospital.

That is, a plurality of elements contained in a combinatorial analysis kit according to an embodiment may be separated from each other temporally and/or spatially. Alternatively, the number of a plurality of elements contained therein and different from each other does not necessarily need to correspond to each other.

The kit may contain (1) a reagent to obtain amplification products of long-chain nucleic acid by elongating a plurality of target nucleic acids containing a plurality of target sequences having different sequences from each other, to form a plurality of long-chain nucleic acids respectively and (2) at least one probe immobilized substrate provided by being combined with the reagent to detect amplification products. At this point, each of the plurality of target nucleic acids are short-chain nucleic acid having a first sub-target sequence at the 5'-terminal and a second sub-target sequence at the 3'-terminal and the reagent may contain a primer set containing a first primer containing a sequence common to (a) a plurality of chain-elongation nucleic acid group containing first sub-chain-elongation nucleic acid and second sub-chain-elongation nucleic acid corresponding to each of the plurality of target nucleic acids and (b) the plurality of target nucleic acids and binding to the first amplification region and a second primer containing a sequence common among the plurality of target nucleic acids and binding to the second amplification region.

If, for example, the primer set is one for the PCR method, the combination of the first primer and the first primer may be a combination of a forward primer and a reverse primer; and further, the plurality of target nucleic acids are first to m-th target nucleic acids, where m is an integer equal to 2 or greater, the plurality of target sequences are first to m-th target sequences corresponding respectively to the target nucleic acids, the first sub-target sequence is the $1_1$ to $1_m$-th sub-target sequences corresponding to the plurality of target sequences, the second sub-target sequence is the $2_1$ to $2_m$-th sub-target sequences corresponding to the plurality of target sequences, the sequence of the first amplification region is common among $1_1$ to $1_m$-th sub-chain-elongation nucleic acids, the first amplification region contains a sequence that binds to the sequence of the first primer, the sequence of the second amplification region is common among $2_1$ to $2_m$-th sub-chain-elongation nucleic acids, and the second amplification region contains a sequence that binds to the sequence of the second primer. If amplification conditions are reaction conditions of the LAMP method, the target nucleic acid may be first to m-th target nucleic acids, where m is an integer equal to 2 or greater, the plurality of target sequences is the first to m-th target sequences corresponding to the plurality of target nucleic acids respectively, the first sub-target sequence is the $1_1$ to $1_m$-th sub-target sequences corresponding to the plurality of target sequences respectively, the second sub-target sequence is the $2_1$ to $2_m$-th sub-target sequences corresponding to the respective target sequences, the first amplification region is an F2 binding region and further, the first sub-chain-elongation nucleic acid contains an F1 binding region, and the F1 binding region may exist between the F2 binding region and a first sub-target binding region. If, for example, the first detection region is contained in a first sub-chain-elongation nucleic acid, the first detection region may contain a sequence that exists, on the first sub-chain-elongation nucleic acid, between bases adjacent to the F1 binding region to avoid overlapping and a region overlapping with the F2 binding region and does not overlap with the F2 binding region. The sequence of the second amplification region is a B2 binding region and further, the second sub-chain-elongation nucleic acid contains a B1 binding region, and the B1 binding region may exist between the B2 binding region and a second sub-target binding region. If the second detection region is contained in a second sub-chain-elongation nucleic acid, the second detection region may be present, on the second sub-chain-elongation nucleic acid, in the range from the 5'-terminal side bases at the 5'-terminal of the B1 binding region to the 3'-terminal side from the 5'-terminal of the B2 binding region. The first primer may be an FIP primer that contains an F1c sequence at the 5'-terminal and an F2 sequence at the 3'-terminal and the second primer may be a BIP primer that contains a B1c sequence at the 5'-terminal and a B2 sequence at the 3'-terminal. The first detection region may be $1_1$ to $1_m$-th detection regions corresponding respectively to target sequences and the second detection region may be $2_1$ to $2_m$-th detection regions corresponding respectively to target sequences. Corresponding to the first detection region and/or the second detection region, the probe may be $1_1$ to $1_m$-th probes and/or $2_1$ to $2_m$-th probes.

According to a further embodiment, the reagent may be a first reagent associated with the first series and a plurality of target sequences for the first reagent may be a target nucleic acid group related to the first series. A combinatorial analysis kit may be provided by combining a probe immobilized substrate, at least one of second to n-th reagents provided in combination with the first reagent and associated with the second to n-th series respectively.

The second to n-th reagents are reagents associated with the second to n-th series respectively and are reagents that elongate a plurality of target nucleic acids containing a plurality of target sequences having different sequences from each other, within the series respectively to form amplification products of long-chain nucleic acid and/or first to n-th small item sets containing $m_1$ to $m_n$ small items preset for the first to n-th series may be set respectively. The numbers of small items contained in the first to n-th small item sets are $m_1$ to $m_n$ and $m_1$ to $m_n$ may be identical to each other or different from each other. The maximum value in the first to n-th small item sets is $m_{max}$, m and n are independent of each other and integers equal to 2 or greater, and types of small items contained in each of the first to n-th series may be different at least partially between the series. Any x-th series of the first to n-th series is analyzed using a corresponding x-th small item set and the x-th small item set contains $1_x$-th to $m_x$-th small items with $1 \le m_x \le m_{max}$.

The $1_x$-th to $m_x$-th small items are intended to obtain information about the presence or amount of presence of $1_x$-th to $m_x$-th target nucleic acids having $1_x$-th to $m_x$-th target sequences having sequences different from each other and the $1_x$-th to $m_x$-th target sequences contained in the x-th small item set may be a target nucleic acid group related to a theme common throughout the x-th series. The $1_x$-th to $m_x$-th target sequences may contain $1_{1x}$-th to $1_{mx}$-th sub-target sequences at the 5'-terminal and $2_{1x}$-th to $2_{mx}$-th sub-target sequences at the 3'-terminal respectively.

Though the needed numbers of types of detection regions and probes are different among series, the primer set, probe group, for example, the probe immobilized substrate of an integral-type device can be used in common through a plurality of series. By fixing the configuration of such common components, an assay kit can easily be combined at low cost. Using such an assay kit, the inventory control of the assay kit is made simple and easy on both of the provider side and the consumer side so that running costs can be reduced.

8. Combinatorial Analysis Kit Supply Management Method

An embodiment is a method of managing provision of the combinatorial analysis kit to execute the multiplex detection method of short-chain nucleic acid in the above multiple series.

An example of the method of provision will be described with reference to FIG. 11. This method may be a method of providing any one of combinatorial analysis kits described above. The kit contains, for example, a reagent tube housing a chain-elongation nucleic acid set to detect a plurality of target nucleic acids contained in one series and a universal integral-type device. The universal integral-type device is the above integral-type device may contain a chain-elongation reagent releasably immobilized to an inner wall of the specimen syringe 902, a washing fluid housed in the washing fluid syringe 903, a marker substance liquid housed in the intercalating agent syringe 904, a universal primer set and an amplification reagent releasably immobilized into the reaction cell 905, a plurality of probe sets immobilized onto electrodes arranged in an array on the DNA chip 906 fixed inside the detection cell 916, and salt releasably immobilized to the inner wall of the detection 916. When such a combinatorial analysis kit is used, the universal integral-type device may, for example, always have the same configuration. On the other hand, the chain-elongation nucleic acid is different among the series and a particular series may be selected depending on the object to be inspected. Due to such a configuration, the management of the universal integral-type device can collectively be controlled.

Figure 11:
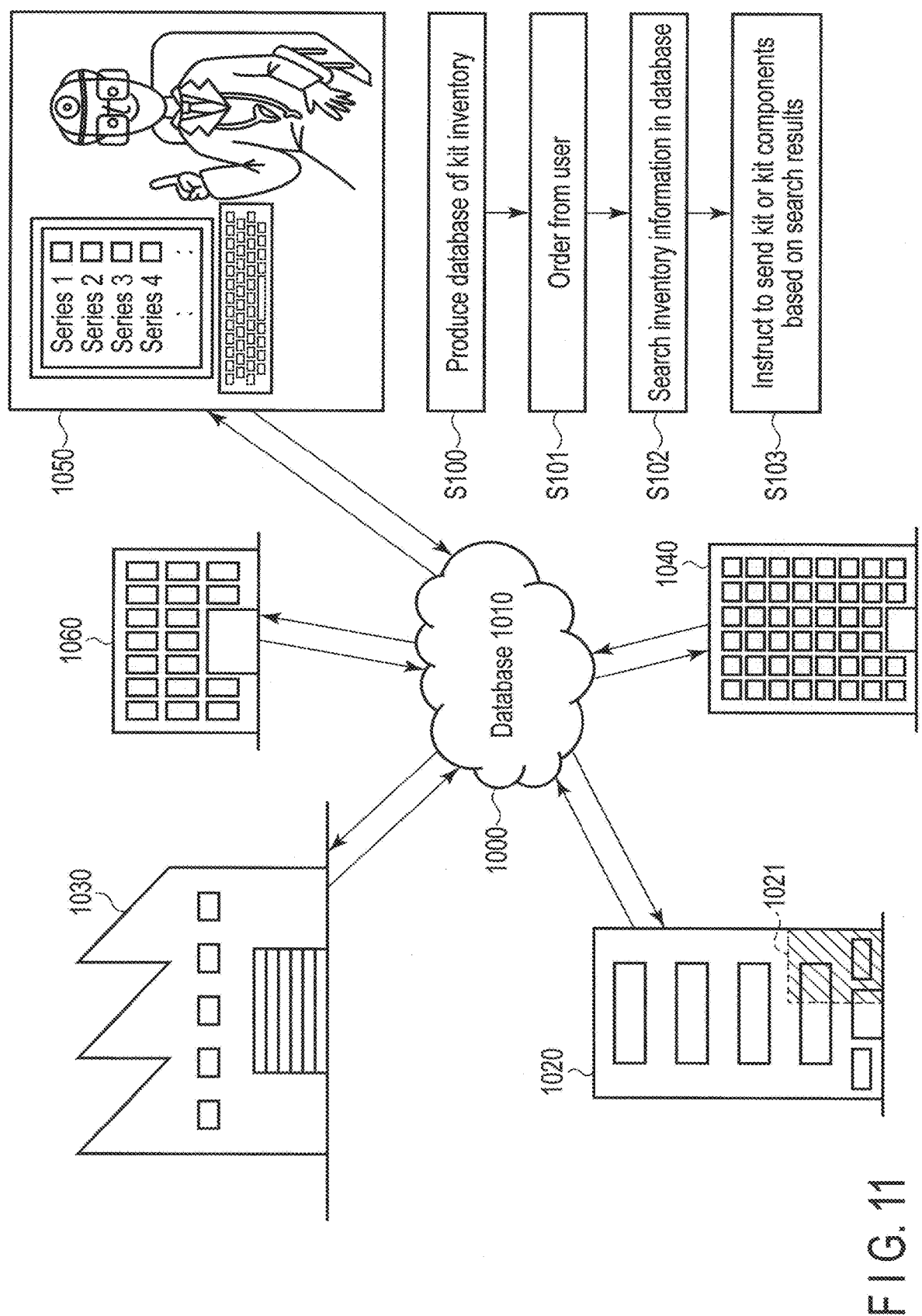
FIG. 11 is a schematic diagram showing an example of a supply management method according to an embodiment.

For example, as shown in FIG. 11, the stock status of the kit can be stored in a cloud 1000 as a database 1010. In the database 1010, inventory information held by a provider 1020 of the kit can be stored. A factory 1030 held by the provider 1020 can store inventory information of the kit being produced. A wholesaler 1040 holding the kit from the provider can store its inventory information there. A first usage facility 1050 and a second usage facility 1060 using the kit can also store its inventory information there. The database 1010 is created from such inventory information. Based on the above information, for example, a management system 1021 of the provider, for example, a computer performs supply management of the kit. The inventory information may include, for example, the number of kits and the number of components of each kit, the type of series, information of the target sequence contained by the series, the number and type of kits being produced, the date of manufacture of the kit or each component, and information about service life.

FIG. 11 provides an overview of the procedure in an example of the present embodiment. If, for example, the first usage facility 1050 is a medical institution like a hospital, a physician in a consultation room may issue an order to conduct a first series inspection (S101). The order is sent to the management system 1021. Upon receipt of the order, the management system 1021 searches data in the data base 1010 (S102) to identify the kit, for example, geographically nearest to the facility 1050 and temporally closest to the expiration date and issues instructions to send the kit to the facility 1050 (S103). Following the instructions, the ordered kit is sent to the facility 1050. The sent kit may have been included in, for example, the provider 1020, the factory 1030, the wholesaler 1040, or the inventory possessed by the second facility 1060. Conditions for selecting the kit to be sent to the facility 1050 may be preset conditions as desired and can also be changed arbitrarily. Such conditions may be set like, for example, being geographically near or nearest to the provision destination, being temporally close or closest to the expiration date, and being able to transport together with other products through routine distribution. Inventory information is associated with the location where the stock thereof is stored. Data included in the data base 1010 may be present as a table or as an aggregate of publicly known data.

Alternatively, the management system 1021 may monitor the cloud 1000. The order (S101) from the facility 1050 is sent to the cloud 1000 and stored in an order storage unit. The management system 1021 detects the order newly added to the cloud 1000, searches inventory data of the cloud 1000 (S102), instructs the factory 1030 to send, for example, a reagent tube to the facility 1050 after the tube being produced, and issues instructions to send an integral-type device in a location geographically near the facility 1050 to the facility 1050. Following the instructions, the ordered kit is set to the facility 1050 in units of components (S103).

If, for example, only the reagent tube is present in the facility 1050, the management system detects a signal responding to the order (S101) of the physician in the data base 1010 and notifies an inspection execution unit (not shown) of the facility 1050 that the reagent tube is available in the facility 1050 (S102) and issues instructions to send an integral-type device to the facility 1050 by the above method (S103).

An example of using the cloud 1000 is shown above, but instead of the cloud 1000, the management system 1021 may have a database to store information there. In that case, information sent to the cloud 1000 and information sent from the cloud 1000 such as a signal related to orders are sent to the management system 1021 and based on the information, the procedure for transfer is performed as described above.

The inventory information included in the cloud 1000 may be present independently as information about chain-elongation nucleic acid sets and information about probe immobilized substrates, for example, universal integral-type devices. Orders from the user may be a kit set to inspect a particular series or a portion thereof, for example, one of a chain-elongation nucleic acid set and a probe immobilized substrate.

Due the above method of provision, the inspection executor can obtain a kit more simply and easily and also can conduct an inspection of a plurality of short-chain nucleic acids in the same period more simply and easily. Due to such a kit, the inventory control of the kit is made simple and easy on both of the provider side and the consumer side so that running costs can be reduced. Also, by managing to preferentially use, for example, the kit closest to the expiration date, excessive production in the factory can be prevented while avoiding wasteful stock.

EXAMPLES

In the following examples, sub-chain-elongation nucleic acid is abbreviated as chain-elongation nucleic acid. Reference signs of drawings referenced in the examples are attached as a separate system from the drawings and reference signs cited above.

Figure 12:
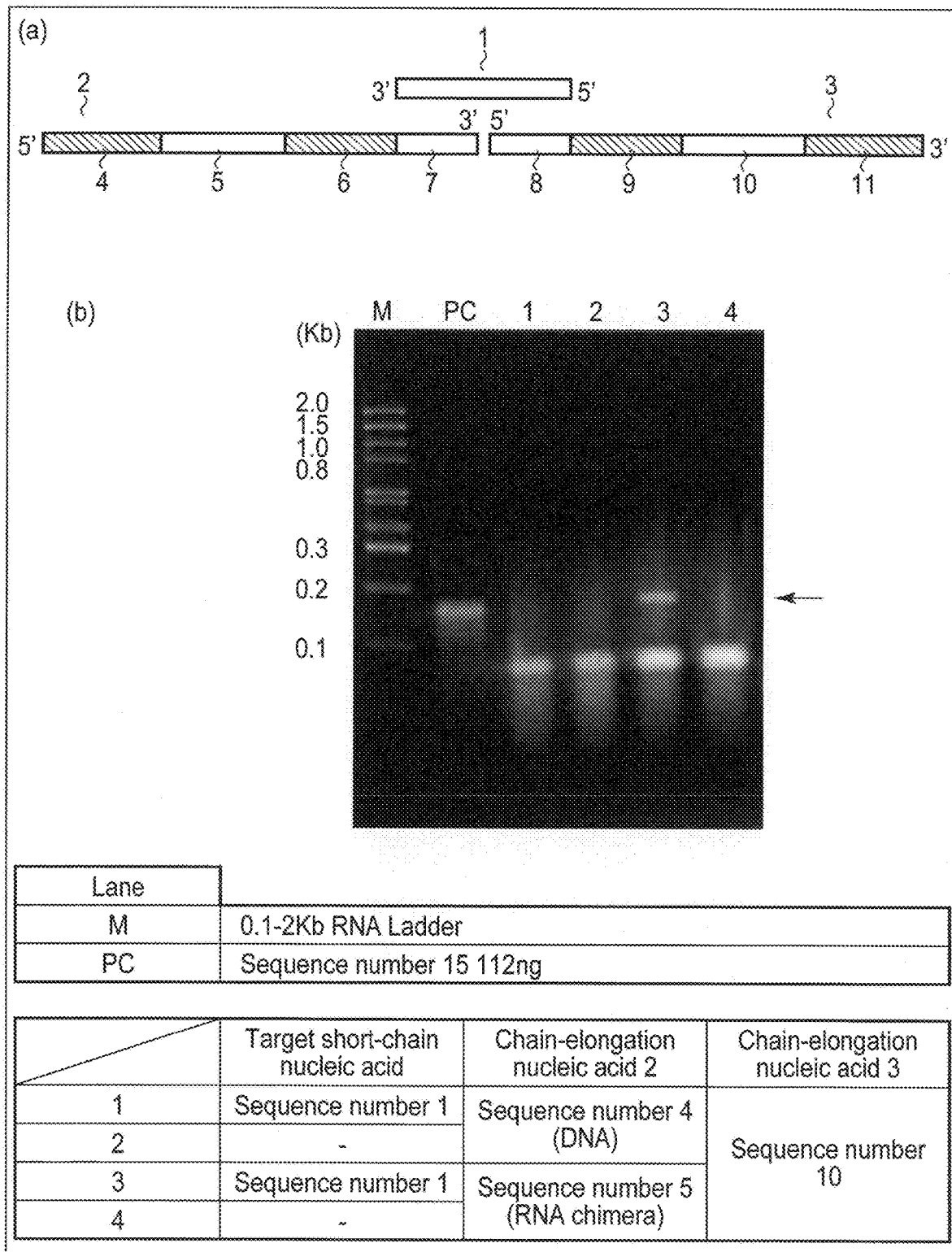
FIG. 12 is a diagram showing an experimental result.

1. Multiplex Detection of Short-Chain Nucleic Acid by LAMP (1) Preparation of Chain-Elongation Nucleic Acid To detect miRNA let-7-a (sequence number 1) shown in Table 2, following an embodiment, a chain-elongation nucleic acid 2 (sequence numbers 4 and 5) and a chain-elongation nucleic acid 3 (sequence number 10) shown in FIG. 12(*a*) are prepared. The sequence number 4 is synthetic DNA oligo and the sequence number 5 is chimera synthetic oligo whose 2 bases at the 3'-terminal are RNA.

TABLE 2

Target short-chain nucleic acid

| Sequence number | Name | Object | Sequence (5'-3') |
|---|---|---|---|
| 1 | miRNA let-7-a | let-7-a | UGAGGUAGUAGGUUGUAUAGUU |
| 2 | miRNA 21-5p | miR 21-5p | UAGCUUAUCAGACUGAUGUUGA |
| 3 | miRNA 21-3p | miR 21-3p | CAACACCAGUCGAUGGGCUGU |

The sequence number 10 is synthetic DNA oligo whose 5'-terminal is phosphorylated. An amplification sequence 4, a detection sequence 5, and a primer binding sequence 6 contained in the sub-chain-elongation nucleic acid 2 have a sequence number 6, a sequence number 7, and a sequence number 8 respectively. A sequence of a target binding region 7 (target short-chain nucleic acid partial complementary chain 7) annealed to miRNA has a sequence number 9. A sequence of a target binding region 8 (target short-chain nucleic acid partial complementary chain 8) annealed to miRNA contained in the chain-elongation nucleic acid 3 has a sequence number 11. A primer binding sequence 9, an amplification sequence 10, and an amplification sequence 11 have a sequence number 12, a sequence number 13, and a sequence number 14 respectively. Also, synthetic oligo DNA sequence number 15 in which the chain-elongation nucleic acid 2 and the chain-elongation nucleic acid 3 are connected is prepared as a positive control of a ligation reaction. Details of each sequence are shown in Tables 3 and 4. In the tables, the primer binding sequence is denoted as the amplification sequence.

TABLE 3

Chain-elongation nucleic acid

| Sequence number | Name | Object | Sequence (5'-3') |
|---|---|---|---|
| 4 | Chain-elongation nucleic acid 2 (DNA) | let-7-a | CCTTCGGAGAACCCCTCTCTACGTAAGGATAGCAAGTGACTGCGCGGAAGAAGTCG CGGTTTTGATATGCTGGACGAACTATACAAC |
| 5 | Chain-elongated nucleic acid 2 (RNA) | | CCTTCGGAGAACCCCTCTCTACGTAAGGATAGCAAGTGACTGCGCGGAAGAAGTCG CGGTTTTGATATGCTGGACGAACTATACArArC |
| 6 | Amplification sequence 4 | | CCTTCGGAGAACCCCTCT |
| 7 | Detection sequence 5 | | CTACGTAAGGATAGCAAGTGACTGCGCGGAAGAAGT |
| 8 | Amplification sequence 6 | | CGCGGTTTTGATATGCTGGACG |
| 9 | Target short-chain nucleic acid partial complementary chain 7 | | AACTATACAAC |
| 10 | Chain-elongation nucleic acid 2 | | P04CTACTACCTCACGATTCACGATGCATCCGGCATAACGGAGCCATCCGAGCCCA ACAGCAGCCGGGGAGTTGACGAGTTCGTACCAGAACGTC |
| 11 | Target short-chain nucleic acid partial complementary chain 8 | | CTACTACCTCA |
| 12 | Amplification sequence 9 | | CGATTCACGATGCATCCGGCA |
| 13 | Amplification sequence 10 | | TAACGGAGCCATCCGAGCCCAACAGCAGCCGGGGAGTTGA |
| 14 | Amplification sequence 11 | | CGAGTTCGTACCAGAACGTC |
| 15 | Ligation PC | | CCTTCGGAGAACCCCTCTCTACGTAAGGATAGCAAGTGACTGCGCGGAAGAAGTCG CGGTTTTGATATGCTGGACGAACTATACAACCTACTACCTCACGATTCACGATGC ATCCGGCATAACGGAGCCATCCGAGCCCAACAGCAGCCGGGGAGTTGACGAGTTC GTACCAGAACGTC |
| 16 | Chain-elongated nucleic acid 2 (RNA) | miR 21-5p | CCTTCGGAGAACCCCTCTGGGGATGTGGATCTTTACTCCATGGATAACGCGGTT TTGATATGCTGGACGTCAACATCArGrT |
| 17 | Chain-elongated nucleic acid 3 | | P04CTGATAAGCTACGATTCACGATGCATCCGGCATAACGGAGCCATCCGAGCCCA ACAGCAGCCGGGGAGTTGACGAGTTCGTACCAGAACGTC |

TABLE 3-continued

Chain-elongation nucleic acid

| Sequence number | Name | Object | Sequence (5'-3') |
|---|---|---|---|
| 18 | Chain-elongated nucleic acid 2 (RNA) | miR 21-3p | CCTTCGGAGAACCCCTCTTCCTTTTGTTTCATGATACAGCCGAGCACGCGGTTTTG ATATGCTGGACGACAGCCCArTrC |
| 19 | Chain-elongated nucleic acid 3 | | P04GACTGGTGTTGCGATTCACGATGCATCCGGCATAACGGAGCCATCCGAGCCCA ACAGCAGCCGGGGAGTTGACGAGTTCGTACCAGAACGTC |

*rN: Ribonucleotide (RNA)

TABLE 4

Amplification primer

| Sequence number | Name | Object | Sequence (5'-3') |
|---|---|---|---|
| 20 | FIP | Common | CGTCCAGCATATCAAAACCGCGCCT TCGGAGAACCCCTCT |
| 21 | BIP | | CGATTCACGATGCATCCGGCAGACG TTCTGGTACGAACTCG |
| 22 | LB | | CAACAGCAGCCGGGGAGTTG |

(2) Chain Elongation of Target Short-Chain Nucleic Acid

Ligation of the chain-elongation nucleic acid 2 and the chain-elongation nucleic acid 3 was confirmed by electrophoresis as described below. 50 mM of Tris-HCl (pH7.5), 5 mM of MgCl2, 1 mM of DTT, 20 μM of ATP, 20 U of Ribonuclease Inhibitor, and 33 pmol of each of miRNA (sequence number 1), the chain-elongation nucleic acid 2 (sequence numbers 4, 5), and the chain-elongation nucleic acid 3 (sequence number 10) in final concentration were added to 20 μL of the reaction liquid for annealing at 65° C. for 5 min and at 30° C. for 10 min. Then, T4 RNA Ligase2 was added in 2 U to incubate at 39° C. for 35 min for ligation. Electrophoresis of 10 μL of the reaction liquid was carried out by E-Gel Ex 2% (manufactured by Thermo Fisher Scientific K.K.). The result is shown in FIG. 12(b). As shown there, the target short-chain nucleic acid was present and the generation of a ligation product could be confirmed when RNA chimera was used as the chain-elongation nucleic acid 2.

(3) Amplification of an Amplification Template

Figure 13:
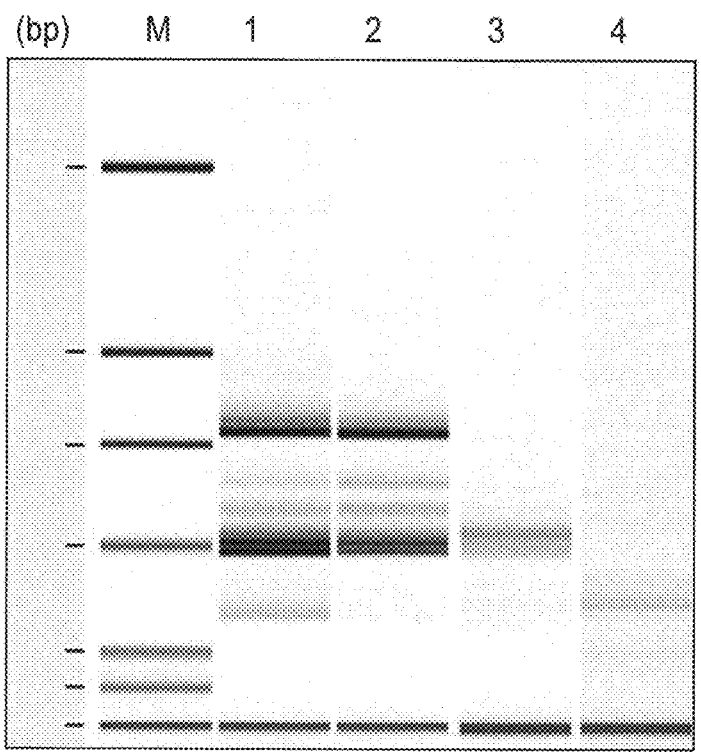
FIG. 13 is a diagram showing an experimental result.

Next, miRNA let-7-a (sequence number 1) in a low concentration was ligated and the obtained amplification template was used for LAMP. 0.2 fmol of miRNA and 0.2 fmol of each of the chain-elongation nucleic acid 2 (sequence number 5) and the chain-elongation nucleic acid 3 (sequence number 10) were mixed and 10 μL of the reaction liquid was used to cause ligation under the reaction conditions described in (2) above. Subsequently, 15 μL of the reaction liquid was added so as to obtain the following composition to perform LAMP at 63° C. for 90 min. The composition of the LAMP reaction liquid was as follows: all in the final concentration, 20 mM of Tris-HCl (pH 8.8), 30 mM of KCl, 8 mM of MgCl2, 10 mM of $(NH_4)_2SO_4$, 0.1% of Tween-20, 0.8 M of Betaine, 1.4 mM of each dNTPs, 1.6 μM of FIP (sequence number 20), 1.6 μM of BIP (sequence number 21), 0.8 μM of LF (sequence number 22), and 8 U of Bst DNA polymerase. Each reaction was carried out in 2-gang manner. As a result, while turbidity of the reaction liquid ligated by adding miRNA rose in 33 min on average, turbidity of the reaction liquid ligated without adding miRNA did not rise after 90 min of amplification. It was confirmed that LAMP occurs only if ligated in the presence of miRNA. Further, to check specificity of amplification products, ligation PC (sequence number 15) was similarly fragmented by a restriction enzyme Hinf I together with LAMP products and electrophoresis thereof was carried out. The result is as shown in FIG. 13. Samples ligated via miRNA produced the same hand pattern as that of the positive control, which confirmed specificity.

(4) Detection of Amplification Products

A DNA chip mounted with a nucleic acid probe of a sequence number 23, a sequence number 24, a sequence number 25, and a sequence number 26 was created as described below. Details of each sequence are shown in Table 5.

TABLE 5

Probe for detection

| Sequence number | Name | Object | Sequence (5'-3') |
|---|---|---|---|
| 23 | Probe | let-7-a | CTTCTTCCGCGCAGTCACTTGCTATCCTTACG |
| 24 | Probe | miR 21-5p | ATCCATGGAGTAAAGATCCACATCCCC |
| 25 | Probe | miR 21-3p | TGCTCGGCTGTATCATGAAACAAAAGGA |
| 26 | Probe | Negative control | CTCTTTTCTGCGCATAACAAAGTGCCATGA |

A probe DNA whose 3'-terminal is modified by thiol was prepared by a 100 μM mercapto hexanol solution to be 3 μM and was immobilized to a gold electrode formed on the glass with 200 μm in diameter using a 100 nL spot (each N=4). After drying, the probe DNA was washed and air-dried to obtain a DNA chip. LAMP products amplified in (3) above was thermally treated at 95° C. for 5 min and a 20×SSC buffer solution was added to obtain a 2×SSC buffer solution in the final solution and then, the LAMP products were put on the DNA chip to perform hybridization at 65° C. for 10 min. Then, a 0.2×SSC buffer solution was substituted and left at 35° C. for 3 min for washing and next, a PIPES buffer solution containing 75 μM of Hoechst 33258 was substituted and left at 25° C. for 1 min to allow Hoechst 33258 to bind to the double strand DNA. An oxidation current of Hoechst 33258 was measured by performing a potential sweep of the electrode at 100 mV/sec.

Figure 14:
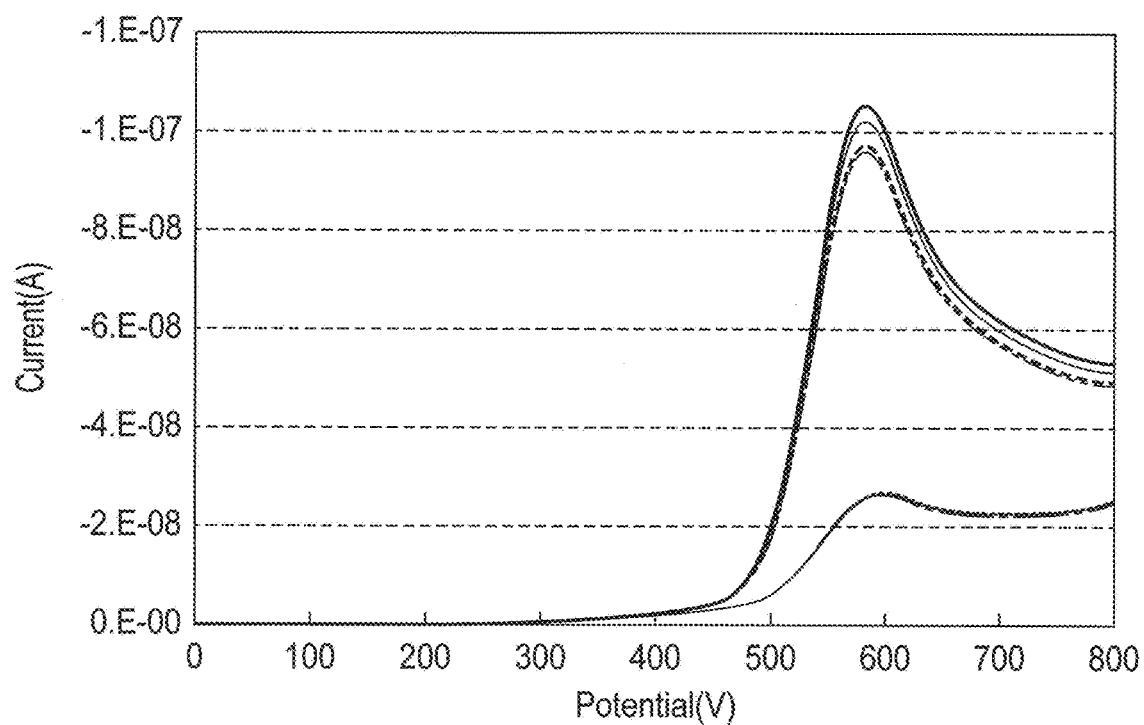
FIG. 14 is a diagram showing an experimental result.

The result is as shown in FIG. 14. A high voltage value of 97.9 nA on average was obtained from an electrode to which a probe (sequence number 23) of miRNA let-7-a and a low current value of 25 nA on average was obtained from to which an unrelated sequence, that is, a negative control (sequence number 26) was immobilized. Thus, due to hybridization of LAMP products, an electrochemical signal could be obtained.

It has been shown from the above that LAMP can specifically be carried out by using an amplification template obtained by annealing two chain-elongation nucleic acids to miRNA let-7-a for ligation and further, products thereof can be detected by an electrochemical DNA chip.

(5) Multiplex Detection

Next, multiplex detection of three types of miRNA, let-7-a (sequence number 1), miR 21-5p (sequence number 21), and miR 21-3p (sequence number 3), was carried out. For three types of miRNA, the sequence number 5, the sequence number 16, and the sequence number 18 were prepared as the sub-chain-elongation nucleic acid 2 and the sequence number 10, the sequence number 17, and the sequence number 19 were prepared as the sub-chain-elongation nucleic acid 3. 0.2 fmol of each of miRNA, the sub-chain-elongation nucleic acid 2, and the sub-chain-elongation nucleic acid 3 was mixed. Ligation and LAMP of the mixture were carried out under the conditions described in (3) described above. Primers for LAMP were, like in (3) described above, FIP (sequence number 20), BIP (sequence number 21), and LP (sequence number 22). Incidentally, the amplification time were reduced to 60 min. Multiple amplification products after the amplification were similarly measured by the method described in (4) described above using each of four DNA chips (a DNA chip 1, a DNA chip 2, a DNA chip 3, and a DNA chip 4) mounted with let-7-a probe (sequence number 23), 21-5p probe (sequence number 24), 21-3p (sequence number 25), and a negative control (sequence number 26) respectively. Samples brought to the DNA chip 1, the DNA chip 2, the DNA chip 3, and the DNA chip 4 were a sample A, a sample B, a sample C, and a sample D respectively and these samples contain target nucleic acids indicated by "+" in Table 6 respectively. The result is shown in Table 7.

TABLE 6

| Sample contents | | | | |
|---|---|---|---|---|
| Target short-chain nucleic acid | Sample A | Sample B | Sample C | Sample D |
| let-7-a | + | + | − | − |
| miR 21-5p | + | − | + | − |
| miR 21-3p | + | − | − | + |

TABLE 7

| DNA chip current value (Unit: nA) | | | | |
|---|---|---|---|---|
| Probe | Sample A | Sample B | Sample C | Sample D |
| Negative control | 29.7 | 26.6 | 28.5 | 28.5 |
| let-7-a | 114.9 | 132.3 | 27.1 | 31.1 |
| miR 21-5p | 106.8 | 37.7 | 115.0 | 32.3 |
| miR 21-3p | 111.8 | 31.3 | 31.5 | 112.6 |

Columns shown by solid frames in Table 7 show a positive result and this result matches the type of target nucleic acid contained by each sample. From the above result, it has been revealed that a signal is obtained from any probe and the sample state is correctly shown. Therefore, it has been shown that ligation and amplification reactions by LAMP of three types of markers can be carried out in the same container and markers can be detected by DNA chips corresponding to respective types. Incidentally, as shown in Table 7, specificity of each probe has been confirmed by single detection.

From the above, according to the present embodiment, it has been shown that a method and a kit capable of achieving multiplex chain elongation, amplification, and detection of a plurality of target short-chain nucleic acids can be provided.

2. Improvement of Reaction Efficiency by Doubling Chain by Chain-Elongation Nucleic Acid To stabilize chain-elongation nucleic acid, reactions can be made more efficient by partially doubling the chain of sub-chain-elongation nucleic acid. The chain was partially doubled by annealing the synthetic DNA of the sequence number 27 and the sequence number 28 respectively to the sub-chain-elongation nucleic acid 2 (sequence number 5) and the chain-elongation nucleic acid 3 (sequence number 10).

TABLE 8

| Sequence number | Name | Object | Sequence (5'-3') |
|---|---|---|---|
| 27 | Doubling chain | Common | GCAGTCACTTGCTATCCTTACG |
| 28 | Doubling chain | | TGGTACGAACTCGTCAACTCC |

Then, 0.2 fmol is mixed with each of 1E+4 to 8 copies of miRNA let-7-a (sequence number 1) to perform ligation in 10 µL of reaction liquid under the reaction conditions in (2) described above. Subsequently, 15 µL of the reaction liquid was added so as to obtain the following composition to perform LAMP at 63° C. for 90 min. The composition of the LAMP reaction liquid was as follows: all in the final concentration, 20 mM of Tris-HCl (pH 8.8), 30 mM of KCl, 8 mM of MgCl2, 10 mM of $(NH_4)_2SO_4$, 0.1% of Tween-20, 0.8 M of Betaine, 1.4 mM of each dNTPs, 1.6 µM of FIP (sequence number 20), 1.6 µM of BIP (sequence number 21), 0.8 µM of LF (sequence number 22), and 8 U of Bst DNA polymerase. Each reaction was carried out in 2-gang manner. For comparison, LAMP products using chain-elongation nucleic acids without double strand were similarly amplified. After the amplification of 90 min, LAMP products were fragmented by the restriction enzyme Hinf I and electrophoresis thereof was carried out, producing results shown in FIG. 15. For LAMP products from which the same band pattern as that of ligation PC was obtained and which were determined to have been specifically amplified, up to miRNA 1E+8 copies were achieved when the chain-elongation nucleic acid was used without doubling the strand, but up to miRNA 1E+7 to 6 copies were achieved and miRNA of lower concentration could be detected when the chain-elongation nucleic acid was used after doubling the strand.

From the above result, it has been revealed that according to an embodiment, a plurality of short-chain nucleic acids can be detected simply and easily.

Some embodiments of the present invention have been described, but these embodiments are presented by way of example and are not intended to limit the scope of the invention. These new embodiments can be carried out in various other embodiments and various omissions, substitutions, and alterations can be made without deviating from the spirit of the invention. These embodiments and modifications thereof are included in the scope and spirit of the invention and also included in the inventions described in claims and equivalents thereof.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method for detecting a plurality of target nucleic acids in a sample, wherein
the plurality of target nucleic acids are short-chain nucleic acids and respectively contain target sequences different from each other between the target nucleic acids, and the target sequences containing a first sub-target sequence on a 5'-terminal side and a second sub-target sequence on a 3'-terminal side,
the method comprising:
(a) preparing a chain-elongation nucleic acid set group to obtain a long-chain nucleic acid containing the respective target sequence for each of the plurality of target nucleic acids,
wherein
each chain-elongation nucleic acid set group contains a first sub-chain-elongation nucleic acid and a second sub-chain-elongation nucleic acid and
with respect to an object of the target sequences,
the first sub-chain-elongation nucleic acid contains a first target binding region containing a same sequence as the first sub-target sequence or a first complementary sequence complementary thereto at one terminal and a first amplification region at another terminal and
the second sub-chain-elongation nucleic acid contains a second target binding region containing a second complementary sequence complementary to the second sub-target sequence at a 3'-terminal and a second amplification region at a 5'-terminal and,
wherein at least one of the first sub-chain-elongation nucleic acid and the second sub-chain-elongation nucleic acid further contains a detection region, and when the first sub-chain-elongation nucleic acid contains the detection region, the detection region is present between the first target binding region and the first amplification region as a first detection region without overlapping the first target binding region, when the second sub-chain-elongation nucleic acid contains the detection region, the detection region is present between the second target binding region and the second amplification region as a second detection region without overlapping the second target binding region, and
the detection region is associated with the object target sequence in advance and has a sequence that is different from each other between the plurality of target nucleic acids, and
the chain-elongation nucleic acid set contains the detection region in at least one of the first sub-chain-elongation nucleic acid and the second sub-chain-elongation nucleic acid;
(b) preparing a universal primer set containing at least a first primer that binds to the first amplification region and a second primer that binds to the second amplification region to amplify the plurality of long-chain nucleic acids obtained from the chain-elongation nucleic acid set group in common;
(c) preparing a probe immobilized substrate including a substrate and a plurality of probes immobilized to a surface in contact with a first reaction field provided by the substrate,
wherein each of the plurality of probes
(1) contains a same sequence as that of a respective one of the plurality of sequences of the first detection region,
(2) contains a complementary sequence to a respective one of the plurality of sequences of the first detection region,
(3) contains a same sequence as that of a respective one of the plurality of sequences of the second detection region, and/or
(4) contains a complementary sequence to a respective one of the plurality of sequences of the second detection region;
(d) obtaining a long-chain nucleic acid group containing the first sub-chain-elongation nucleic acid and the second sub-chain-elongation nucleic acid or complementary sequences thereto for each of the plurality of target nucleic acids by bringing the sample and the chain-elongation nucleic acid set group prepared in the above (a) into a second reaction field to anneal and ligate each of the plurality of target nucleic acids and the first sub-chain-elongation nucleic acid corresponding thereto and the second sub-chain-elongation nucleic acid corresponding thereto and/or to elongate nucleic acids;
(e) obtaining an amplification product group by maintaining the long-chain nucleic acid group and the universal primer set under amplification conditions in the first reaction field;
(f) detecting presence/absence and/or an amount of hybridization between all the amplification product group generated in the above (e) and a first probe in the first reaction field; and
(g) detecting the plurality of target nucleic acids present in the sample based on a result in the above (f).

2. The method of claim 1, wherein the amplification is performed by a PCR method, and
the plurality of target nucleic acids are first to m-th target nucleic acids, where m is an integer equal to 2 or greater,
the plurality of target sequences are first to m-th target sequences corresponding respectively to the target nucleic acids, the first sub-target sequences are $1_1$ to $1_m$-th sub-target sequences corresponding respectively to the target sequences, the second sub-target sequences are $2_1$ to $2_m$-th sub-target sequences corresponding respectively to the target sequences,
the sequence of the first amplification region is common among $1_1$ to $1_m$-th sub-chain-elongation nucleic acids, the first amplification region contains a sequence that binds to the sequence of the first primer,
the sequence of the second amplification region is common among $2_1$ to $2_m$-th sub-chain-elongation nucleic acids, and the second amplification region contains a sequence that binds to the sequence of the second primer.

3. The method of claim 2, wherein
obtaining the long-chain nucleic acid group includes annealing and a ligation reaction of the nucleic acids,
the first sub-chain-elongation nucleic acid has the first target binding region present at a 5'-terminal and the first amplification region present on a 3'-terminal side and has a phosphorylated 5'-terminal, and
the sequence of the first target binding region is the complementary sequence of the first sub-target sequence.

4. The method of claim 2, wherein
obtaining the long-chain nucleic acid group includes an elongation reaction using DNA polymerase, the first sub-chain-elongation nucleic acid has the first target binding region present at the 3'-terminal and the first amplification region present on the 5'-terminal side, and the sequence of the first target binding region is the same sequence as the first sub-target sequence.

5. The method of claim 1, wherein the amplification is performed by LAMP, and the target nucleic acids are first to m-th target nucleic acids, where m is an integer equal to 2 or greater, the plurality of target sequences are first to m-th target sequences corresponding respectively to the target nucleic acids, the first sub-target sequences are $1_1$ to $1_m$-th sub-target sequences corresponding respectively to the target sequences, the second sub-target sequences are $2_1$ to $2_m$-th sub-target sequences corresponding respectively to the target sequences, the first amplification region is an F2 binding region, and the first sub-chain-elongation nucleic acid contains an F1 binding region, the F1 binding region being present between the F2 binding region and a first sub-target binding region, when the first detection region is contained in the first sub-chain-elongation nucleic acid, the first detection region is present, on the first sub-chain-elongation nucleic acid, between a base adjacent to the F1 binding region and a region overlapping with the F2 binding region to avoid overlapping with the F1 binding region, and contains a region without overlapping the F2 binding region, the sequence of the second amplification region is a B2 binding region, and the second sub-chain-elongation nucleic acid contains a B1 binding region, the B1 binding region being present between the B2 binding region and a second sub-target binding region, when the second detection region is contained in the second sub-chain-elongation nucleic acid, the second detection region is present, on the second sub-chain-elongation nucleic acid, in a range on the 3'-terminal side with respect to the 5'-terminal of the B2 binding region from a 5'-terminal side base at the 5'-terminal of the B1 binding region, and contains a region without overlapping the B2 binding region, at least one of the first detection region and the second detection region is contained in the chain-elongation nucleic acid set, the first primer is an FIP primer containing an F1c sequence at the 5'-terminal and an F2 sequence at the 3'-terminal, the second primer is a BIP primer containing a B1c sequence at the 5'-terminal and a B2 sequence at the 3'-terminal, the first detection regions are $1_1$ to $1_m$-th detection regions corresponding respectively to the target sequences, the second detection regions are $2_1$ to $2_m$-th detection regions corresponding respectively to the target sequences, and the probes are $1_1$ to $1_m$-th probes and/or $2_1$ to $2_m$-th probes depending on presence of the first detection region and the second detection region.

6. The method of claim 5, wherein obtaining the long-chain nucleic acid group includes annealing and an ligation reaction of the nucleic acids, the first sub-target binding region of each of the plurality of target nucleic acids is the first complementary sequence and present at the 5'-terminal of the $1_1$ to $1_m$-th sub-chain-elongation nucleic acids that corre-sponds thereto and these sub-chain-elongation nucleic acids have the 5'-terminal that is phosphorylated, the sequence of the first primer binding region is an F2c sequence, the F1 binding region is an F1c sequence, the first sub-chain-elongation nucleic acid has the first sub-target binding region present at the 5'-terminal, and the F1c sequence and the F2c sequence are present in this order from there toward the 3'-terminal side.

7. The method of claim 5, wherein obtaining the long-chain nucleic acid group includes an elongation reaction using DNA polymerase, the first sub-target binding region of each of the plurality of target nucleic acids has the same sequence as the first sub-target binding region and is present at the 3'-terminal of the $1_1$ to $1_m$-th sub-chain-elongation nucleic acids that corresponds thereto, the sequence of the first primer binding region is an F2 sequence, the F1 binding region is an F1 sequence, the first sub-chain-elongation nucleic acid has the first sub-target binding region present at the 3'-terminal, and the F1 sequence and the F2 sequence are present in this order from there toward the 5'-terminal side.

8. The method of claim 4, wherein the DNA polymerase is reverse transcriptase.

9. The method of claim 7, wherein the DNA polymerase is reverse transcriptase.

10. The method of claim 5, wherein the amplification is performed by LAMP, the first primer is prepared as a first primer set by being combined with at least an LF primer, the first sub-chain-elongation nucleic acid further contains an LF binding region, the LF binding region is present between a base adjacent to the F1 binding region and an end of a region overlapping with the F2 binding region without containing the F1 binding region, and has a region without overlapping the F2 binding region and/or the second primer is prepared as a second primer set by being combined with an LB primer, the second sub-chain-elongation nucleic acid further contains an LB sequence, the LB sequence is on the 3'-terminal side from the 5'-terminal of the B2 sequence and on the 5'-terminal side from the 5'-terminal of the B1 sequence, and has a region without overlapping the B2 binding region.

11. The method of claim 5, wherein the first primer is prepared as a first primer set by being combined with at least an F3 primer, the first sub-chain-elongation nucleic acid further contains an F3 binding region, the F3 binding region being present outside the F2 binding region toward a terminal where the first sub-target binding region is not present and/or the second primer is prepared as a first primer set by being combined with at least a B3 primer, the second sub-chain-elongation nucleic acid further contains a B3 sequence, and the B3 sequence presenting on the 5'-terminal side of the B2 sequence.

12. A method for analyzing first to n-th series, where n is an integer equal to 2 or greater, using the method of claim 1, wherein a target nucleic acid group preset for each of the first to n-th series is contained as a small item set, the small item set contains a plurality of small items, the plurality of small items corresponding to detecting each of the plurality of target nucleic acid groups, the plurality of small item sets contain the plurality of target nucleic acids in independent numbers and these numbers are identical to each other or different from each other, the probe immobilized substrate is a universal probe immobilized substrate common to the first to n-th series, and the above (a) to the above (g) are performed to detect the plurality of target nucleic acids corresponding to the small item set for each series independently of the each series, and further comprising:

(h) obtaining an analysis result of each of the first to n-th series based on a result of the above (g); and (i) obtaining, if desired, an analysis result of each of further n+(1 to s) series based on results obtained by additionally performing the above (a) to the above (g) for the n+(1 to s) series, where s is an integer equal to 2 or greater.

13. The method of claim 12, wherein the numbers of small items contained in each of the first to n-th small item sets is $m_1$ to $m_n$, a maximum value in the first to n-th small item sets is $m_{max}$, where m and n are independent of each other and integers equal to 2 or greater, any x-th series among the first to n-th series is analyzed using an x-th small item set corresponding thereto, the x-th small item set contains $1_x$-th to $m_x$-th small items, and $1 \leq m_x \leq m_{max}$ applies.

14. The method of claim 1, wherein obtaining the amplification product group and detecting presence/absence and/or an amount of the hybridization are carried out in a same period for continuous monitoring of presence/absence and/or an amount of the hybridization or detection or measurement thereof over time at a plurality of points in time.

15. The method of claim 1, wherein the first sub-chain-elongation nucleic acid and the second sub-chain-elongation nucleic acid contain LNA or PNA in a portion thereof.

16. The method of claim 1, wherein the first sub-chain-elongation nucleic acid and the second sub-chain-elongation nucleic acid each have a double strand at least partially excluding the first target binding region and the second target binding region respectively.

17. A method for detecting a plurality of target nucleic acids in a sample, wherein the plurality of target nucleic acids are short-chain nucleic acids and respectively contain target sequences different from each other between the target nucleic acids, and the target sequences containing a first sub-target sequence on a 5'-terminal side and a second sub-target sequence on a 3'-terminal side, the method comprising:

(a) preparing a chain-elongation nucleic acid set group to obtain a long-chain nucleic acid containing the respective target sequence for each of the plurality of target nucleic acids, wherein each chain-elongation nucleic acid set group contains a first sub-chain-elongation nucleic acid and a second sub-chain-elongation nucleic acid and with respect to an object of the target sequences, the first sub-chain-elongation nucleic acid contains a first target binding region containing a same sequence as the first sub-target sequence or a first complementary sequence complementary thereto at one terminal and a first amplification region at another terminal and the second sub-chain-elongation nucleic acid contains a second target binding region containing a second complementary sequence complementary to the second sub-target sequence at a 3'-terminal and a second amplification region at a 5'-terminal and, wherein at least one of the first sub-chain-elongation nucleic acid and the second sub-chain-elongation nucleic acid further contains a detection region, and when the first sub-chain-elongation nucleic acid contains the detection region, the detection region is present between the first target binding region and the first amplification region as a first detection region without overlapping the first target binding region, when the second sub-chain-elongation nucleic acid contains the detection region, the detection region is present between the second target binding region and the second amplification region as a second detection region without overlapping the second target binding region, and the detection region is associated with the object target sequence in advance and has a sequence that is different from each other between the plurality of target nucleic acids, and the chain-elongation nucleic acid set contains the detection region in at least one of the first sub-chain-elongation nucleic acid and the second sub-chain-elongation nucleic acid;

(b) preparing a universal primer set containing at least a first primer that binds to the first amplification region and a second primer that binds to the second amplification region to amplify the plurality of long-chain nucleic acids obtained from the chain-elongation nucleic acid set group in common;

(c) preparing a probe immobilized substrate including a substrate and a plurality of probes immobilized to a surface in contact with a first reaction field provided by the substrate, wherein each of the plurality of probes (1) contains a same sequence as that of a respective one of the plurality of sequences of the first detection region, (2) contains a complementary sequence to a respective one of the plurality of sequences of the first detection region, (3) contains a same sequence as that of a respective one of the plurality of sequences of the second detection region, and/or (4) contains a complementary sequence to a respective one of the plurality of sequences of the second detection region;

(d) obtaining a long-chain nucleic acid group containing the first sub-chain-elongation nucleic acid and the second sub-chain-elongation nucleic acid or complementary sequences thereto for each of the plurality of target nucleic acids by bringing the sample and the chain-elongation nucleic acid set group prepared in the above (a) into a second reaction field to anneal and ligate each of the plurality of target nucleic acids and the first sub-chain-elongation nucleic acid corresponding thereto and the second sub-chain-elongation nucleic acid corresponding thereto and/or to elongate nucleic acids;

(e) obtaining an amplification product group by maintaining the long-chain nucleic acid group and the universal primer set under amplification conditions in a third reaction field which is connected to the first reaction field;

(f) detecting presence/absence and/or an amount of hybridization between all the amplification product group generated in the above (e) and a first probe in the first reaction field; and (g) detecting the plurality of target nucleic acids present in the sample based on a result in the above (f).

18. The method of claim 1, wherein the universal primer set is a LAMP primer set, and the step (e) is performed by a LAMP method.

19. The method of claim 1, wherein during the (d) obtaining, each of the plurality of target nucleic acids of the sample are contacted with the chain-elongation nucleic acid set group prepared in the above (a) in a common reaction field within the same period to anneal and ligate each of the plurality of target nucleic acids and the first sub-chain-elongation nucleic acid corresponding thereto and the second sub-chain-elongation nucleic acid corresponding thereto.

20. The method of claim 19, wherein the (e) obtaining is carried out in the same reaction field as the (d) obtaining.

21. The method of claim 17, wherein the universal primer set is a LAMP primer set, and the step (e) is performed by a LAMP method.

* * * * *

```
                         SEQUENCE LISTING

<160> NUMBER OF SEQ ID NOS: 28

<210> SEQ ID NO 1
    <211> LENGTH: 22
    <212> TYPE: RNA
    <213> ORGANISM: Artificial Sequence
    <220> FEATURE:
    <223> OTHER INFORMATION: miRNA

<400> SEQUENCE: 1
ugagguagua gguuguauag uu                                              22

<210> SEQ ID NO 2
    <211> LENGTH: 22
    <212> TYPE: RNA
    <213> ORGANISM: Artificial Sequence
    <220> FEATURE:
    <223> OTHER INFORMATION: miRNA

<400> SEQUENCE: 2
uagcuuauca gacugauguu ga                                              22

<210> SEQ ID NO 3
    <211> LENGTH: 21
    <212> TYPE: RNA
    <213> ORGANISM: Artificial Sequence
    <220> FEATURE:
    <223> OTHER INFORMATION: miRNA

<400> SEQUENCE: 3
caacaccagu cgaugggcug u                                               21

<210> SEQ ID NO 4
    <211> LENGTH: 87
    <212> TYPE: DNA
    <213> ORGANISM: Artificial Sequence
    <220> FEATURE:
    <223> OTHER INFORMATION: elongation nucleic acid
```

```
<400> SEQUENCE: 4
ccttcggaga acccctctct acgtaaggat agcaagtgac tgcgcggaag aagtcgcggt    60
tttgatatgc tggacgaact atacaac                                       87

<210> SEQ ID NO 5
<211> LENGTH: 87
<212> TYPE: DNA
<213> ORGANISM: Artificial Sequence
<220> FEATURE:
<223> OTHER INFORMATION: elongation nucleic acid

<400> SEQUENCE: 5
ccttcggaga acccctctct acgtaaggat agcaagtgac tgcgcggaag aagtcgcggt    60
tttgatatgc tggacgaact atacaac                                       87

<210> SEQ ID NO 6
<211> LENGTH: 18
<212> TYPE: DNA
<213> ORGANISM: Artificial Sequence
<220> FEATURE:
<223> OTHER INFORMATION: amplification sequence

<400> SEQUENCE: 6
ccttcggaga acccctct                                                 18

<210> SEQ ID NO 7
<211> LENGTH: 36
<212> TYPE: DNA
<213> ORGANISM: Artificial Sequence
<220> FEATURE:
<223> OTHER INFORMATION: detection sequence

<400> SEQUENCE: 7
ctacgtaagg atagcaagtg actgcgcgga agaagt                             36

<210> SEQ ID NO 8
<211> LENGTH: 22
<212> TYPE: DNA
<213> ORGANISM: Artificial Sequence
<220> FEATURE:
<223> OTHER INFORMATION: amplification sequence

<400> SEQUENCE: 8
cgcggttttg atatgctgga cg                                            22

<210> SEQ ID NO 9
<211> LENGTH: 11
<212> TYPE: DNA
<213> ORGANISM: Artificial Sequence
<220> FEATURE:
<223> OTHER INFORMATION: target binding site

<400> SEQUENCE: 9
aactatacaa c                                                        11

<210> SEQ ID NO 10
<211> LENGTH: 92
<212> TYPE: DNA
<213> ORGANISM: Artificial Sequence
<220> FEATURE:
<223> OTHER INFORMATION: elongation nucleic acid
```

<400> SEQUENCE: 10
ctactacctc acgattcacg atgcatccgg cataacggag ccatccgagc ccaacagcag    60
ccggggagtt gacgagttcg taccagaacg tc                                  92

<210> SEQ ID NO 11
<211> LENGTH: 11
<212> TYPE: DNA
<213> ORGANISM: Artificial Sequence
<220> FEATURE:
<223> OTHER INFORMATION: target binding site

<400> SEQUENCE: 11
ctactacctc a                                                         11

<210> SEQ ID NO 12
<211> LENGTH: 21
<212> TYPE: DNA
<213> ORGANISM: Artificial Sequence
<220> FEATURE:
<223> OTHER INFORMATION: amplification sequence

<400> SEQUENCE: 12
cgattcacga tgcatccggc a                                              21

<210> SEQ ID NO 13
<211> LENGTH: 40
<212> TYPE: DNA
<213> ORGANISM: Artificial Sequence
<220> FEATURE:
<223> OTHER INFORMATION: amplification sequence

<400> SEQUENCE: 13
taacggagcc atccgagccc aacagcagcc ggggagttga                          40

<210> SEQ ID NO 14
<211> LENGTH: 20
<212> TYPE: DNA
<213> ORGANISM: Artificial Sequence
<220> FEATURE:
<223> OTHER INFORMATION: amplification sequence

<400> SEQUENCE: 14
cgagttcgta ccagaacgtc                                                20

<210> SEQ ID NO 15
<211> LENGTH: 179
<212> TYPE: DNA
<213> ORGANISM: Artificial Sequence
<220> FEATURE:
<223> OTHER INFORMATION: long nucleic acid

<400> SEQUENCE: 15
ccttcggaga acccctctct acgtaaggat agcaagtgac tgcgcggaag aagtcgcggt    60
tttgatatgc tggacgaact atacaaccta ctacctcacg attcacgatg catccggcat   120
aacggagcca tccgagccca acagcagccg gggagttgac gagttcgtac cagaacgtc   179

<210> SEQ ID NO 16
<211> LENGTH: 80
<212> TYPE: DNA
<213> ORGANISM: Artificial Sequence
<220> FEATURE:
<223> OTHER INFORMATION: elongation nucleic acid

<400> SEQUENCE: 16
ccttcggaga acccctctgg ggatgtggat ctttactcca tggataacgc ggttttgata    60
tgctggacgt caacatcagt                                                80

<210> SEQ ID NO 17
<211> LENGTH: 92
<212> TYPE: DNA
<213> ORGANISM: Artificial Sequence
<220> FEATURE:
<223> OTHER INFORMATION: elongation nucleic acid

<400> SEQUENCE: 17
ctgataagct acgattcacg atgcatccgg cataacggag ccatccgagc ccaacagcag    60
ccggggagtt gacgagttcg taccagaacg tc                                  92

<210> SEQ ID NO 18
<211> LENGTH: 78
<212> TYPE: DNA
<213> ORGANISM: Artificial Sequence
<220> FEATURE:
<223> OTHER INFORMATION: elongation nucleic acid

<400> SEQUENCE: 18
ccttcggaga acccctcttc cttttgtttc atgatacagc cgagcacgcg gttttgatat    60
gctggacgac agcccatc                                                  78

<210> SEQ ID NO 19
<211> LENGTH: 92
<212> TYPE: DNA
<213> ORGANISM: Artificial Sequence
<220> FEATURE:
<223> OTHER INFORMATION: elongation nucleic acid

<400> SEQUENCE: 19
gactggtgtt gcgattcacg atgcatccgg cataacggag ccatccgagc ccaacagcag    60
ccggggagtt gacgagttcg taccagaacg tc                                  92

<210> SEQ ID NO 20
<211> LENGTH: 40
<212> TYPE: DNA
<213> ORGANISM: Artificial Sequence
<220> FEATURE:
<223> OTHER INFORMATION: primer

<400> SEQUENCE: 20
cgtccagcat atcaaaaccg cgccttcgga gaacccctct                          40

<210> SEQ ID NO 21
<211> LENGTH: 41
<212> TYPE: DNA
<213> ORGANISM: Artificial Sequence
<220> FEATURE:
<223> OTHER INFORMATION: primer

<400> SEQUENCE: 21
cgattcacga tgcatccggc agacgttctg gtacgaactc g                        41

<210> SEQ ID NO 22
<211> LENGTH: 20
<212> TYPE: DNA
<213> ORGANISM: Artificial Sequence

```
<220> FEATURE:
<223> OTHER INFORMATION: primer

<400> SEQUENCE: 22
caacagcagc cggggagttg                                              20

<210> SEQ ID NO 23
<211> LENGTH: 32
<212> TYPE: DNA
<213> ORGANISM: Artificial Sequence
<220> FEATURE:
<223> OTHER INFORMATION: probe

<400> SEQUENCE: 23
cttcttccgc gcagtcactt gctatcctta cg                                32

<210> SEQ ID NO 24
<211> LENGTH: 27
<212> TYPE: DNA
<213> ORGANISM: Artificial Sequence
<220> FEATURE:
<223> OTHER INFORMATION: probe

<400> SEQUENCE: 24
atccatggag taaagatcca catcccc                                      27

<210> SEQ ID NO 25
<211> LENGTH: 28
<212> TYPE: DNA
<213> ORGANISM: Artificial Sequence
<220> FEATURE:
<223> OTHER INFORMATION: probe

<400> SEQUENCE: 25
tgctcggctg tatcatgaaa caaaagga                                     28

<210> SEQ ID NO 26
<211> LENGTH: 30
<212> TYPE: DNA
<213> ORGANISM: Artificial Sequence
<220> FEATURE:
<223> OTHER INFORMATION: probe

<400> SEQUENCE: 26
ctcttttctg cgcataacaa agtgccatga                                   30

<210> SEQ ID NO 27
<211> LENGTH: 22
<212> TYPE: DNA
<213> ORGANISM: Artificial Sequence
<220> FEATURE:
<223> OTHER INFORMATION: sub-elongation nucleic acid

<400> SEQUENCE: 27
gcagtcactt gctatcctta cg                                           22

<210> SEQ ID NO 28
<211> LENGTH: 21
<212> TYPE: DNA
<213> ORGANISM: Artificial Sequence
<220> FEATURE:
<223> OTHER INFORMATION: probe

<400> SEQUENCE: 28
tggtacgaac tcgtcaactc c                                            21
```